United States Patent [19]

Dakov

[11] Patent Number: 5,720,755
[45] Date of Patent: Feb. 24, 1998

[54] TUBULAR SUTURING DEVICE AND METHODS OF USE

[76] Inventor: Pepi Dakov, 68 2nd Pl., Brooklyn, N.Y. 11231

[21] Appl. No.: 538,434

[22] Filed: Oct. 2, 1995

Related U.S. Application Data

[63] Continuation-in-part of Ser. No. 374,043, Jan. 18, 1995, abandoned.

[51] Int. Cl.⁶ ............................................ A61B 17/10
[52] U.S. Cl. .................... 606/139; 606/153; 227/179.1
[58] Field of Search ........................ 606/139, 148, 606/152, 153, 151; 227/175.1, 176.1, 179.1; 623/12, 11

[56] References Cited

U.S. PATENT DOCUMENTS

| | | | |
|---|---|---|---|
| 3,105,492 | 10/1963 | Jeckel | 623/1 |
| 3,435,823 | 4/1969 | Edwards | 606/153 |
| 3,519,187 | 7/1970 | Kapitanov | 227/19 |
| 4,872,874 | 10/1989 | Taheri | 623/1 |
| 5,151,105 | 9/1992 | Kwan-Gett | 606/153 |
| 5,188,638 | 2/1993 | Tzakis | 606/153 |
| 5,242,457 | 9/1993 | Akopov et al. | 606/139 |
| 5,314,436 | 5/1994 | Wilk | 606/153 |
| 5,346,115 | 9/1994 | Perouse | 227/19 |
| 5,395,030 | 3/1995 | Kuramoto et al. | 227/179 |

FOREIGN PATENT DOCUMENTS

| | | |
|---|---|---|
| 2171477 | 9/1973 | France . |
| 2038226 | 7/1980 | United Kingdom . |

Primary Examiner—Michael Buiz
Assistant Examiner—Patrick W. Rasche

[57] ABSTRACT

A tubular suturing device for suturing new types of tubular connectors to the ends of tubular structures such as blood vessels. The suturing device comprises a substantially rigid body containing multiple staples disposed within receptacles arranged radially along a suturing surface of the body, and an actuating mechanism moving in predetermined spaces producing multiple forces ejecting the staples in an approximately radial direction. Various embodiments and methods are provided for attachment of different types of tubular connectors to the external or internal surface of the tubular structures by staples ejected in an inward or outward radial direction; for new methods of clinching of the prongs of the ejected staples; for new surgical procedures and for new instruments facilitating their performance.

55 Claims, 37 Drawing Sheets

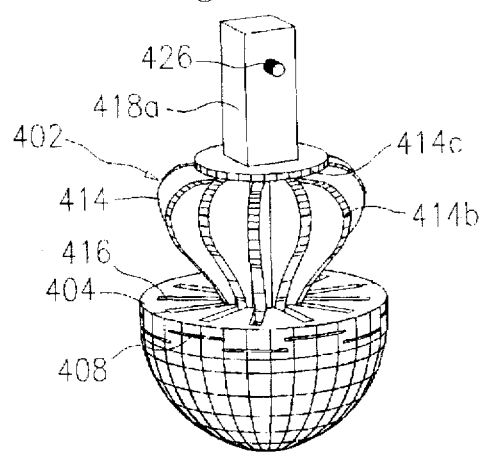
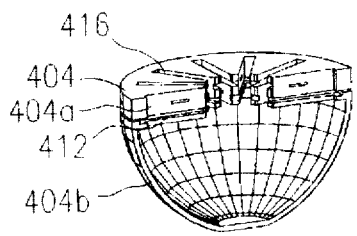
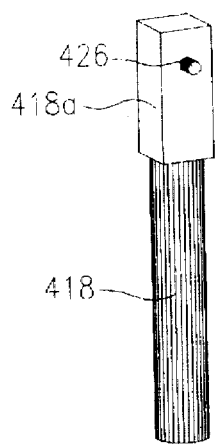
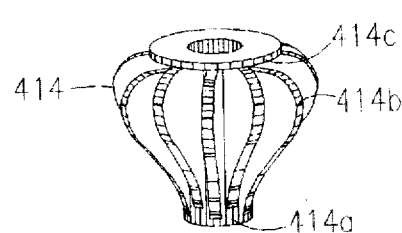
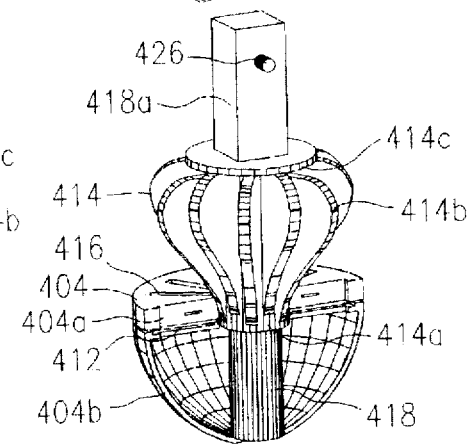
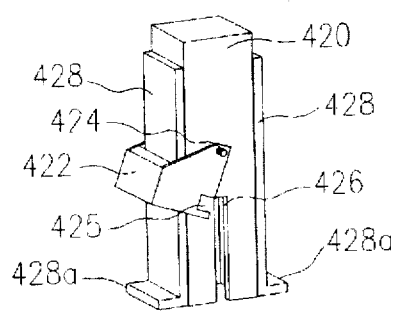
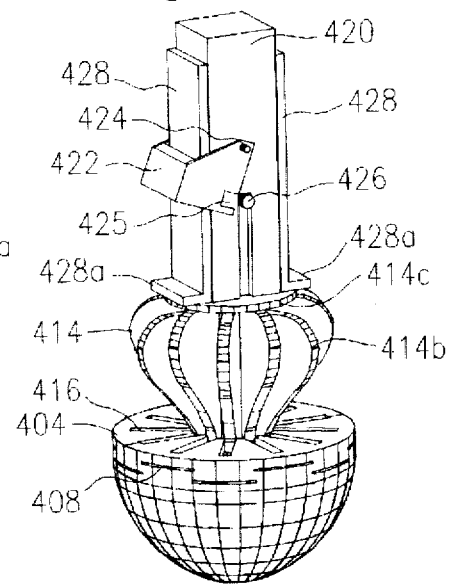

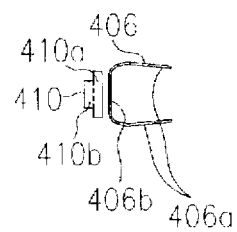
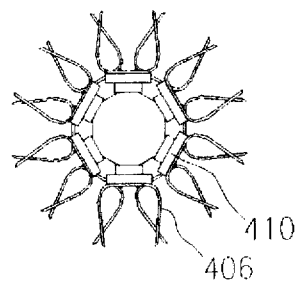
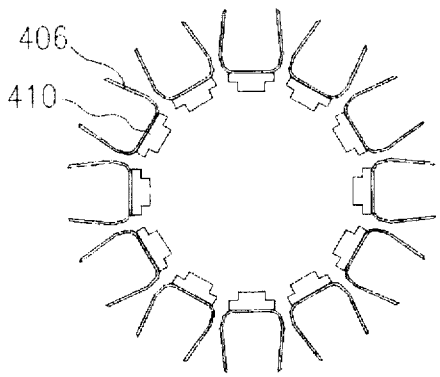
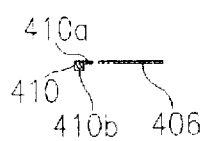
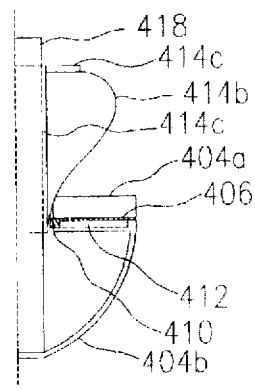
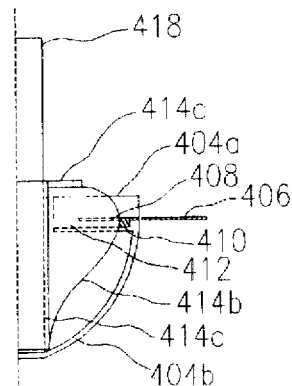
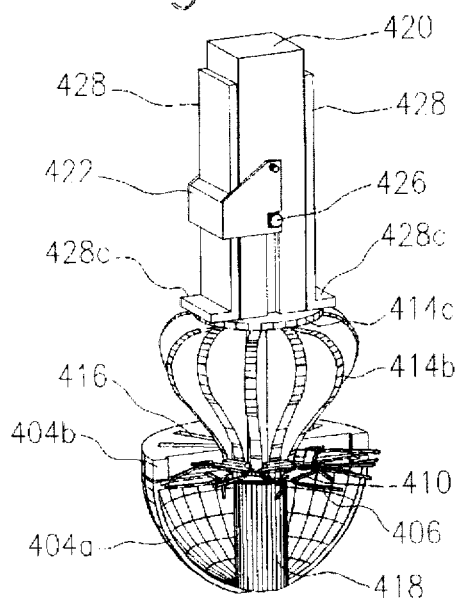
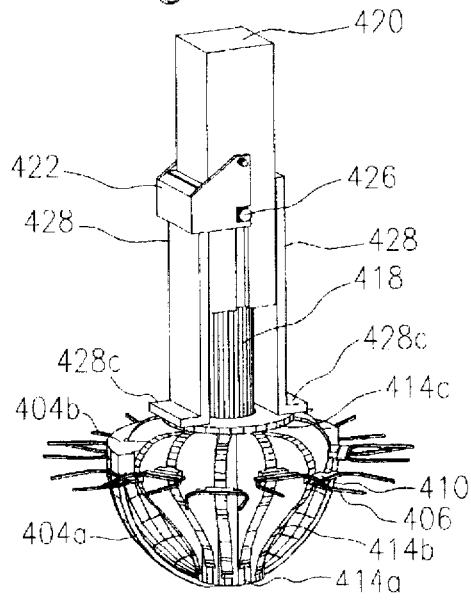

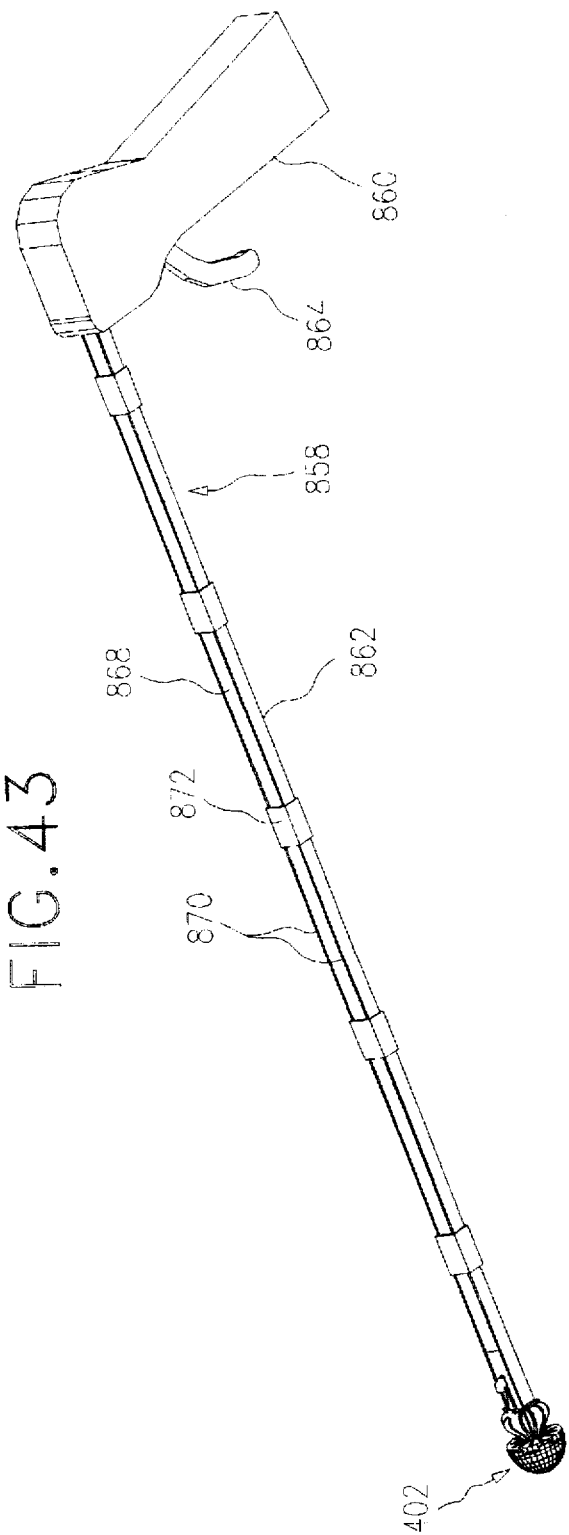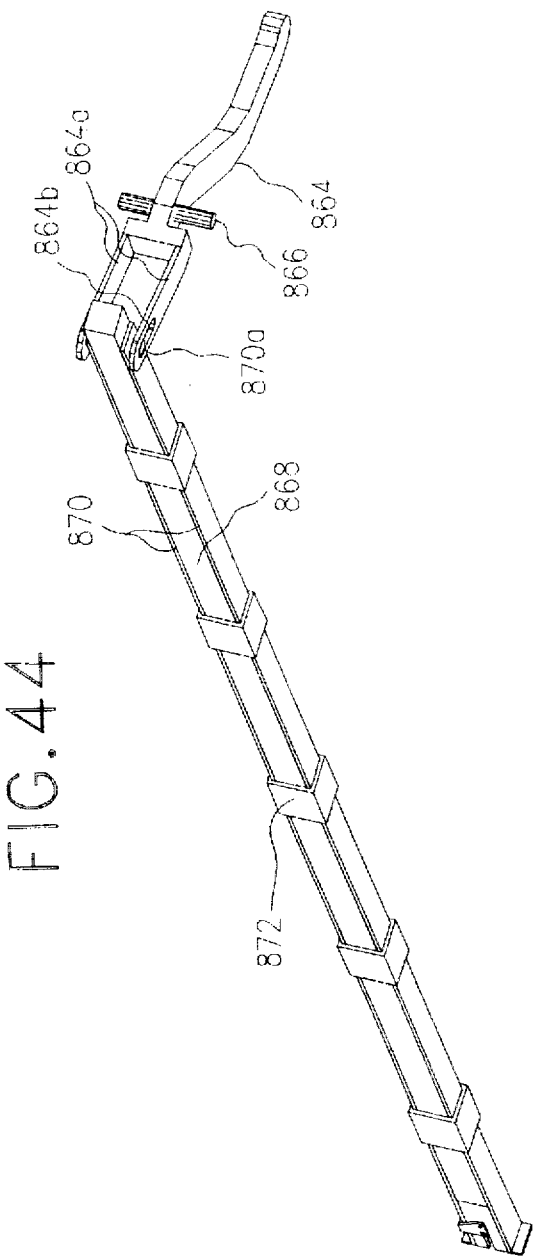

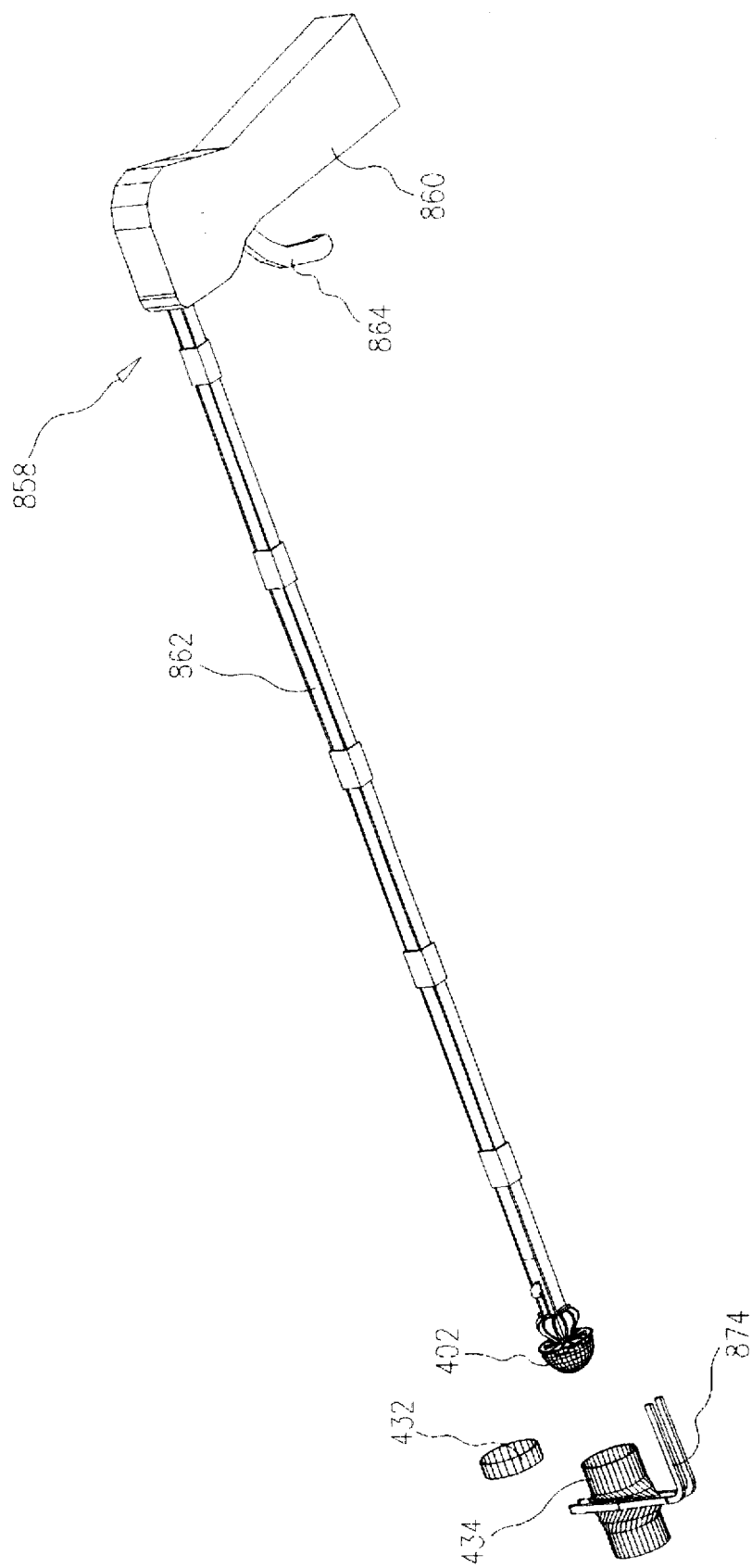

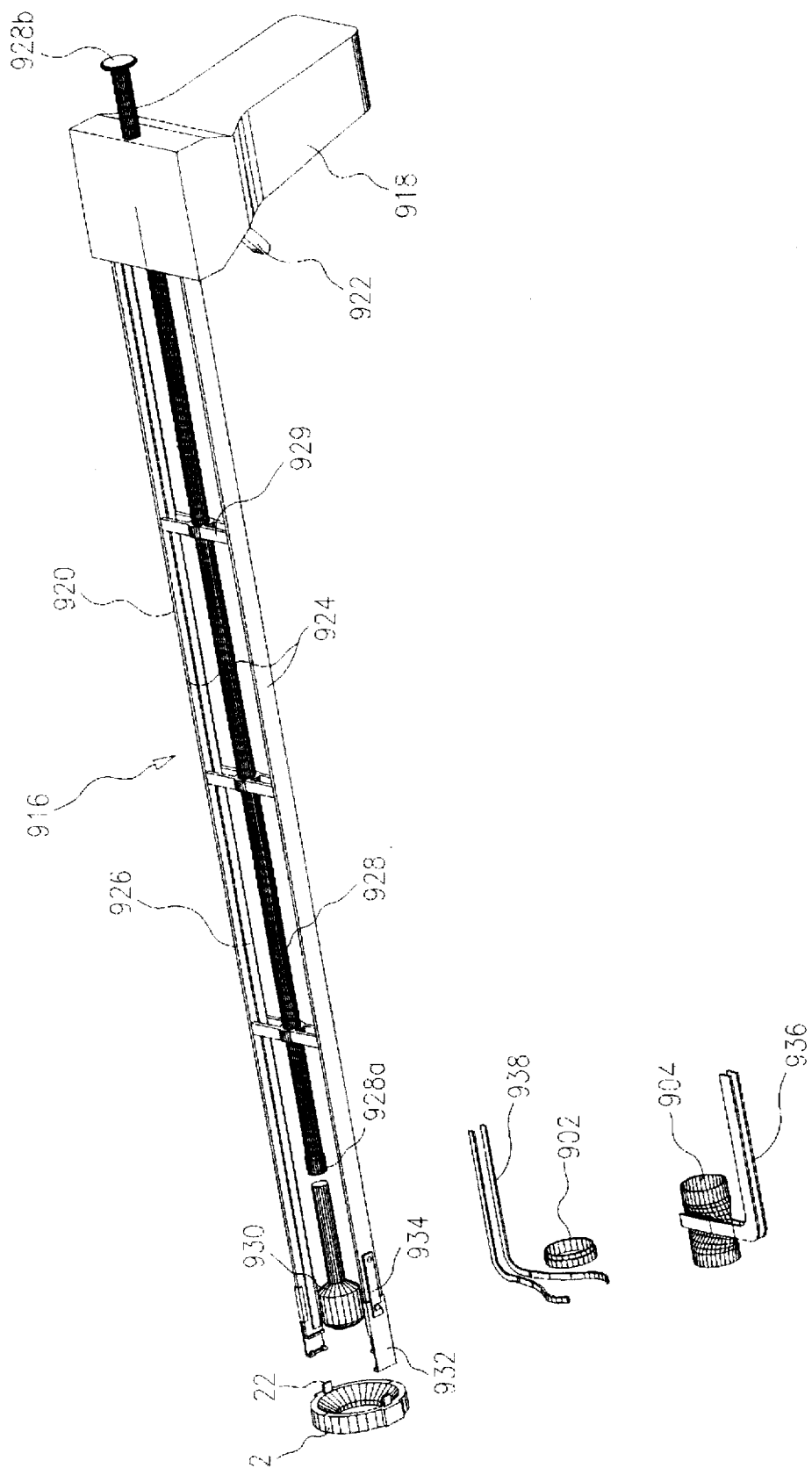

TUBULAR SUTURING DEVICE AND METHODS OF USE

This is a continuation-in-part application of U.S. patent application Ser. No. 08/374,043 filed on Jan. 18, 1995, now abandoned.

FIELD OF THE INVENTION

This invention pertains to automatic suturing devices for anastomosing tubular structures, and more specifically to medical suturing instruments for anastomosing the severed ends of blood vessels and similar tubular structures such as intestines, bile ducts, urinary ducts, and other tubular organs without changing their lumen and anatomical configurations by staples ejected in approximately radial direction. The radially ejected staples suture to their ends tubular connecting means that comprise an inner and an outer tubular portions affixed to each other, one of which is a substantially rigid portion with a predetermined coupling surface and the other is a substantially soft portion having a sufficient tensile strength to withhold clinched staples.

BACKGROUND OF THE INVENTION

The conventional way of connecting severed blood vessels is by manual placement of sutures. The surgical procedure is time consuming and demands highly specialized skills. It usually takes about ten to twenty minutes to complete for each anastomosis. For many operative interventions, multiple such connections are required. The tissues deprived of blood supply during the procedure suffer from ischemia, which can produce degenerative and necrotic changes. Bleeding occurs frequently from the manually performed anastomoses, which prolongs and complicates the procedures. Repeated operative interventions might be necessitated for extensive postoperative hemorrhages. Blood clots formed around the anastomoses and drainages placed to evacuate bleedings are the most important factors for the frequent development of infections.

Automatic staplers for suturing hollow organs have already established wide spread application in gastrointestinal surgery. Various similar devices have been proposed for implementation in cardiovascular surgery, but none have found any practical implementation. Principally, their methods of operations are to eject staples in axial direction to the walls of flanged or cuffed blood vessels. Flanging or cuffing of the substantially rigid walls of blood vessels (especially of arteries) is a much more difficult and time consuming procedure, as compared to that of gastrointestinal organs. Such manipulations are actually impossible to perform within limited space and deep into the body, which makes these methods unsuitable for application with blood vessels.

Devices for accomplishing anastomoses of blood vessels by ejecting staples in radial direction are described by Rasgulov (FRA-2,171,477) and Tzakis (U.S. Pat. No. 5,188,638). In both cases, the vessel walls have to be cuffed in order to perform the procedure, which is practically inapplicable as explained above. Perouse shows a device for accomplishing anastomoses of blood vessels without changing their natural configurations by ejecting staples in radial direction (U.S. Pat. No. 5,346,115). The application of the device is limited for suturing only of flexible prostheses, and only to the internal surface of the blood vessels. The internally attached prosthesis narrows the lumen of the anastomosed organs. Therefore, the device can be used only with relatively large structures and cannot be implemented with small blood vessels. Moreover, the uneven surface of the internal anastomotic line impedes the blood flow and increases the chances for thrombus formations and/or stenosis. The surgical procedure is not sufficiently easy, fast, and reliable to find practical implementation with blood vessels, which need to be anastomosed in a short period of time and in a secure manner.

The present invention solves all these problems. It provides a new tubular suturing device ejecting staples radially and methods for accomplishing anastomoses on tubular sutures without changing their lumen and configurations, which is achieved in a fast, easy and reliable manner, by attachment of new types of tubular connecting means such as connectors and/or prostheses to the severed ends of the tubular structures.

OBJECTS AND SUMMARY

It is an object of this invention to provide a tubular suturing device ejecting staples in approximately radial direction for accomplishing anastomoses of tubular structures without changing their lumen and natural configurations by suturing of tubular connecting means to their severed ends.

It is a further object of this invention to provide a method for accomplishing anastomoses of tubular structures without changing their lumen and natural configurations by suturing of tubular connecting means to their severed ends by a tubular suturing device ejecting staples radially.

It is a still further object of this invention to provide a tubular suturing device ejecting staples in approximately radial direction for accomplishing anastomoses of tubular structures with constant or changing diameter without changing their lumen and natural configurations by suturing tubular connecting means to their severed ends.

It is a still further object of this invention to provide a tubular suturing device ejecting staples in approximately radial direction for accomplishing anastomoses of tubular structures with cylindrical, ovoid, ellipsoid, or the like form without changing their lumen and natural configurations by suturing of tubular connecting means to their severed ends.

It is a still further object of this invention to provide tubular connecting means, such as connectors and/or prostheses, for accomplishing anastomoses by suturing them to the severed ends of tubular structures by a tubular suturing device ejecting staples radially.

It is a still further object of this invention to provide tubular connecting means, such as connectors and/or prostheses, for clinching the staples ejected radially by a tubular suturing device for suturing them to the ends of tubular structures.

It is a still further object of this invention to provide methods for clinching staples by the walls of tubular connecting means, such as connectors and/or prostheses, comprising a substantially rigid portion and a substantially soft and tensile resistant portion.

It is a still further object of this invention to provide a method for clinching of ejected staples without an anvil.

It is a still further object of this invention to provide artificial prostheses for accomplishing anastomoses by coupling them to tubular connectors sutured to the ends of tubular structures by tubular suturing device ejecting staples in approximately radial direction.

It is a still further object of this invention to provide a method for accomplishing anastomoses of tubular structures sutured with connectors at their ends by coupling them to artificial prostheses with preattached matching connectors.

It is a still further object of this invention to provide a method for implantation of total natural or artificial hearts, by suturing of tubular connecting means to the vessel origins with a tubular suturing device ejecting staples radially.

It is a still further object of this invention to provide a method for implantation of a left ventricular assist device in place of a portion of the thoracoabdominal aorta by attachments of tubular connecting means to the severed vessel ends by a tubular suturing device ejecting staples radially.

These objects, and others are achieved in a tubular suturing device with a rigid body comprising multiple receptacles arranged radially along the suturing surface of the body. Multiple staples are disposed within the receptacles. They are ejected out of the body by actuating means, which force them in approximately radial direction. The ejected staples attach tubular connecting means to the external or internal surface of tubular structures. The tubular connecting means, such as connector or prostheses, comprise an inner and an outer tubular portions affixed to each other, one of which is a substantially rigid portion with a predetermined coupling surface and the other is a substantially soft portion having sufficient tensile strength to withhold clinched staples. The device in the various embodiments can be implemented to accomplish suturing by ejecting a single or multiple rows of staples in inward or outward radial directions to the walls of tubular structures with various configurations, such as cylindrical, ovoid, ellipsoid or the like forms, and which are with constant or changing lumen. Tubular structures conducting high pressure fluids, such as blood vessels, are securely anastomosed in new methods, and new types of operative interventions are performed.

A better understanding of the present invention, along with its many attendant objects and advantages, may be obtained from consideration of the following detailed description of the preferred embodiments, particularly when read in conjunction with the appended drawings, a brief description of which follows:

BRIEF DESCRIPTION OF THE DRAWINGS

FIGS. 14A through 14G are perspective top-side views of the parts of another embodiment of the tubular suturing device ejecting staples radially in outward direction by another types of actuating elements, showing: (A) the whole device; (B) a cross-cut half of the body of the device; (C) a central rod for coupling with a driving-supporting mechanism and for supporting the movement of actuating elements; (D) the actuating elements; (E) the cross-cut half of the body combined with the central rod and the actuating elements; (F) means for coupling the device to the driving-supporting mechanism; (G) the whole device coupled to the front end of the driving-supporting mechanism.

FIGS. 15A and 15B show a staple abutted to a plunger in perspective top and side views respectively.

FIGS. 16A and 16B are perspective top views showing two rows of staples and plungers in basic and end-ejecting positions respectively.

FIGS. 17A and 17B are schematic front views in basic and end-ejecting positions respectively, illustrating the driving of the plunger and the staple by the actuating elements.

FIGS. 18A and 18B are perspective side-top views of the device shown with cross-cut half of the body and coupled to a driving-supporting mechanism, illustrating the movement of the actuating elements and staples in basic and end-ejecting positions respectively.

FIGS. 21A through 20E are perspective side-top views of another embodiment of the tubular suturing device for ejecting staples radially in inward direction showing: (A) the body of the device approximated to the front end of driving-supporting mechanism; the actuating elements and staples in basic position (B), and in end-ejecting position (C); the body coupled to the front end of the driving-supporting mechanism with actuating elements and staples in basic position (D), and in end-ejecting position (E).

FIG. 43 is a perspective view of the tubular suturing device shown in FIGS. 14A through 18B in operative engagement with a driving-supporting mechanism.

FIG. 44 is a perspective view of the driving and supporting elements of the driving-supporting mechanism.

FIG. 45 is a perspective view of the tubular suturing device coupled to the driving-supporting mechanism, a clamped blood vessel, and an external tubular connector.

FIG. 50 is a perspective view of the tubular suturing device from FIGS. 1A through 4B in operative engagement with another type of driving-supporting mechanism, an external connector, a holding instrument, and a clamped blood vessel.

FIGS. 52A and 52B illustrate first and second internal tubular connectors with correspondingly matching surfaces, in schematic front and perspective front-side views respectively.

FIGS. 53A and 53B illustrate the elements of the first internal connector in schematic front and perspective front-side views respectively.

FIGS. 54A and 54B illustrate the elements of the second internal connector in schematic front and perspective front-side views.

FIG. 55 is a perspective view of two blood vessels approached axially to the two internal connectors.

FIG. 56 is a perspective view showing the two internal connectors introduced into the ends of the two vessels and sutured to them by staples ejected in inward radial direction.

FIGS. 57A through 57C illustrate the two vessels anastomosed by the coupled internal connectors attached to their ends, showing them in perspective front-side, schematic front, and perspective front views respectively.

FIG. 58 is a schematic front view of a tubular prosthesis with rigid ends for coupling with the internal connectors.

FIGS. 59A and 59B illustrate in front-side perspective views the two blood vessels attached with the internal tubular connectors approached and coupled to the tubular prosthesis.

DESCRIPTION OF THE PREFERRED EMBODIMENTS

Figure 1A:
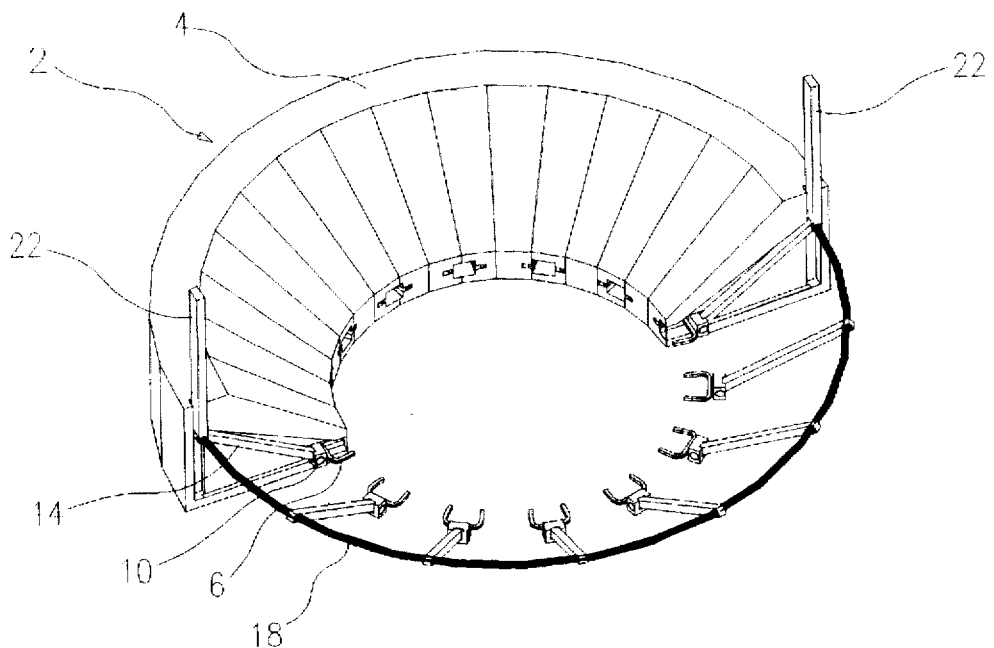
FIGS. 1A and 1B are perspective top-front-side views of a tubular suturing device for ejecting staples radially in inward direction, which shown with a removed cross-cut half of the body of the device, illustrating its elements in basic and end-ejecting positions respectively.

According to the present invention, I have developed a tubular suturing device ejecting staples in approximately radial direction for anastomosing of tubular structures without changing their lumen and natural configuration by suturing tubular connecting means to their ends.

Referring now to the drawings, FIGS. 1A through 4B illustrate a tubular suturing device for ejecting simultaneously multiple staples in inward radial direction.

Figure 1B:
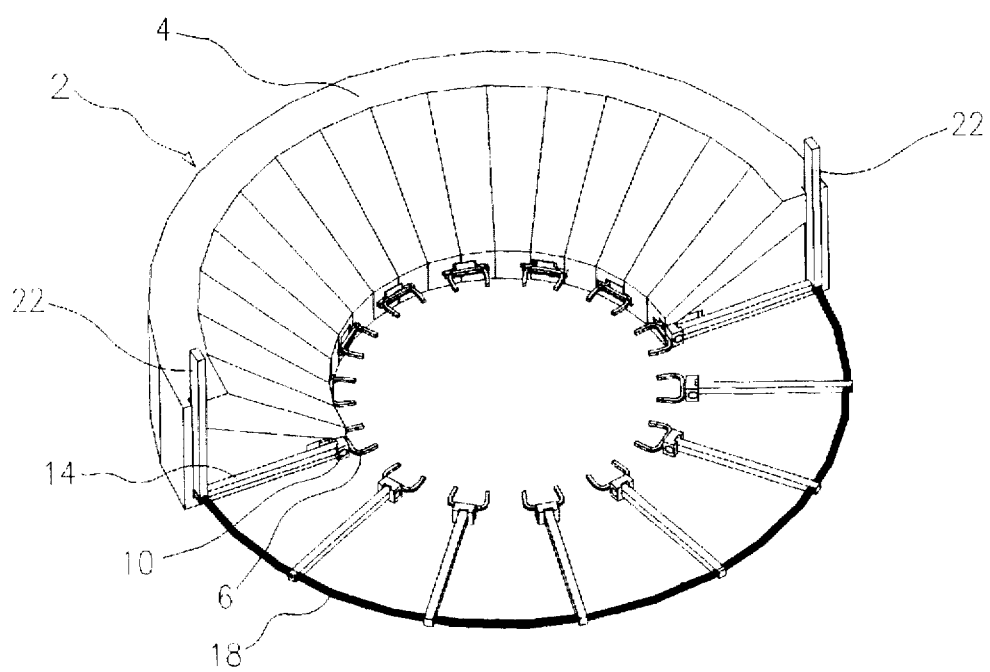

The tubular suturing device 2 is illustrated for better visualization with a removed halfcross-cut portion of the body in basic position in FIG. 1A and in end-ejecting position in FIG. 1B. The device comprises a rigid body 4 with a ring shaped form, produced from a hard rigid material such as metals, metal alloys, or any suitable the like material. Multiple staples 6 are arranged within multiple receptacles 8 spaced apart along the suturing surface of the body. Multiple plungers 10 sliding in plunger-retaining spaces 12 are abutted to the staples 6. The plungers 12 are actuated to move by multiple beveled levers 14 moving within beveled-lever recesses 16. The beveled levers 14 are pivotally coupled with first ends to a rigid ring 18, and with second ends to the plungers 10. The ring 18 moves in axial direction within a ring groove 20. It is affixed to the ends of two pushing members 22, such as straight bars or rods, which are positioned and moving axially in pushing retaining spaces 24.

The combination of two pushing members 22 affixed to a rigid ring 18, as shown throughout the application, can be executed in other configurations as well. Only one, or more than two pushing members can be employed with the same effect. The pushing members and the ring can have the combined form of a hollow cylinder, as the beveled levers are joined to its rim. The configuration of two pushing members affixed to a rigid ring is preferably preferred, as it produces a stable uniform force to all of the actuating means, while at the same time, it also allows a good view and enables precise manipulation of the inner positioned structures.

Figure 2A:
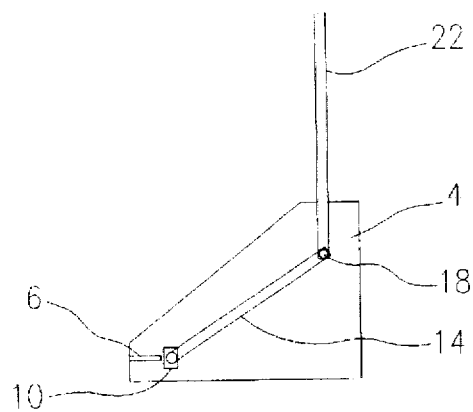
FIGS. 2A and 2B are schematic front views through the body of the device illustrating its actuating elements and staples in basic and end-ejecting positions respectively.
Figure 2B:
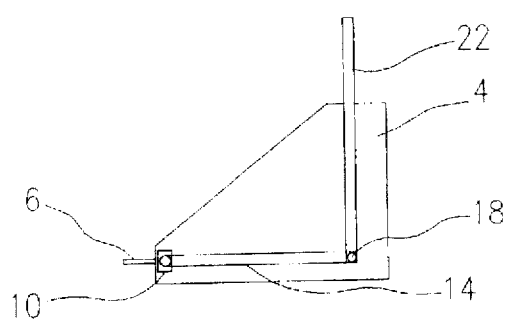

In operative action of the tubular suturing device 2, a pressure applied on the pushing members 22 moves them down in axial direction, as seen in FIGS. 2A and 2B. By rigid ring 18 affixed to them, this produces axial movement of the first ends of the beveled levers 14, which are coupled to the ring. The movement of the second ends of the beveled levers 14 is restricted in radial direction by the lever recesses 16. In this way, the beveled levers 14 transform the single axial movement of the ring 18 into multiple uniform radially directed movements. Sliding of the second ends of the beveled levers is further transmitted in radial direction by plungers 10 to staples 6 driving them forcefully out of the receptacles 8. The second ends of the beveled levers could exert force directly on the staples without plungers. Implementation of plungers is preferable to achieve smooth sliding of the second ends of the beveled levers and precise abutment with the staples.

Figure 3A:
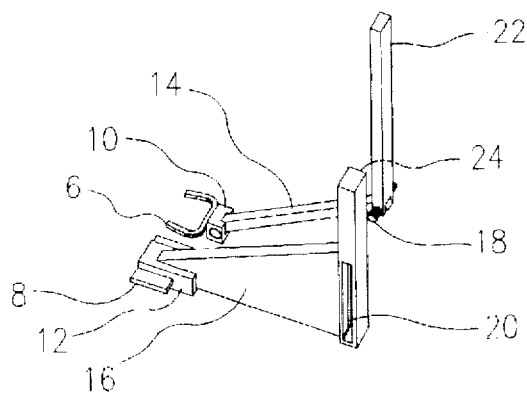
FIGS. 3A and 3B are perspective top-front-outer partial views of the retaining spaces and grooves of the device in relation to the actuating elements and staples, which are illustrated taken out and adjacent to the retaining spaces and grooves, showing them in basic and end-ejecting positions respectively.
Figure 3B:
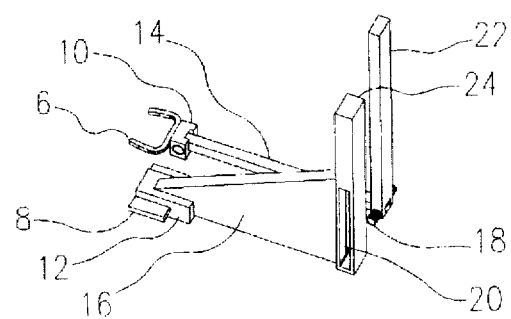
Figure 4A:
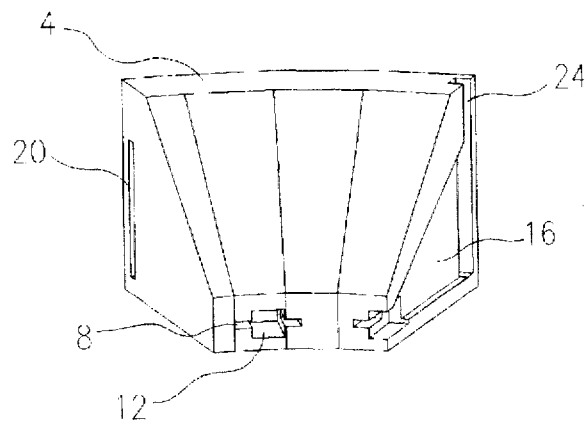
FIGS. 4A and 4B are perspective inner top-side and top-side-front views of a portion of the body of the device illustrating the retaining spaces and grooves of the actuating elements and staples.
Figure 4B:
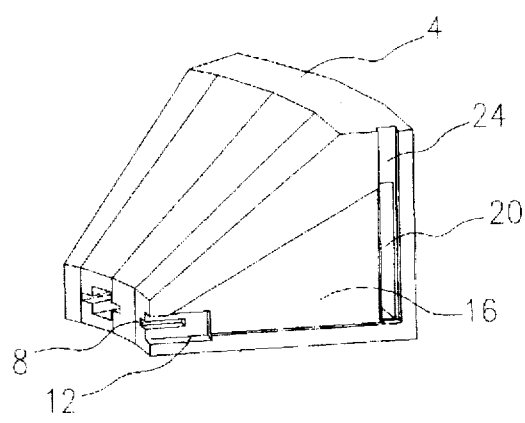

The actuating elements and staples move in direction predetermined by their respective retaining spaces, grooves, and receptacles, which is illustrated in FIGS. 3A and 3B. For better visualization, the staples and the actuating elements are shown out and adjacent to the spaces containing them. Only the retaining spaces, grooves and receptacles are illustrated in a portion of the body of the device in perspective views in FIGS. 4A and 4B. Pushing retaining spaces 24 and the ring groove 20 restrict and guide accordingly the movements of pushing members 22 and ring 18 in axial direction. Beveled-lever recesses 16 restrict and guide the movements of the beveled levers producing sliding movements of their second ends in inward radial direction. Plungers 10 are sliding radially within plunger-retaining spaces 12. They transmit the force to staples 6 driving them out of the body in radial direction, as directed by the staple receptacles 8.

The mechanism for exerting a driving force on the pushing members and for supporting the body in a stable position is not a particular subject of the present invention. It can be produced by a variety of already known ways employing hand or automated force, such as those utilized in gastrointestinal stapling devices, or in other suitable ways, some of which are described further on.

Various different embodiments of the tubular suturing device can be made by modifying some of its elements. Several such embodiments are illustrated in the following FIGS. 5A through 11.

Figure 5A:
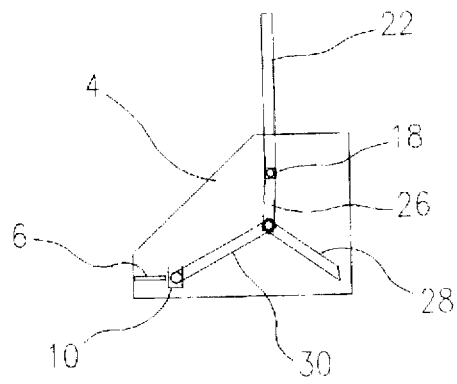
FIGS. 5A and 5B are schematic front sectional views of the body of another embodiment of the tubular suturing device effecting a stapling action by actuating means comprising multiple beveled levers, illustrating it in basic and end-ejecting positions respectively.
Figure 5B:
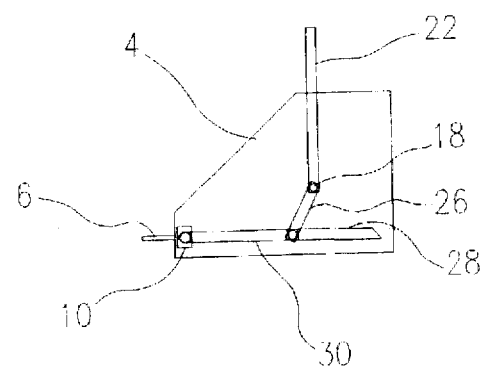

A tubular suturing device with different types of beveled levers is illustrated schematically in front view in FIGS. 5A and 5B, showing its actuating elements in basic and end-ejecting positions respectively. The force of the pushing member 22 by the ring 18 is transmitted to an actuating system comprising three levers 26, 28, and 30. The three levers are joined with the first of their ends in a star-like configuration. The second end of the lever 26 is pivotally coupled to the ring 18. Movement of the second end of lever 28 is restricted to a turning motion along its end point. The second end of the lever 30 is directed to slide in radial direction. By the plunger 10, the radial force is further transmitted to the staple 6 driving it forcefully out of the body 4. In this embodiment, the ejection of the staples is accomplished by shorter axial movement of the pushing members, as compared to the tubular suturing device of the previous embodiment.

Figure 6:
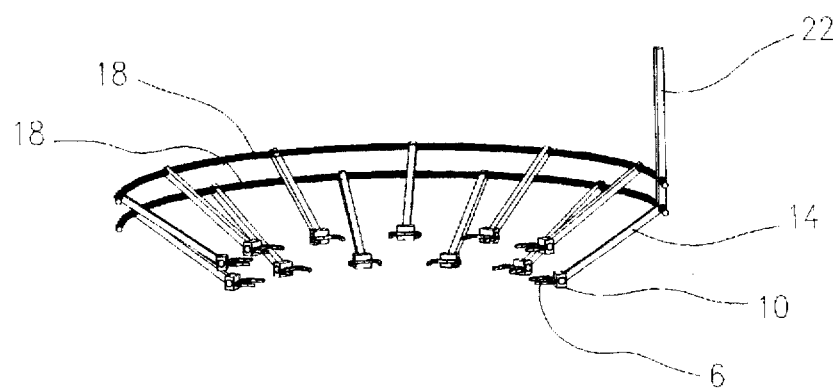
FIG. 6 is a perspective top-front view of a portion of another embodiment of the tubular suturing device for effecting simultaneous ejection of two rows of staples, showing only the actuating elements and the staples.

The tubular suturing device can be easily modified to apply simultaneously more than one row of staples. The actuating elements of such device are shown in FIG. 6. Instead of one, two rigid rings 18 are affixed to the pushing member 22. The movement of the two rings 18 is further transmitted by two rows of multiple beveled levers 14 and plungers 10 to two rows of staples 6. In this way, an axial movement of the pushing members produces simultaneous ejection of two rows of staples. In the same manner, devices ejecting three or more rows of staples can be constructed.

Figure 7:
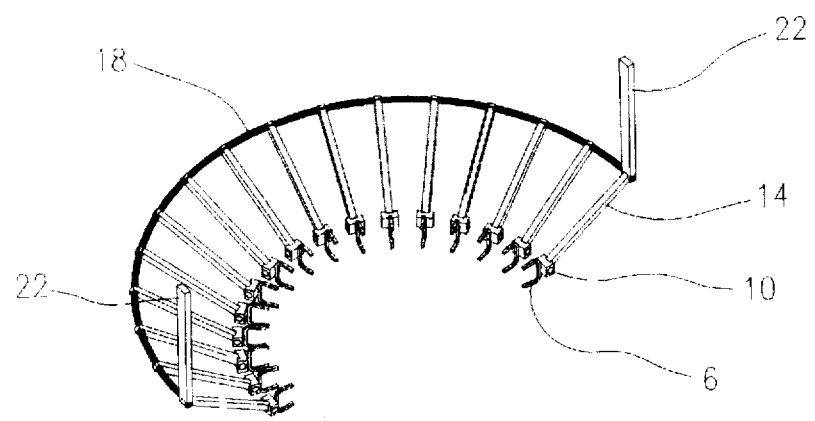
FIG. 7 is a perspective top-side view of a portion of another embodiment of the tubular suturing device for placement of perpendicularly oriented staples in a radial direction, illustrating only the staples and the actuating elements.

Suture lines with a high density of staples can be effected by a tubular suturing device ejecting perpendicularly oriented staples (perpendicular in terms, that the planes of the staples are perpendicular to the cutting plane of the severed tubular organ). A tubular suturing device of this type is shown in FIG. 7. Only pushing members 22, ring 18, beveled levers 14, plungers 10, and staples 6 are illustrated. As seen, much more beveled levers and plungers are needed to actuate the increased number of staples.

Figure 8A:
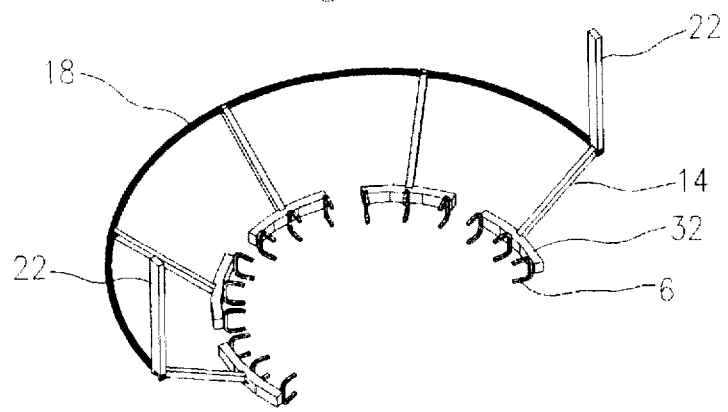
FIGS. 8A and 8B are perspective top-side views of another embodiment of the tubular suturing device comprising actuating elements driving multiple staples, showing it in basic and end-ejecting positions respectively.
Figure 8B:
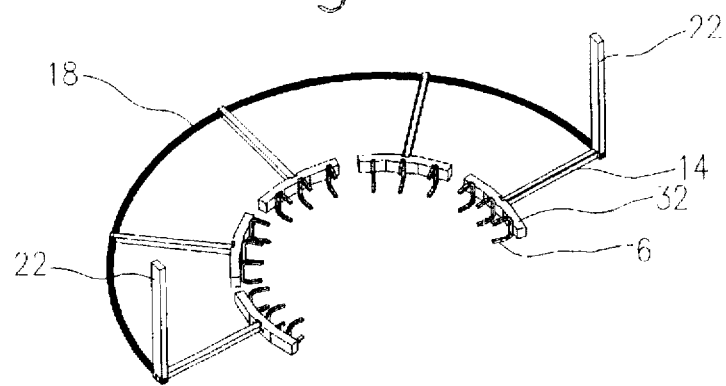

A suturing device with reduced numbers of beveled levers and plunges for applying dense suture lines is shown in FIGS. 8A and 8B in basic and end-ejecting positions respectively. In this embodiment, each of the beveled levers 14 is coupled to arcuately extended plungers 32. Each plunger 32 is abutted to three staples 6. As illustrated, fifteen staples 6 are actuated by five beveled levers 14 and five plungers 32. This substantially simplifies the construction of the device.

Figure 9:
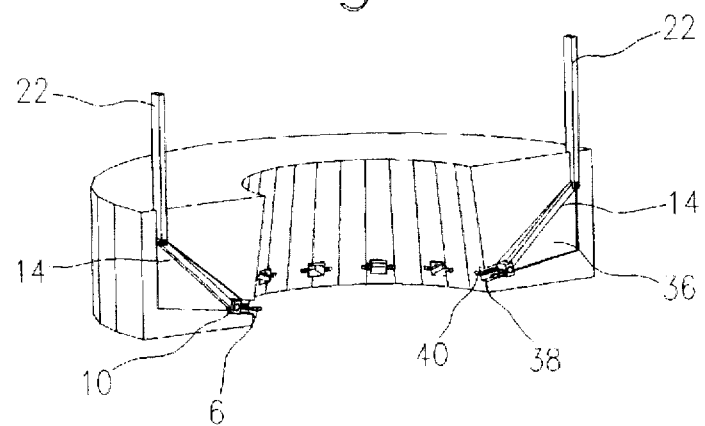
FIG. 9 is a perspective front-side-top view of another embodiment of the tubular suturing device with a conical stapling surface, shown with a removed cross-cut half of the body of the device.

By changing the plane of the retaining spaces, recesses and receptacles which direct the movement of the actuating means and staples, suturing action can be performed to structures with various tubular configurations. A tubular suturing device for implementation with tubular organs having cut-conical configuration is shown in FIG. 9. The device has a rigid body 34 with a cut-conical inner suturing surface. In the already described manner, two pushing members 22 transmit the actuating movement by ring 18, beveled levers 14, and plungers 10 to staples 6 ejecting them out of the body. Beveled-lever recesses 36, plunger-retaining spaces 38, and staple receptacles 40, which are directing the movements of the actuating elements and staples, are oriented perpendicularly to the cut-conical suturing surface of the body 34. The device can find application for suturing tubular structures with changing diameter, such as blood vessels enlarging in the areas of branching or entering major organs.

Figure 10A:
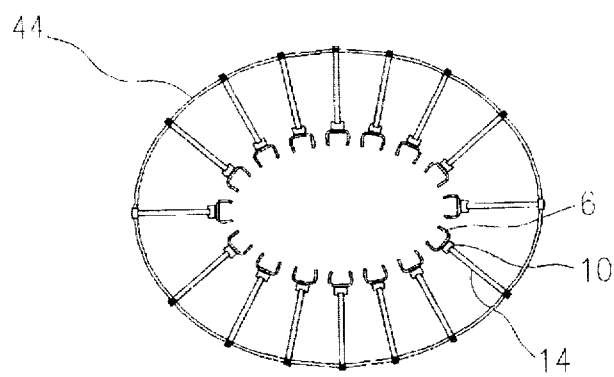
FIGS. 10A and 10B are perspective illustrations of another embodiment of the tubular suturing device with an ellipsoid stapling surface, showing respectively the actuating elements and staples in a top view, and the device with a removed cross-cut half of the body in a top-front-side view.
Figure 10B:
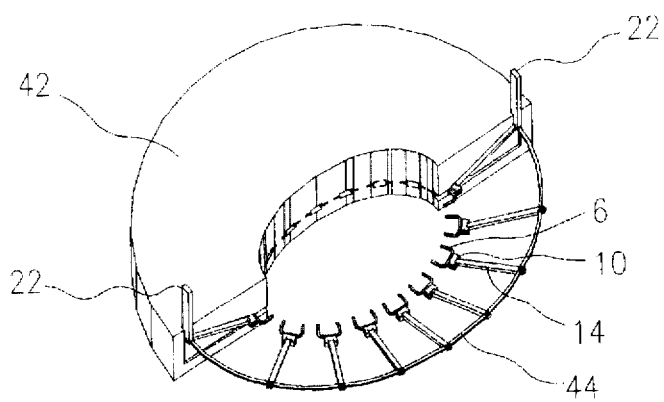

Tubular organs are not always strictly cylindrical within the living organism. Large veins are less rigid than arteries. They are flattened and their natural form is more ovoid or ellipsoid than strictly cylindrical. Preserving the natural anatomical configuration of anastomosed structures is always preferable for optimal results. A tubular suturing device for applying suture lines to ellipsoid structures is shown in FIGS. 10A and 10B. The actuating elements are shown in a top view in FIG. 10A. The device, with a removed cross-cut half of the body is shown in a perspective side-top view in FIG. 10B. The ring-shaped body 42 of the device has an ellipsoid suturing surface. The driving force of the pushing members 22 is transmitted to ellipsoid ring 44 affixed to them. The ring 44 further transmits the force by multiple beveled levers 14 and plungers 10 in approximately radial direction to staples 6. In this way, the ellipsoid ring transforms the axial motion into multiple approximately radial forces directed perpendicularly to the ellipsoid suturing surface.

The different embodiments of the tubular suturing device described above demonstrate various additional features which can be achieved by modifying some of the elements. These modifications can be implemented alone or in combinations, so devices with various combinations of these features can be constructed. The illustrated modifications are typical not only for the embodiments described above. In a similar manner, they can be implemented alone or in combination in all of the embodiments of the tubular suturing device depicted throughout the patent application.

Figure 11:
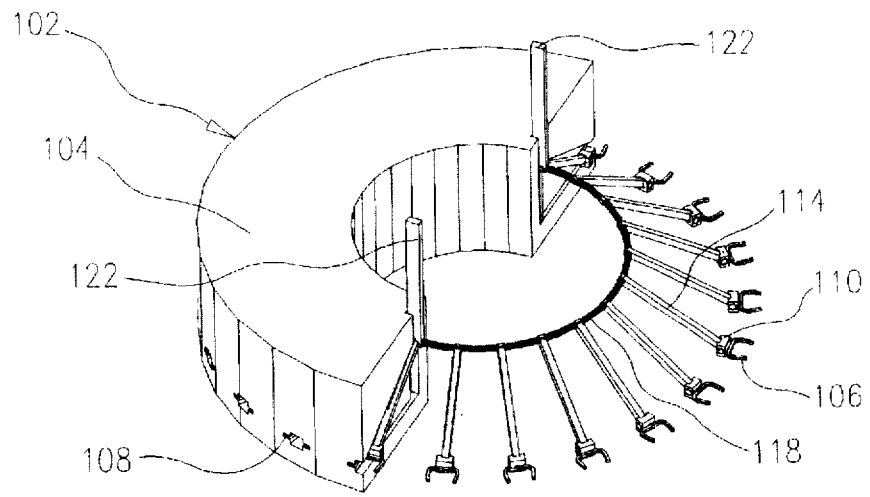
FIG. 11 is a perspective top-side view of another embodiment of the tubular suturing device for ejecting staples in outward radial direction, shown with a removed cross-cut half of the body.

Another embodiment of the tubular suturing device 102 is shown in a perspective view in FIG. 11 with a removed cross-cut half of the body 104. The device operates on similar principle, but it ejects staples in outward radial direction. Multiple staples 106 are positioned within spaced apart receptacles 108 arranged radially along the suturing surface of rigid body 104 with outer tubular form. Abutted to the staples 106 are multiple plungers 110 situated within plunger-retaining spaces 112. Multiple beveled levers 114 positioned within beveled recesses 116 are pivotally coupled with the first ends to a rigid ring 118 and with the second ends to the plungers 110. The rigid ring 118 positioned in ring groove 120 is affixed to ends of pushing members 122 moving in pushing retaining spaces 124. Applied force on the pushing members 122 moves them and the ring attached to them 118 in axial direction downward. The axial movement is transformed and transmitted by the multiple beveled levers 114 into multiple radial movements of their second ends in outward radial direction. By the plungers 110, the radial forces are further transmitted to the multiple staples 106 driving them forcefully out of the tubular suturing device 102.

Another embodiment oft he tubular suturing device for ejecting staples in an outward radial direction is shown in perspective view is FIGS. 12A through 12F. The suturing device 202 consists of a rigid body 204 comprising a lower flat cylindrical portion 204a and an upper tubular portion 204b. Multiple staples 206 disposed within staple receptacles 208 are arranged radially along the outer surface of the lower portion 204a. The staples 206 are abutted to plungers 210 moving within predefined plunger-retaining spaces 212. A rigid ring 218 is affixed to protrusions 220 extending inwardly of the upper side of the tubular portion 214b. Multiple angular levers 214 are coupled pivotally to the ring 218. The levers 214 comprise two approximately perpendicular arms 214a and 214b. They are coupled pivotally in the area of angulation to the rigid ring 218. The lower ends of arms 214b move in predefined passages 216 of the lower portion 204a of the body 204. The ends of the arms 214b are coupled pivotally to the plungers 210. The body 204 of the device 202 couples to a central rod 222 and an outwardly flanged pushing cylinder 228 positioned over the rod, which are parts of a driving-supporting mechanism not shown here. The central rod 222 is introduced through a hole 224 of the lower portion 204a and firmly secured to the body 204 by a nut 226. The lower side of the pushing cylinder 228 contacts the upper sides of the arms 214a of the angular levers 214.

Figure 12A:
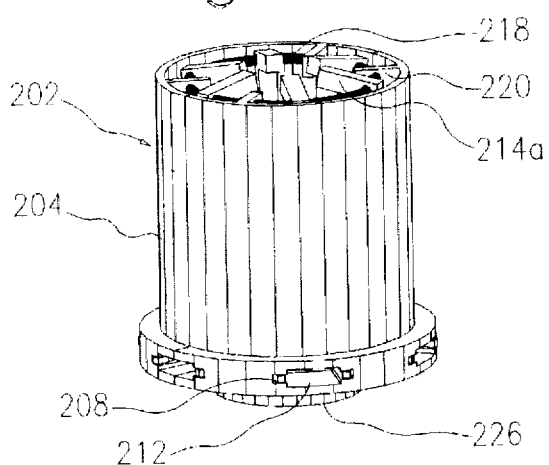
FIGS. 12A through 12F are perspective top-side views of the parts of another embodiment of the tubular suturing device ejecting staples radially in outward direction, showing: (A) the whole device; (B) a cross-cut half of the body of the device; (C) the actuating elements and staples; (D) the cross-cut half of the body coupled to the front end of a driving-supporting mechanism; the actuating elements and staples within a cross-cut half of the body coupled to the driving-supporting mechanism in basic position (E), and in end-ejecting position (F).
Figure 12B:
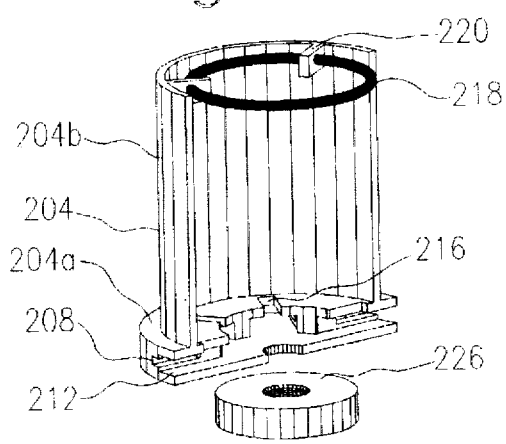
Figure 12C:
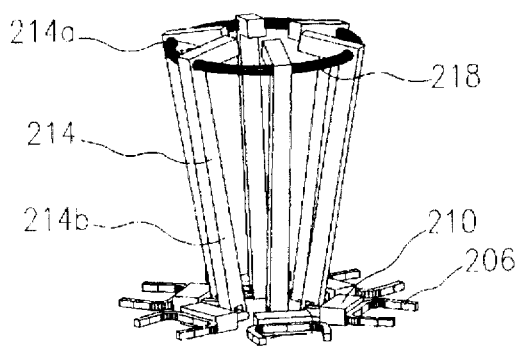
Figure 12D:
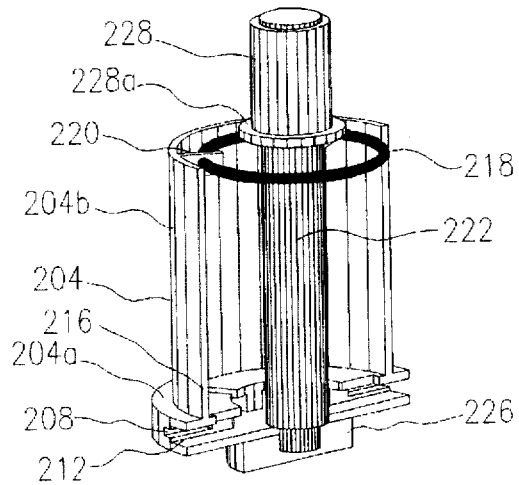
Figure 12E:
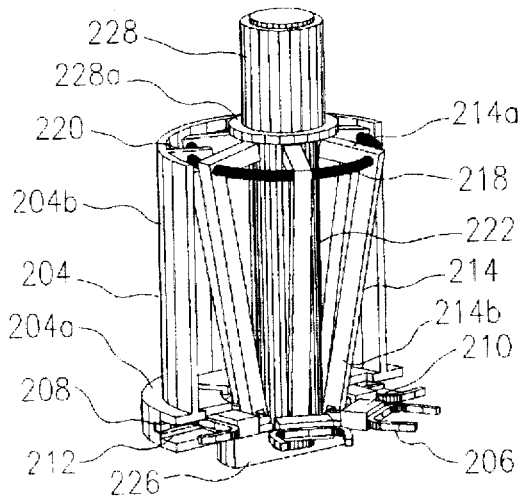
Figure 12F:
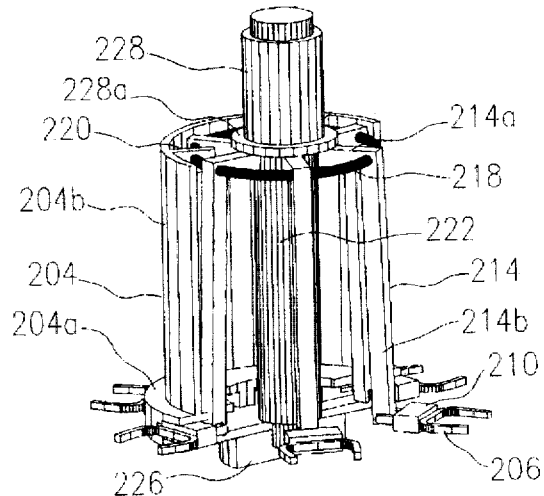
Figure 13A:
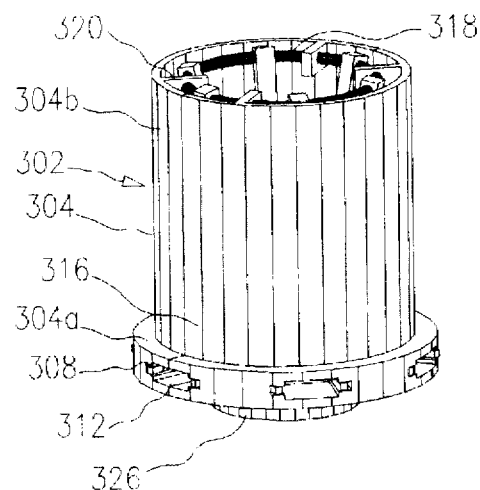
FIGS. 13A through 13B are perspective top-side views of the parts of another embodiment of the tubular suturing device ejecting staples radially in outward direction by another type of actuating means, showing: (A) the whole device; (B) the actuating elements and staples; the actuating elements and staples within cross-cut half of the body coupled to the front end of a driving-supporting mechanism in basic position (C), and in end-ejecting position (D).
Figure 13B:
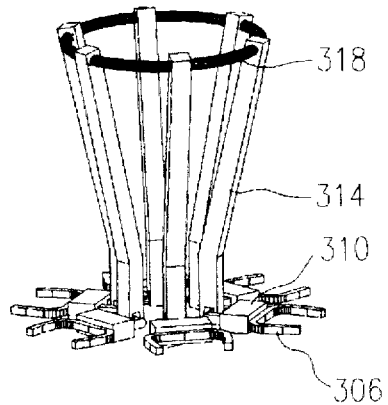
Figure 13C:
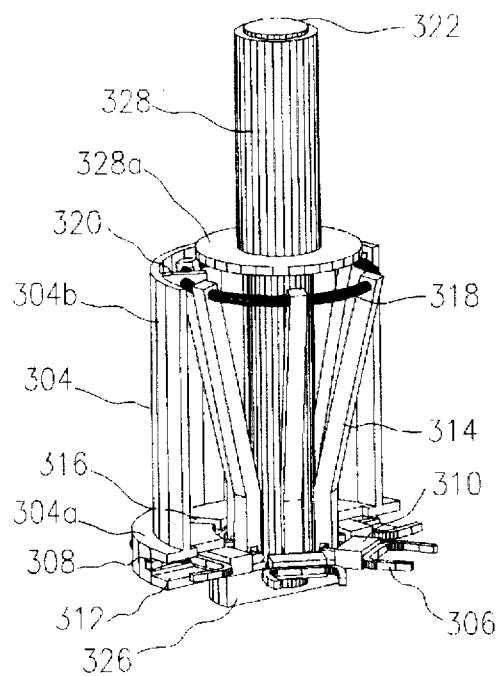
Figure 13D:
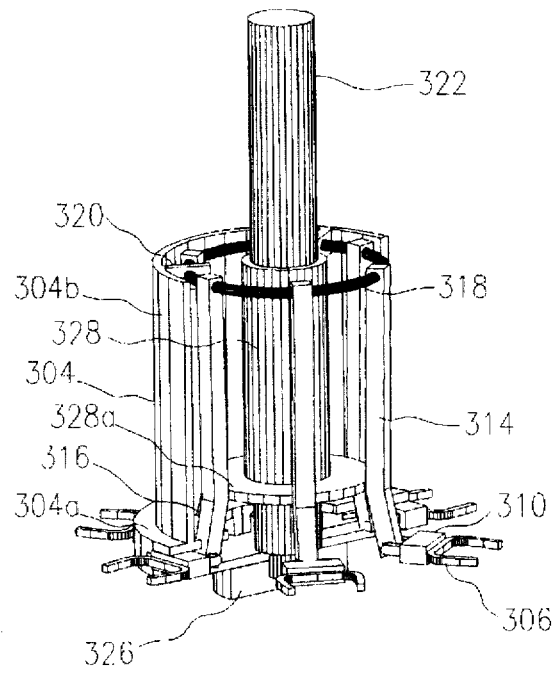
Figure 19A:
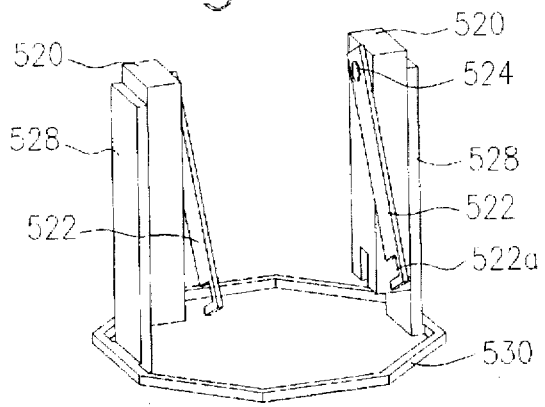
FIGS. 19A through 19D are perspective side-top views of another embodiment of the tubular suturing device for ejecting staples radially in inward direction, showing: (A) the body of the device approximated to the front end of driving-supporting mechanism; (B) the actuating elements and staples; the body with the actuating elements and staples coupled to the front end of the driving-supporting mechanism in basic position (C), and in end-ejecting position (D).
Figure 19B:
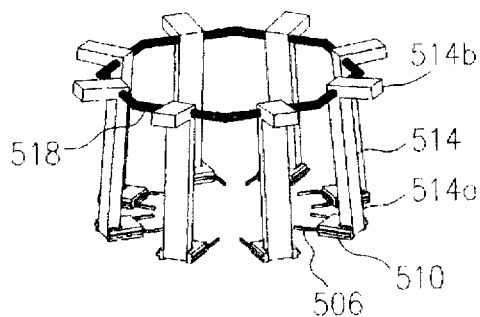
Figure 19C:
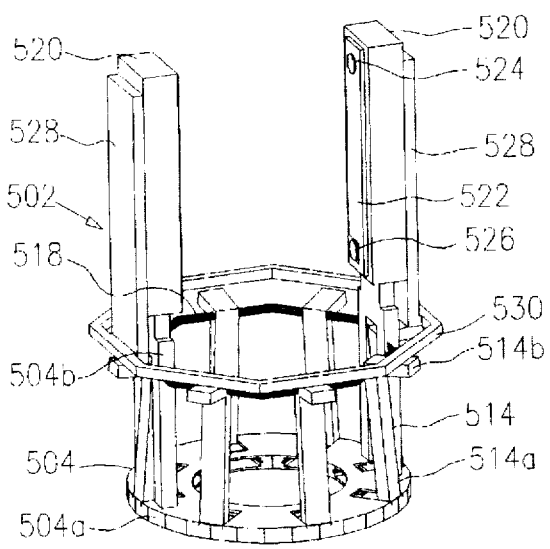
Figure 19D:
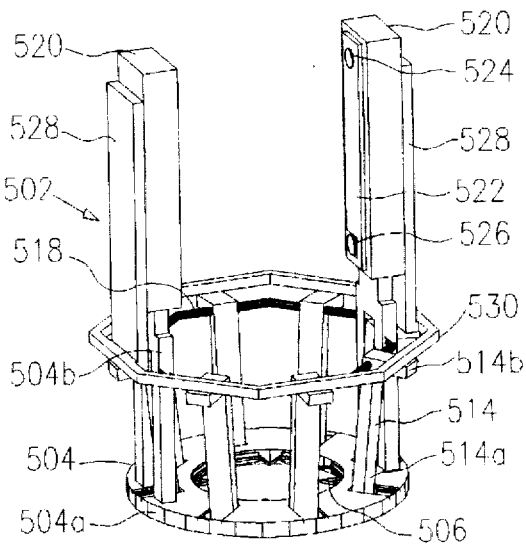
Figure 20A:
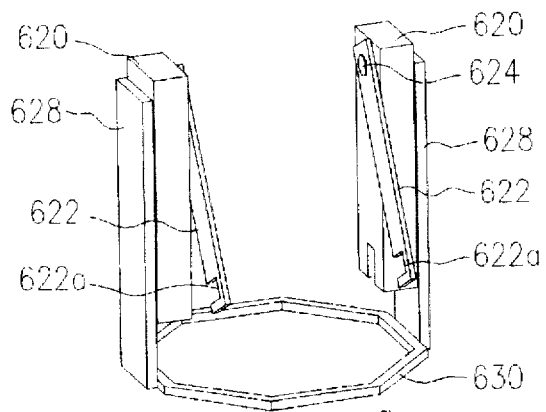
FIGS. 20A through 20D are perspective side-top views of another embodiment of the tubular suturing device for ejecting staples radially in inward direction showing: (A) the body of the device approximated to the front end of a driving-supporting mechanism; (B) the actuating elements and staples; the body with the actuating elements and staples coupled to the front end of the driving-supporting mechanism in basic position (C), and in end-ejecting position (D).
Figure 20B:
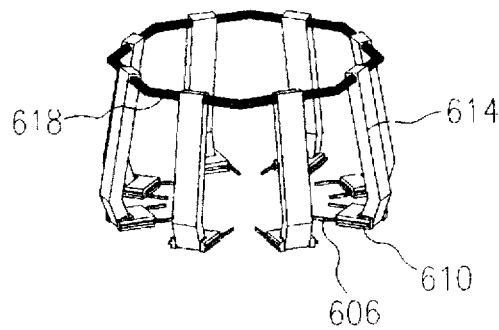
Figure 20C:
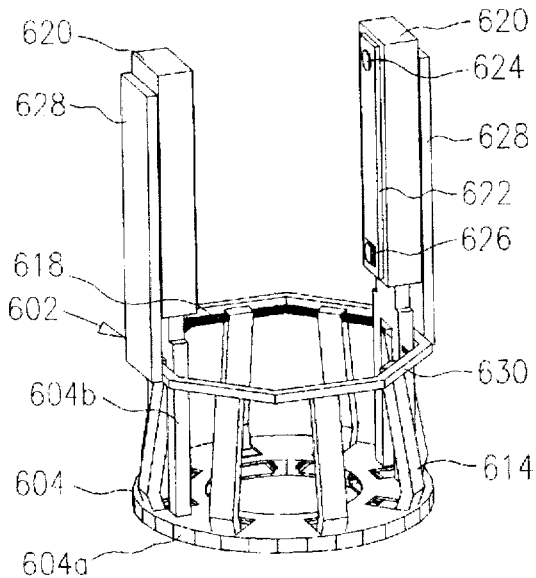
Figure 20D:
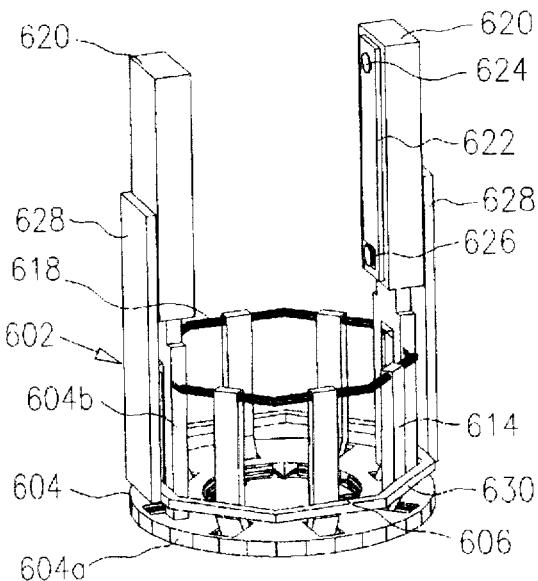
Figure 21A:
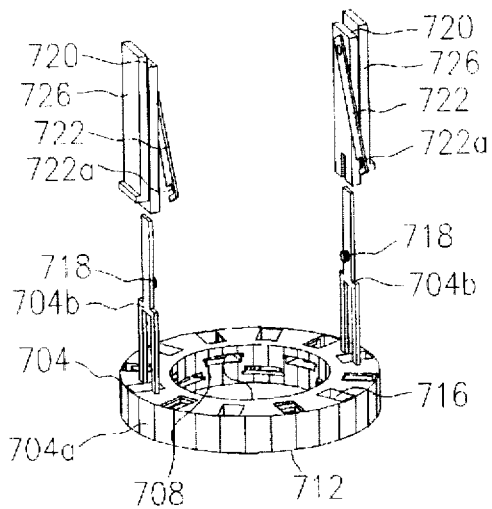
Figure 21B:
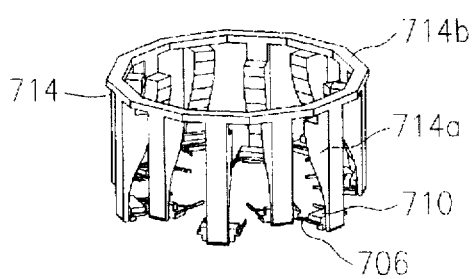
Figure 21C:
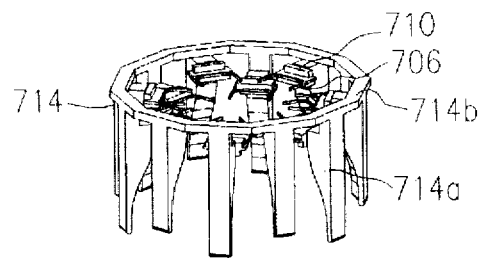
Figure 21D:
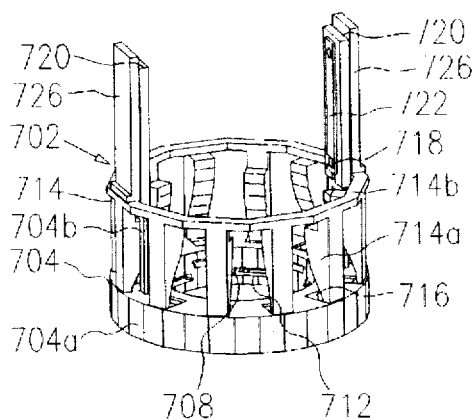
Figure 21E:
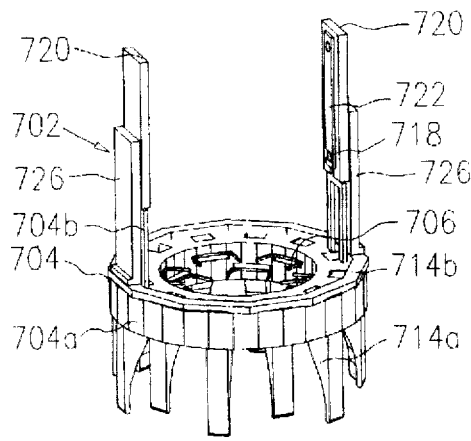

The operative action of the suturing device is best seen in FIGS. 12E and 12F. The pushing cylinder 226 is pressed to slide axially downward over the central rod 222. The flanged lower end of the pushing cylinder 226 exerts pressure on the arms 214a of the multiple angular levers 214. The angular levers 214 turn around the axis of the rigid ring 218. This produces movements of the lower ends of the arms 214b in approximately outward radial direction. By the coupled to them plungers 210, they drive forcefully the staples 206 out of the receptacles 208 in outward radial direction.

Another embodiment of tubular suturing device for ejecting staples in outward radial direction operating on comparable principle is shown in perspective views in FIGS. 13A through 13D. The suturing device 302 consists of similar elements as in the last embodiment: rigid body 304 comprising lower flat-cylindrical portion 304a and upper tubular portion 304b; multiple staples 306 disposed within receptacles 308 along the outer suturing surface of the body; plungers 310 abutted to the staples 306 and moving slidably within plunger-retaining spaces 312; rigid ring 318 affixed by protrusions 320 extending inwardly of the upper end of the upper tubular portion 304b; and nut 226 which by central rod 322 couples the body 204 to a driving-supporting mechanism. Multiple levers 314 running axially and slightly inclined in inward direction are coupled pivotally with first ends to the rigid ring 318. Their second ends are moving in passages 316 and are coupled to plungers 310. Hollow pushing cylinder 328 having outwardly flanged lower end 328a is positioned over the central rod 322. It is with a predetermined outer diameter to approach the inner sides of levers 314.

In operative action, the pushing cylinder 328 is pressed down to slide axially downward over the central rod 322. The flanged end 328a of the pushing cylinder exerts pressure on the inner sides of the multiple levers 314. The levers 314 turn around the axis of the rigid ring 318. Their second ends move outwardly in approximately radial direction. By plungers 310, they eject forcefully staples 306 of the body 304 of the device 302. A longer axial movement of the pushing cylinder is needed to actuate the staples in this case, as compared to the device of the previous embodiment with angular levers.

Another embodiment of the tubular suturing device for ejecting two rows of staples in outward radial direction is shown in FIGS. 14A through 18B. The drawings are multiple times magnified views of a suturing device, which has an actual size of approximately five-six millimeters, so some of the elements seem out of proportion. The rigid body 404 of the device comprise a flat cylindrical portion 404a and a hollow dome-like portion 404b. Two rows of multiple staples 406 are disposed within staple receptacles 408 arranged along the outer surface of the cylindrical portion 404a of the body. The staples 406 are abutted by two rows of plungers 410 positioned within plunger-retaining spaces 412. The lower end of a central axial rod 418 is affixed axially to the inner side of the dome-like portion 404b of the body 404. The upper end of the central rod 418 terminates in a rectangular bar portion 418a having two outward protrusions 426 for coupling with a driving-supporting mechanism. An actuator 414 is slidingly mounted over the central rod 418. The actuator 414 comprise a hollow cylindrical portion 414a, multiple rigid plates 414b having predefined sloped outer edges affixed radially to the external surface of cylindrical portion 414a, and preferably an outward flange 414c above the rigid plates 414b. The rigid plates 414b move in axial direction through passages 416 of the cylindrical portion 404a of the body 404.

Coupling of the tubular suturing device 402 to the front end of a driving-supporting mechanism is also illustrated. The bar portion 418a of the central rod 418 fits into a reciprocating space of supporting bar 420 of the driving-supporting mechanism. Latching mechanism 422, mining around spindle 424, locks by notches 425 with protrusions 426 of the bar portion of the central rod. In this way, the body of the device is attached to the front end of the driving-supporting mechanism. Two driving bars 428 of the driving-supporting mechanism with outwardly extended flat bases 428a are positioned on opposite sides of the supporting bar 420. The flat bases 428a contact with the upper surface of range 414c, transmitting the force of the driving bars 428 to the actuator 414.

The method of operation of the tubular suturing device 402 is illustrated in FIGS. 15A through 18B. A staple 406 comprising two approximately parallel pieces 406a joined by one cross piece 406 abutted to a plunger 410 is shown in FIGS. 15A and 15b in top and front views. The plunger preferably consists of two portions—outer portion 410a for abutment with the staple 406 and inner portion 410b for contacting with the actuator. The inner portion 410b is axially enlarged, so the plungers 410 are retained within the plunger-retaining spaces 412 and not ejected out of the body in the end of the stapling action. Two rows of staples and plungers are shown in top view FIGS. 16A and 16B in basic and end-ejecting position. As it can be seen, the ejecting of the staples in outward radial direction moves them away from each other, which is more expressed in devices with small caliber.

The ejection of staples 406 by actuator 414 out of the tubular suturing device is illustrated in partial schematic front views in FIG. 17A and 17B. The whole device, illustrated with a removed cross-cut half of the body, coupled to a driving-supporting mechanism is shown in perspective views in FIGS. 18A and 18B, in basic and end-ejecting positions respectively. A downward axial movement of the pushing bars 428 moves down the actuator 414 sliding it over the central rod 418. The outer edges of rigid plates 414b of the actuator 414 exert increasing pressure on the inner side of plungers 410, which pushes them outwardly. The plungers 410 slide in radial direction predetermined by the plunger-retaining spaces 412. They transmit the radial forces to the abutted staples 406 driving them forcefully out of the device.

The tubular suturing device described last is the preferable embodiment for ejecting staples in outward radial direction. The absence of pivoted or mining actuating means simplifies substantially its construction. This is especially important for manufacturing devices with small sizes. Regretfully, there is a limit for how small devices ejecting staples in outward radial direction can be produced. As it was shown, staples distance away from each other when they are ejected in outward radial direction. Furthermore, the prongs of the staples must have certain length necessary to pierce the walls of the blood vessel and the connector, and to be clinched. These factors are limitations for reducing the dimensions of the tubular suturing devices. The smallest possible suturing devices, ejecting staples in outward radial direction, are believed to be with a diameter of the suturing surface of approximately five–six millimeters.

Three embodiments of the tubular suturing device operating on similar principles to these of the last three embodiments, but for applying staples in inward radial direction, are described next.

Tubular suturing device 502 presented in FIGS. 19A through D has a rigid body 504 comprising a flat hollow cylindrical portion 504a and two forked bars 504b affixed to it in axial direction. A rigid ring 518 is affixed to the forked bars 504b at a distance parallel and above the cylindrical portion 504a. Multiple angular levers 514, comprising lower arms 514a and upper arms 514b affixed approximately perpendicularly, are mounted pivotally to the ring 518. The free ends of lower arms 514a couple to plungers 510 and move through passages 516 of the cylindrical portion 504a. The plungers 510 are moving in radial direction within plunger-retaining spaces 512. Multiple staples 506, abutted to the plungers 510, are positioned within staple receptacles 508 arranged radially along the inner surface of the cylindrical portion 504a of the body 504.

Means for coupling the tubular device with the front end of a driving-supporting mechanism are also shown. The upper ends of forked bars 504b fit into the reciprocating spaces of supporting bars 520, coupling the body of the device to the driving-supporting mechanism in this way. The attachment is secured in stable positions by latches 522 rotating around spindles 524 of the supporting bars 520. Notches 522a of the latches 522 lock around protrusions 526 of the forked bars 504b. Driving bars 528 are positioned adjacent to the supporting bars 520 on their outer sides. Driving ring 530 is affixed to their lower ends. The ring contacts the upper surfaces of the ends of upper arms 514b of the angular levers 514.

In operative action, a forced axial downward movement of the driving bars 528 and the ring 530 pushes down the ends of the upper arms 514b of the angular levers 514. The angular levers 514 rotate along the axis of the rigid ring 518. The ends of the lower arms 514a move in approximately inward radial direction. The radial forces are further transmitted by plungers 510 to staples 506 ejecting them out of receptacles 508.

Another embodiment of the tubular suturing device for ejecting staples in inward radial direction with comparable structure and method of operation is presented in FIGS. 20A through 20D. The suturing device 602 has a rigid body 604 comprising a flat hollow cylindrical portions 604a and two forked bars 694b affixed axially to it. A rigid ring 618 is affixed to the two forked bars parallel to and at a distance above the cylindrical portions 604a. Multiple pivoted levers 614 are hinged to the rigid ring 618 with their first ends. The pivoted levers 614 are with predefined configuration running axially and slightly inclined in outward radial direction. The second ends of the levers 614 are coupled to multiple plungers 610 and are moving through passages 616 of the cylindrical portion 614a. The plungers 610 move in radial direction within plunger-retaining spaces 612. Multiple staples 606 abutted to the plungers 610 are disposed within staple receptacles 608 arranged along the inner surface of the body 604.

The device attaches to the front end of driving-supporting mechanism in a similar manner as the last described embodiment. The body 604, by the upper ends of forked bars 604b, fits into reciprocating spaces of supporting bars 620. The connection is secured in stable positions by latches 622 rotating around spindles 624 of the supporting bars 620. Notches 622a of the latches lock 622 around protrusions 626 of the forked bars 604b. Driving bars 628 are positioned next to the supporting bars 620 on their outer sides. Driving ring 630 is affixed to their lower ends. The ring 630 contacts with the outer sides of the upper ends of the hinged levers 614.

The device is actuated to operate by forcing a downward axial movement of the driving levers 528 and accordingly of the driving ring 630. The driving ring 630 pushes the outer sides of the pivoted levers 614, causing the levers to turn inward along the axis of the rigid ring 618. The approximately radial movements of the second ends of the pivoted levers is transmitted by the plungers 610 to the staples 606 driving them forcefully out of their receptacles 606.

Another embodiment of the tubular suturing device for ejecting staples in inward radial direction is shown in FIGS. 21A through 21E. The device 702 has a rigid body 704 comprising a hollow flat cylindrical portion 704a and two forked bars 704b affixed axially to it. The body of the device is coupled to the front end of driving-supporting mechanism by the ends of forked bars 704b. Their ends fit into reciprocal spaces of supporting bars 720. The connection is secured by latches 722 rotating around spindles 724 of the supporting bars 720. By notches 722a, the latches 722 lock with protrusions 718 of forked bars 704b. Two driving bars 726 moving in axial direction are positioned on the outer side adjacent to the supporting bars 720.

Two rows of multiple staples 706 disposed within staple receptacles 708 are arranged along the inner surface of cylindrical portion 704a of the body 704. The staples 706 are abutted by plungers 710 moving within plunger-retaining spaces 712. The staples are driven in inward radial direction by an actuator 714. The actuator 714 comprises multiple rigid plates 714a, with predefined sloped inner sides, oriented radially and affixed with their upper sides to a rigid ring 714b.

In operative action, the driving bars 726 are pushed to move axially in downward direction. They move accordingly actuator 714 in downward direction. The inner sides of the rigid plates 714a exert pressure on the outer sides of the plungers 710 forcing them in inward radial direction. The plungers 710 transmit the forcing movements to the abutted staples 706 driving them out of the receptacles 706.

It should be noted, that most of the embodiments of the tubular suturing device have been described with only one row of staples in order to illustrate clearly their elements and methods of operations. In a similar manner as described above, all of them can be constructed to eject two, three or more rows of staples by adding additional rings, actuating means, and staples. For suturing organs conducting high pressure fluids (such as blood vessels), devices with at least two rows of staples should be implemented to assure secure fluid-tight connection of the anastomosed structures.

The described embodiments do not include an anvil for clinching of the staples as an integral part of their structure. New methods for clinching of staples by the walls of the sutured tubular connecting means are shown in the next FIGS. 22 through 28B.

Figure 22:
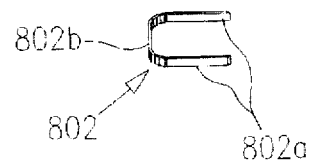
FIG. 22 is a perspective top-side view of a staple for application with the tubular suturing device.

A single staple 802 suitable for application with the tubular suturing device is shown in perspective view in FIG. 22. The staple comprise two parallel prongs 802a, whose ends are connected by a crosspiece 802b. The staple is made preferably of flattened belt-like wire to warrant clinching of the prongs in a coplanar plane.

Figure 23:
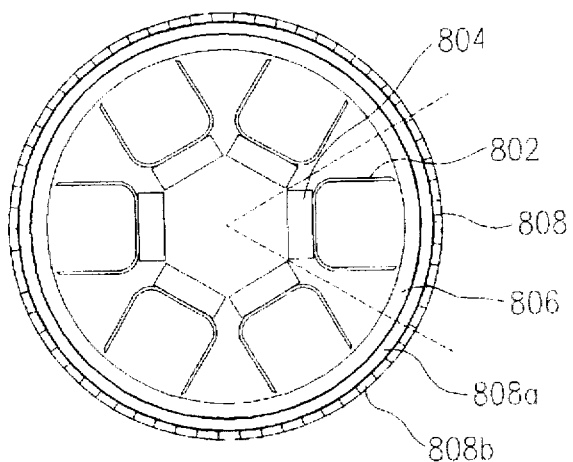
FIG. 23 is a perspective top view of multiple staples, a tubular organ, and an external tubular connector, shown in a basic position of stapling action in outward radial direction.

FIG. 23 is a top view of a row of multiple staples 802 and plungers 804 arranged radially, with the prongs 802a of the staples pointing outwardly. A hollow tubular organ, such as blood vessel 806, and an external tubular connector 808 are positioned externally to them. The various types of tubular connectors and prostheses for application with the tubular suturing device will be described in details further on. In general, the external connector 808 comprises an inner soft tubular portion 808a made of material substantially resistant to tension, and an outer substantially rigid tubular portion 808b.

Figure 24A:
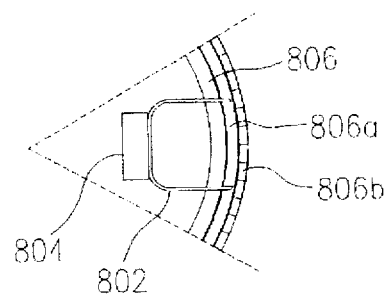
FIGS. 24A and 24B are perspective top views illustrating a method for clinching of staples ejected in outward radial direction for suturing the external tubular connector to the tubular organ, showing them in basic and end-ejecting positions respectively.
Figure 24B:
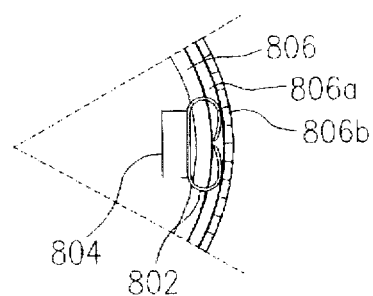
Figure 25A:
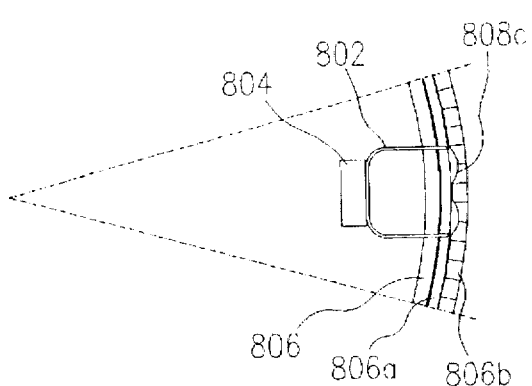
FIGS. 25A and 25B are perspective views illustrating another method for clinching of staples ejected in outward radial direction for suturing the external tubular connector to the tubular organ, showing them in basic and end-ejecting positions respectively.
Figure 25B:
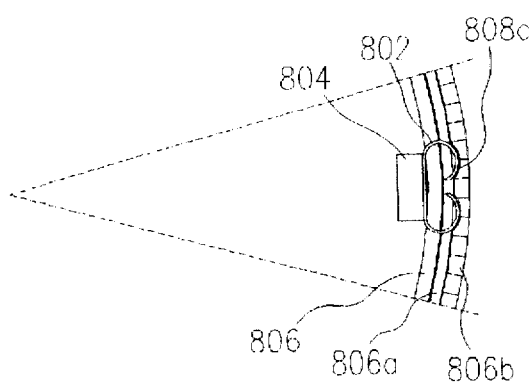
Figure 26:
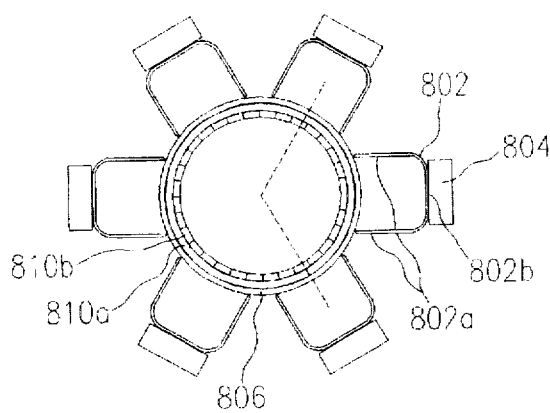
FIG. 26 is a perspective top view of staples, a tubular organ and an internal tubular connector, shown in a basic position of stapling action in inward radial direction.
Figure 27A:
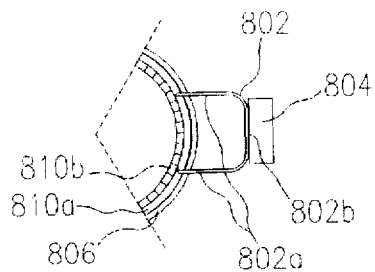
FIGS. 27A and 27B are perspective top views illustrating a method for clinching of staples ejected in inward radial direction for suturing the internal tubular connector to the tubular organ, showing them in basic and end-ejecting positions respectively.
Figure 27B:
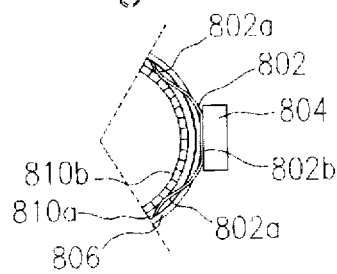

Methods for clinching of staples 802 ejected in outward radial direction for suturing the tubular connector 808 over the external surface of the tubular organ 806 are illustrated. A method for suturing organs with relatively small diameter is shown in FIGS. 24A and 24B, and a method for suturing larger organs is illustrated in FIGS. 25A and 25B. As seen, the walls of tubular organ and the connector with smaller diameters are more curved than the corresponding ones with larger diameters.

The ejected staples 802 pierce the blood vessel 806 and the adjacent soft portion 808a until their prongs reach the rigid portion 808b of the connector, as shown in FIG. 24A. The prongs are then clinched in convergent direction by the concave surface of the rigid portion 808a, which is illustrated in FIG. 24B. In this way, a steady attachment of the connector 808 to the blood vessel 806 is accomplished. When the vessel 806 and the connector 808 are with larger diameters, the staples are ejected to a less curved surface, which is illustrated in FIGS. 25A and 25B. In this case, the concavity of the rigid portion 808b might be insufficient to produce alone clinching of the staples. Two concave grooves 808c at the internal surface of the rigid portion of the connector in front of the staple prongs are further provided. They serve to further direct the clinching of the prongs in convergent direction.

Figure 28A:
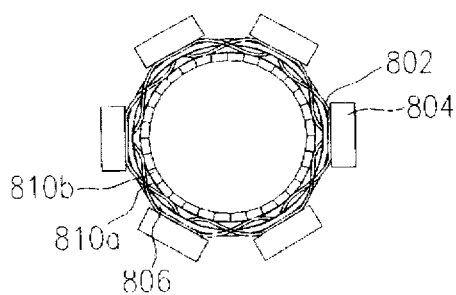
FIGS. 28A and 28B are respectively a perspective top view of two tubular structures sutured by a row of inwardly ejected and clinched staples, and a front-top view of row of staples clinched in divergent direction.
Figure 28B:

A new method for clinching of staples ejected in inward radial direction to suture an internal tubular connector to the internal surface of a tubular organ is illustrated in FIGS. 26A through 28B. Six staples 802 abutted by six plungers 804, positioned around the tubular organ 806 and the internal tubular connector 810, are shown in top view in FIG. 26. The internal connector comprises an outer tubular portion 810a, which is made of substantially soft and resistant to tension material, and an inner tubular portion 810b made of substantially rigid material. Clinching of a single staple 802 is illustrated in top view in FIGS. 27A and 27B. The prongs of the staple 802 pierce blood vessel 806 and soft portion 810a till they reach rigid portion 810b of the connector 810, as shown in FIG. 27A. Then they are curved in divergent direction by the convex surface of the rigid portion 810b, which as shown in FIG. 27B. The prongs of each staple are curved away from each other in direction to the crosspieces of the adjacent staples. In this way, the sutured structures are held tight in between the curved prongs of each staple and the crosspieces of the adjacent staples. A row of staples 802 clinched in divergent direction, which sutures connector 810 to blood vessel 806, is illustrated in top view in FIG. 28A. To avoid confrontation of the prongs of adjacent staples, it is preferable that the staples 802 are applied slightly inclined in respect to the plane of the suture line, as shown in FIG. 28B.

This new method for clinching the staple prongs in divergent direction in cases of inward stapling is a preferable method for suturing tubular structures with small lumen, as in such cases clinching of the staple prongs in convergent direction is actually inapplicable.

Figure 29A:
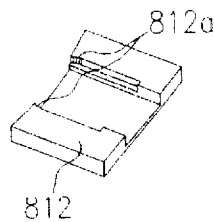
FIGS. 29A through 29D are perspective top-side views illustrating in consecutive stages a new method for clinching of staples without an anvil.
Figure 29B:
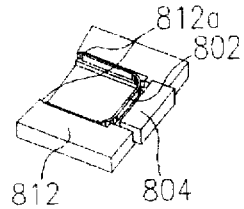
Figure 29C:
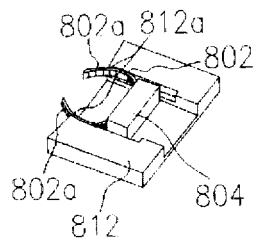
Figure 29D:
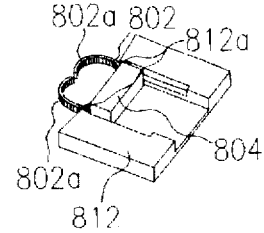

A novel method for clinching of staples without an anvil is illustrated in FIGS. 29A through 29D. A staple receptacle 812 having arcuate ends 812a curved in convergent direction is shown in FIG. 29A. Staple 802 contained in the receptacle 812 is shown in basic position in FIG. 29B, in mid-ejecting phase in FIG. 29C, and in end-ejecting position in FIG. 29D. During the exit of the staple 802 out of the receptacle 812, the arcuate ends 812a of the receptacle curve analogously the staple prongs 802a in convergent direction.

Figure 30A:
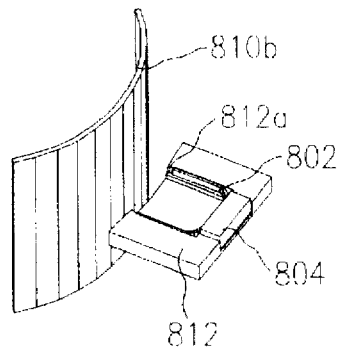
FIGS. 30A through 30C are perspective top-side views illustrating in consecutive stages clinching of staples by the anvilless method combined with tubular connectors.
Figure 30B:
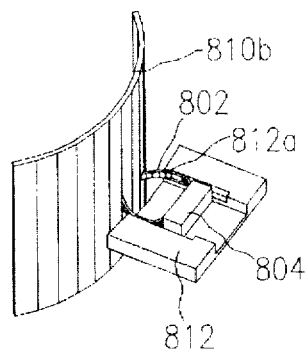
Figure 30C:
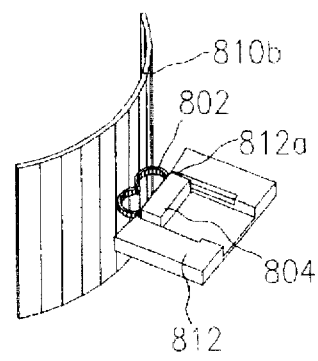

The anvilles method can be further combined with the other methods for clinching of staples in convergent direction, that have already been described. It can be utilized for initial clinching of the prongs, which are further clinched in convergent direction by the opposing rigid surfaces of tubular connecting means, or an anvil. It can be implemented with concave, convex, or flat rigid surfaces. Additional clinching by a rigid convex surface is shown in FIGS. 30A through 30C. The inwardly ejected staple 802 is curved initially by the arcuate ends 812a of the receptacle 812 and then clinched further by the convex surface of the rigid portion 810b.

The method of initial clinching of the prongs of ejected staples in converging direction by the arcuately curved ends of the staple receptacles and further clinching by opposing rigid surfaces is considered superior to the method for clinching of the staple prongs only by the grooves of opposing rigid surfaces.

Figure 31A:
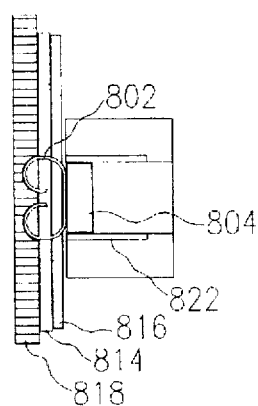
FIGS. 31A through 31C are perspective top views illustrating suturing of two structures with staples clinched by the opposing grooves of rigid surfaces.
Figure 31B:
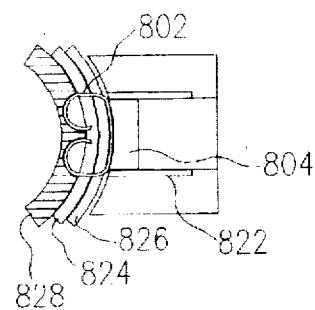
Figure 31C:
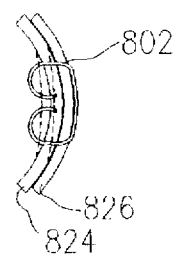
Figure 32A:
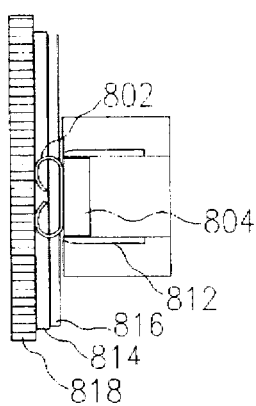
FIGS. 32A through 32C are perspective top views illustrating suturing of two structures and clinching of staples by the anvilles method in combination with rigid surfaces without grooves.
Figure 32B:
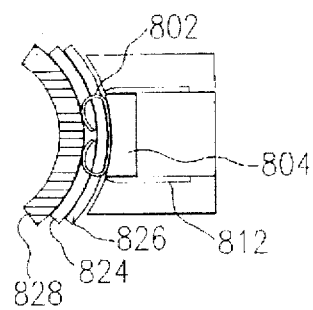
Figure 32C:
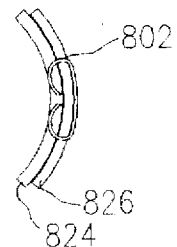

This is demonstrated in FIGS. 31A through 32C, and FIGS. 32A through 32C. Clinching of the prongs of staples by the grooves of opposing rigid surfaces for connecting two structures is shown in FIGS. 31A through 31C. Initial clinching of the prongs of staples by the arcuate ends of the receptacles and then by opposing rigid surfaces without grooves is illustrated in FIGS. 32A through 32C.

The staple 802 moves within staple receptacle 822 by the force of plunger 804. It pierces the two flat structures 814 and 816. The prongs of the staple are then clinched by the grooves 818a of anvil 818, which affixes together the two structures 814 and 816, as shown in FIG. 31A. As the grooves are bellow the surface of the anvil, the curved prongs project above the surface of the structure 814 leaving empty space bellow them. The clinched staple sutures the two structures, but their walls are not pressed to each other. The connection accomplished in this way is loose, which is not suitable for securing fluid-tight anastomoses. This negative feature is even more expressed when two tubular structures 824 and 826 are sutured with staple 802 over a tubular anvil 828, which is shown in FIG. 31B. The empty spaces bellow the curved prongs and the surface of structure 824 are bigger. The wall of structure 824 can deviate and move away from the wall of structure 826, as shown in FIG. 31C. The method for clinching of staples by the grooves of opposing rigid surfaces has found application in gastrointestinal stapling devices, but it is believed to be unsuited for suturing organs, such as blood vessels, conducting high pressure fluids.

Suturing of the same structures in the same positions, but accomplished by the method of initial clinching of the staples by the arcuate ends of receptacles and further clinching by opposing rigid surface without grooves is demonstrated in FIGS. 32A through 32C. The staple 802 moves within staple receptacle 812 ejected by the force of plunger 804. The arcuate ends 822a of the receptacle 812 curve initially the prongs of the exiting staple 802. The staple prongs pierce the two flat structures 814 and 816, and are further clinched by the opposing surface of anvil 830, as shown in FIG. 31A. The loops of the curved prongs of the staples to not extend above the surface of structure 814. In the same manner tubular structures 824 and 826 are sutured over tubular anvil 830 by a staple 802, which is illustrated in FIG. 32B. As seen in FIG. 32C, the curved prongs of the staple 802 do not protrude above the surface of structure 824, so there is no possibility for displacement of the sutured structures. The sutured structures are firmly pressed to each other, so a secure and fluid-tight connection is accomplished. This method is preferable for suturing structures, such as blood vessels, conducting fluid under high pressure.

The method is also superior to the method for clinching of staples by the grooves of opposing rigid surfaces for several other reasons as well. First, no alignment of the staples with the opposing rigid surface is needed, while the grooves have to be exactly aligned with the front of the staple prongs. Second, the arcuate ends of the receptacle prevent the staples from falling accidentally out of them. Third, when used for suturing blood vessels, the clinched prongs of the staples do not protrude into the lumen of the sutured vessels, thus avoiding possible adherence of blood cells and formation of thrombi.

The described method for initial clinching of the staples by the arcuately curved ends of the receptacles and additional clinching by opposing rigid surfaces can find application in other types of stapling devices as well, such as circular and linear gastrointestinal staplers, laparoscopic hemostatic staplers, or in any other stapling device used for accomplishing tight and secure suturing.

The tubular suturing device of the present invention is particularly efficient for anastomosing of blood vessels by attachment of tubular connecting means to their severed ends. Different types of external tubular connectors and methods for anastomosing blood vessels by attachment of the connectors to their severed ends are illustrated in the following FIGS. 33A through 42B.

Figure 33A:
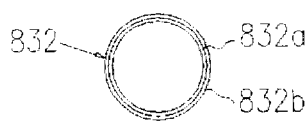
FIGS. 33A and 33B are schematic top and front views of an external tubular connector.
Figure 33B:
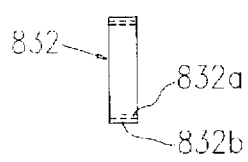

A simple type of external tubular connector 832 is shown in top and from view in FIGS. 33A and 33B. The connector 832 comprises an inner and an outer tubular portions firmly affixed together. The inner portion 832a is made of substantially soft and resistant to tension material, which allows piercing by staples and retains the clinched staples in place. Woven materials, such as Dacron™ used currently for manufacturing vessel prostheses, can be used for this purpose. Many other types of woven materials can be used as well, as the material is not in any contact with the blood flow. Other artificial materials such as rubbers or soft plastics, natural substances such as cork, or materials of homogenous origin such as dura matter can be used for the same purpose as well, provided they have sufficient tensile strength and allow piercing by staples.

The outer tubular portion 832b of the connector is made of substantially rigid material. It acts to clinch the staples ejected to it and serves to couple with accordingly matching connector. For this purposes, the outer tubular portion can be made of various types of materials, such as metals, alloys, hard plastics, ceramics, or the like suitable. It is preferable, that the material is magnetic-resonance negative, so MRI studies can be performed later.

Figure 34:
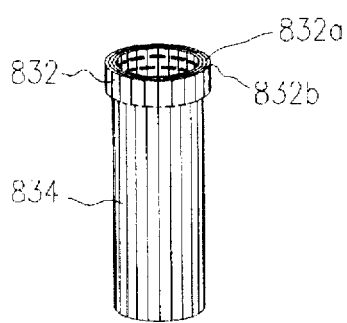
FIG. 34 is a side-top view of the external tubular connector sutured to the end of a blood vessel with staples ejected in inward radial direction.

The connector 832 is attached externally to the end of the severed blood vessel 834 by stapling with the tubular suturing device preferably with at least two rows of staples, as shown in FIG. 34.

Direct anastomosing of two blood vessels 834 and 836 attached with tubular connectors 832 to their ends is illustrated in FIGS. 34A through 34C. The two vessel ends are anastomosed by an intermediate connector 838 having inner matching surfaces reciprocating the outer surfaces of the rigid portions of connectors 832. The two blood vessels 834 and 836 attached with connectors 832 and intermediate connector 838 are shown approached axially to each other in FIG. 34A. Anastomosis is accomplished by plugging the tubular connectors 832 into the intermediate connector 838. The connected vessels are shown in schematic and perspective views in FIG. 34B and 34C. As seen in FIG. 32B, the vessel ends are exactly approximating each other. The continuity of the vessels is restored without any changes in their lumen. The inside of the anastomosis is entirely lined by the intima (innermost layer) of the vessels, there is no contact of the connectors with the blood flow.

Figure 35A:
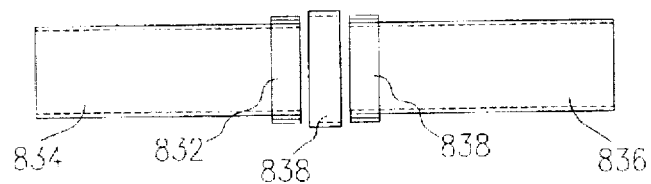
FIGS. 35A through 35C are respectively schematic front views of two vessels attached with external connectors approached to intermediate connector, a schematic and a perspective front views of the two vessels anastomosed by the coupled connectors.
Figure 35B:
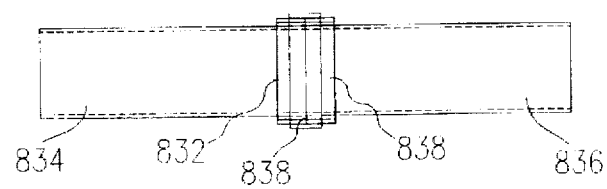
Figure 35C:
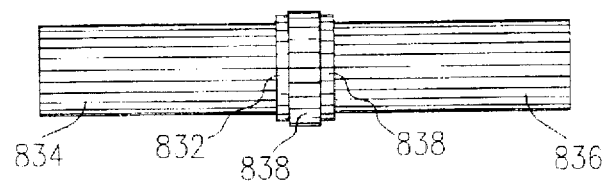
Figure 36A:
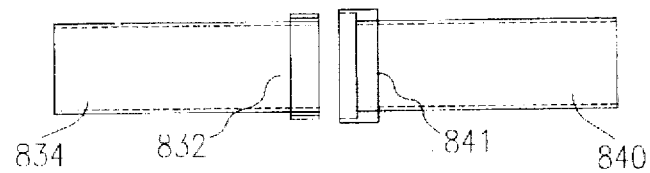
FIGS. 36A through 36C are respectively a schematic front view of two approached vessels attached with correspondingly matching connectors to their ends, schematic and perspective front views of the two vessels anastomosed by the coupled connectors.
Figure 36B:
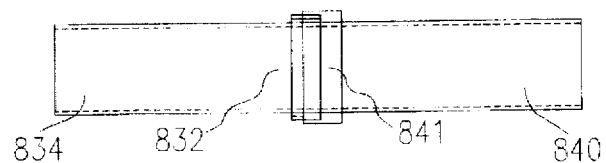
Figure 36C:
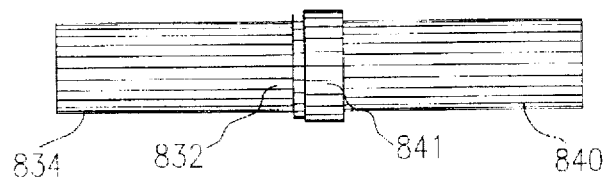

Blood vessels are anastomosed by artificial or natural grafts, when a portion of a blood vessel has to be resected and the severed vessel ends cannot be approximated. Anastomosing of the end of a blood vessel 834 with the end of prosthesis 840 is illustrated in FIGS. 35A through 35C. External connector 832 is sutured to the end of the vessel 834 by the tubular suturing device. The prosthesis 840 is with a preattached graft connector 841 at the end. The graft connector 841 is made of substantially rigid material and has a predefined inner surface to accomplish tight coupling with the outer surface of the tubular connector 832. The vessel 834 and the prosthesis 840 with the connectors 832 and 841 attached to their ends are illustrated approached axially in a schematic view in FIG. 35A. The anastomosis is accomplished by plugging the tubular connector 832 into the graft connector 841, which is shown in a schematic view in FIG. 35B and in a perspective view in FIG. 35C. As seen again, the ends of the vessel 834 and the prosthesis 840 are exactly approximated and the anastomosis is completed without any changes in the lumen. The connectors 832 and 841 remain entirely outside the vessel 834 and the graft 840. The anastomosis is lined internally only by the walls of the vessel and the prosthesis.

Coupling of tubular connecting means can be accomplished in various other methods as well, such as clipping, screwing, fastening and others suitable alike ways implemented alone or in combination, provided that a secure fluid-tight connection is effected. Exemplary illustrations of some of these possibilities are shown in FIGS. 37A through 39B.

Figure 37A:
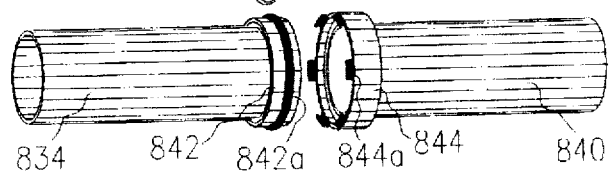
FIGS. 37A and 37B are perspective front-side views of two tubular structures with another type of external tubular connectors attached to their ends, showing them in approximated and anastomosed positions respectively.
Figure 37B:
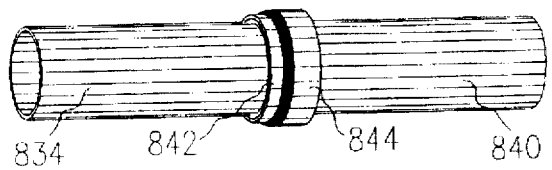

Anastomosing of blood vessel 834 and prosthesis 840 by another type of external connectors attached to their ends is illustrated in perspective views in FIGS. 37A and 37B, showing them approached and connected. A tubular connector 842 having a small rounded flange 842a on the outer side is sutured to the end of the vessel 834 by the tubular suturing device. The prosthesis is with preattached graft connector 844 that has multiple axially oriented clips 844a at the end. The vessel 834 and the prosthesis 840 are coupled by plugging the tubular connector 842 into the graft connector 844. The clips 844a of the graft connector lock around the flange 842a of the tubular connector to secure steady connection, which is illustrated in FIG. 37B.

Figure 38A:
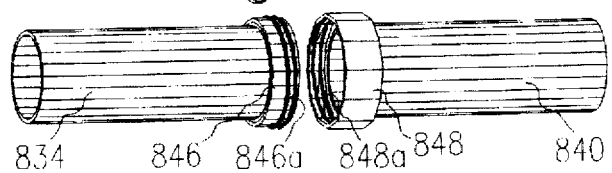
FIGS. 38A and 38B are perspective front-side views of two tubular structures with another type of external tubular connector attached to their ends, showing them in approximated and anastomosed positions respectively.
Figure 38B:
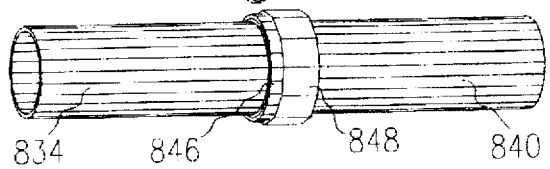
Figure 39A:
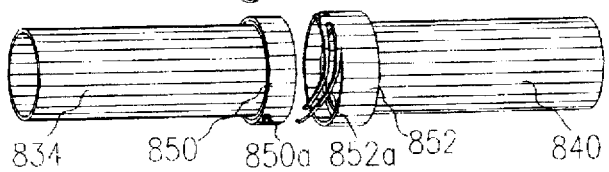
FIGS. 39A and 39B are perspective front-side views of two tubular structures with another type of external tubular connectors attached to their ends, showing them in approximated and anastomosed positions respectively.
Figure 39B:
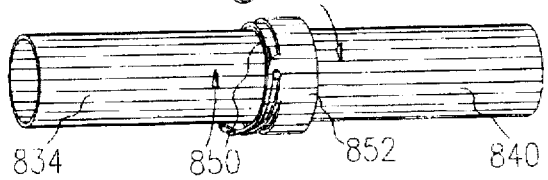

Joining of blood vessel 834 and prosthesis 840 by another type of external connectors attached to their ends, showing them approached and joined, is illustrated in perspective views in FIGS. 38A and 39B. A tubular connector 846 having an outer screw surface is attached to the vessel 834 by the tubular suturing device. The prosthesis 840A has a preattached at the end graft connector 848 with a matching inner screw surface. The vessel 834 and the prosthesis 840 are joined together by plugging and twisting the two connectors 846 and 848 in opposite directions.

Another method for connecting of blood vessel 834 and prosthesis 840 by another type of connectors, showing them approached and connected, is illustrated in FIGS. 39A and 39B. A tubular connector 850 having small protrusion 850a on the outer side is sutured to the end of the vessel 834 by the tubular suturing device. A graft connector 852 with two helical advancing arms 852a is preaffixed to the end of the prosthesis 840. The two connectors 850 and 852 are coupled together by plugging and mining them in opposite direction, so the protrusion 850a slides between the two helical arms 852a, which locks the connectors in secure position.

New type of prostheses can be used with the new tubular suturing device for replacement of resected portions of blood vessels. The prostheses are preattached at their ends with rigid graft connectors having correspondingly matching coupling surfaces. The currently used prostheses are made entirely of flexible woven material, such as Dacron™. They are sutured to the severed ends of the blood vessels by manual placement of multiple stitches. This type of prostheses is associated with a certain percentage of complications. The microstructure of their internal surface is not smooth. Blood cells can adhere to the woven fibers and thrombi can form within the prostheses. The woven walls are rather soft and they can be deviated or obliterated under pressure from adjacent organs or structures.

Main blood vessels are usually situated in the most protected spaces in the body. They are in stable position and their configuration does not change during body movements. Replacement of resected portions of such vessels can be done with entirely rigid grafts. Totally rigid prostheses, having polished and extremely even internal surfaces, can be produced from various types of materials. Different types of metals, alloys, hard plastics, ceramics, or other suitable like materials can be used for this purpose. Magnetic-resonance negative metals, such as cobalt, are preferable to allow performance of MRI studies. Transparent materials of glass or Plexiglas types are preferable, as they allow the surgeon to visualize the flow within the prosthesis. This is important, because all trapped air within the prosthesis must be fully eliminated before restoring circulation of the anastomosed vessels.

Blood vessels situated in the proximity of joints are changing their configurations during movements of the corresponding body parts. In such cases, flexible prostheses produced of substantially flexible materials such as various types of resin, rubber, soft plastics, or other suitable the like materials (preferably transparent) can by used for replacement of the resected portions of the vessels.

The prostheses made of entirely rigid material can be produced with correspondingly matching coupling surfaces of their ends, or they can be affixed with rigid graft connectors at their ends. The prostheses made of flexible material are manufactured with attached graft connectors to their ends. Connectors could also be affixed to the prostheses intraoperatively, but this is undesirable as it would prolong the operative procedure.

Methods for anastomosing blood vessels attached with external tubular connectors to their ends by the new type of vessel prosthesis are illustrated in FIGS. 40A through 42B.

Figure 40A:
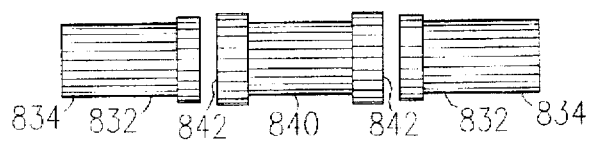
FIGS. 40A and 40B are perspective front views of two tubular structures attached with external tubular connectors, showing them approached and coupled to a prosthesis provided with correspondingly matching connectors.
Figure 40B:
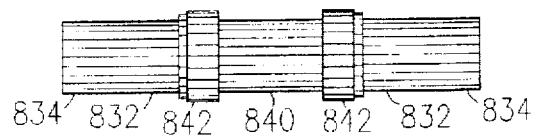

Anastomosing of the ends of two vessels 834 and 836 with the new type of prosthesis 840 is illustrated in perspective views in FIGS. 40A and 40B. Tubular connectors 832 are attached to the ends of both vessels. Prosthesis 840, with preattached graft connectors 842 at the ends, is selected with length and diameters as necessary. The two vessels connectors 832 are coupled to the corresponding graft connectors 842 and the anastomosis of the two vessels 834 and 836 by the graft 840 is completed. The two figures show the two vessels approached to the prosthesis, and the vessels anastomosed by the prosthesis.

In the various operative procedures, grafts with different lengths and calibers are needed for replacement of the resected vessels. To maintain sets of prostheses with all the possible diameters and lengths that might eventually be needed would be difficult and impractical. The necessary length of the artificial graft needed for replacement of the resected portion can be achieved by joining two or more prostheses, and/or connectors.

Figure 41A:
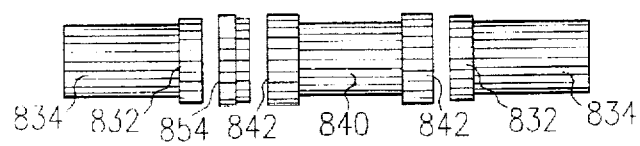
FIGS. 41A and 41B are perspective front views of two tubular structures attached with external connectors, showing them approached and coupled to a multi-segment graft comprising a prosthesis provided with correspondingly matching connectors and an intermediate connector.
Figure 41B:
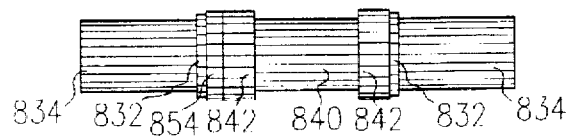

Joining the ends of two blood vessels 834 and 836, by a prosthesis 840 and an extending connector 854 is shown in FIGS. 41A and 41B. Tubular connectors 832 are sutured to the ends of the two vessels. One side of extending connector 854 has matching surface for coupling with the graft connector 852. The other side of the connector has matching surface for coupling with the tubular connector 832. The two vessels 834 and 836 are anastomosed by coupling the vessels connectors 832 sutured to their ends to the joined extending connector 854 and prosthesis 840. The two vessels, extending connector, and prosthesis approached to each other are shown in the FIG. 41A, and coupled with each other in FIG. 42B.

Figure 42A:
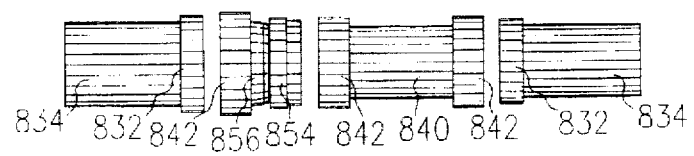
FIGS. 42A and 42B are perspective from views of two tubular organs attached with external connectors showing them approached and coupled to a multi-segment graft comprising two prostheses preattached with correspondingly matching connectors, the body of one of which is with changing lumen.
Figure 42B:
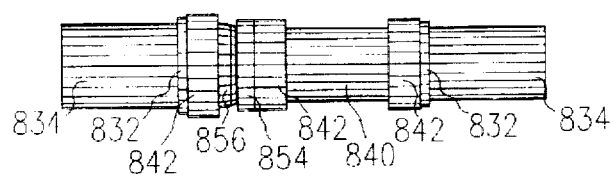

Anastomosing of vessels with different lumen by an artificial graft is shown in FIGS. 42A and 42B. External connectors 832 are sutured to the ends of vessels 834 and 836 by the tubular suturing device. Modifying prosthesis 856 and prostheses 840 with corresponding sizes and diameters are selected. The caliber of the modifying prosthesis 856 changes along its length. The modifying prosthesis 856 is preattached with graft connectors 842 and 854 having correspondingly matching coupling surfaces. The artificial graft necessary to replace the resected portion is assembled by combining modifying prosthesis 856 with prosthesis 840. The graft is coupled to the connectors 832 sutured to the ends of the vessels 834 and 836, and the anastomosis is completed.

Replacement of even long portions of blood vessels can be achieved by a combination of only two or three prostheses, and/or extending connectors. For example, each one-centimeter distance between one and fifteen centimeters is covered by a combination of two from a set of six prostheses having lengths, one, two, three, four, five, and ten centimeters. In additional combination with one extending connector of five millimeters, each half-centimeter distance between one centimeter and fifteen and a half centimeters is covered. A set of modifying the lumen prostheses with length from one to five centimeters additionally increases the number of combinations, which can be made to assemble an artificial graft with the desired length and caliber.

Suturing of the connectors to the ends of severed blood vessels is usually accomplished deep in the body tissues and within limited space. To facilitate the work of the surgeon, coupling of the tubular suturing device to an appropriate driving-supporting mechanism is needed.

Driving-supporting mechanisms 858 coupled to tubular suturing device 402 is shown in perspective view in FIG. 43. The suturing device and means for coupling with the driving-supporting mechanism were described above and shown in details in FIGS. 14A through 18B.

The driving-supporting mechanism 858 has an outer shape resembling the form of a gun. It consists of two major portions—a handle 860 and an elongated body 862. The body 862 is formed from a central supporting bar 868 and two driving bars 870 positioned on opposite sides of the supporting bar 868. The supporting bar 868 is affixed in stable position to the handle 860. The body of the tubular suturing device 402 couples to the supporting bar 868 of the driving supporting mechanism in the manner described above. Multiple rectangular rings 872 direct sliding movement of the driving bars 870 in axial direction and support them in stable position adjacent to the supporting bar 868. Two protrusions 870a of the driving bars 870 are situated on their outer sides near their ends in the handle. The protrusions 870a couple the driving bars 870 with a trigger 864. One end of the trigger 864 extends out of the handle 860 in a position to be easily effected by the fingers of the hand holding the handle. The other end of the trigger branches in two forked plates 864a having two notches 864b at their ends. Protrusions 870a fit into notches 864b. In this way, the movement of the trigger 864 is coupled with the driving bars 870. The trigger 864 turns around the axis of spindle 866 affixed in stable position by the walls of the handle 860.

The surgeon holds the driving-supporting mechanism 858 by the handle 860. With his fingers he pushes the trigger 864 towards the handle 860. The trigger 864 rotates along the axis of the spindle 866. The forked plates 864a of the other end of the trigger move in opposite direction. Their force is transmitted to the driving bars 870. Directed by the rectangular rings 872, the driving bars 870 move in axial direction downward. The body of tubular suturing device 402 is kept in a stable position by the supporting bar 968. The downward movement of the driving bars 870 is transmitted to the actuating means of the suturing device 402, which ejects staples out in outward radial direction.

Figure 46:
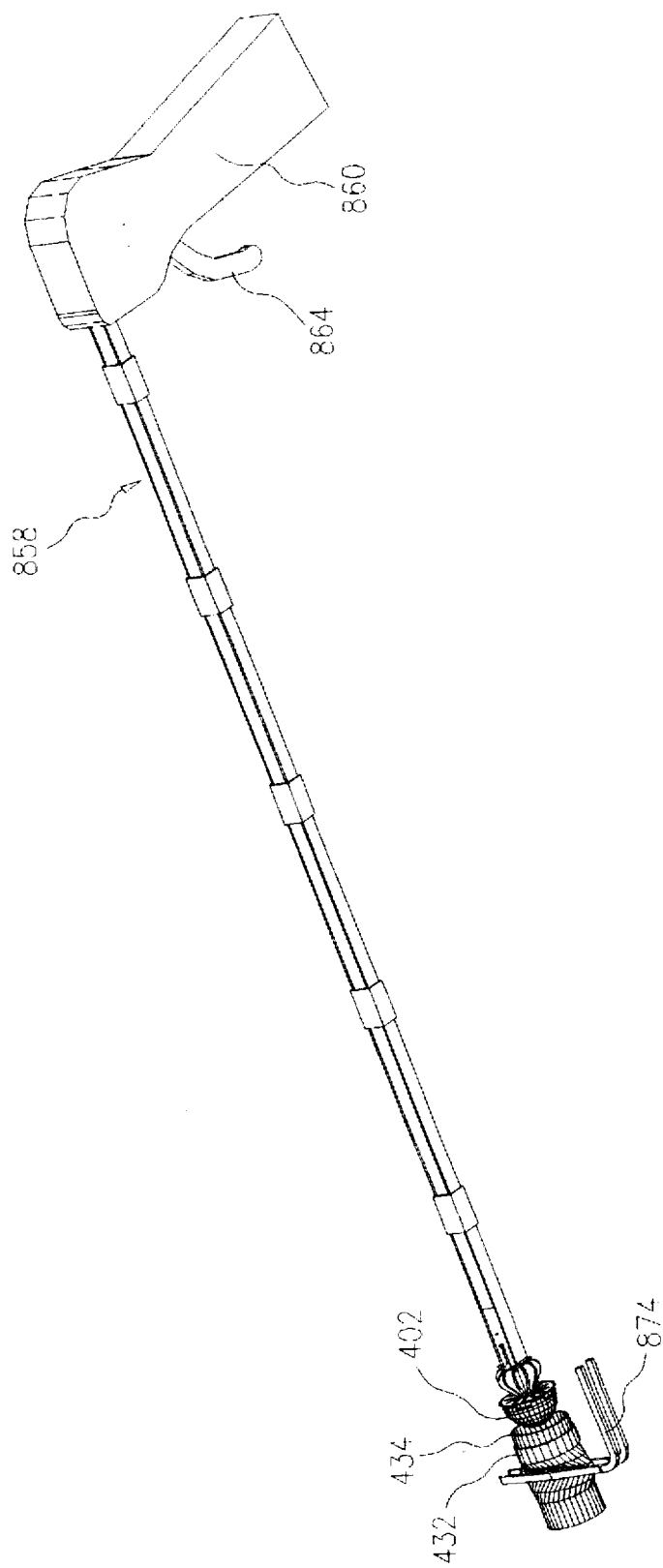
FIG. 46 is a perspective view of the tubular suturing device coupled to the driving-supporting mechanism and approached to the end of the blood vessel, and the external connector drawn over the end of the vessel.
Figure 47:
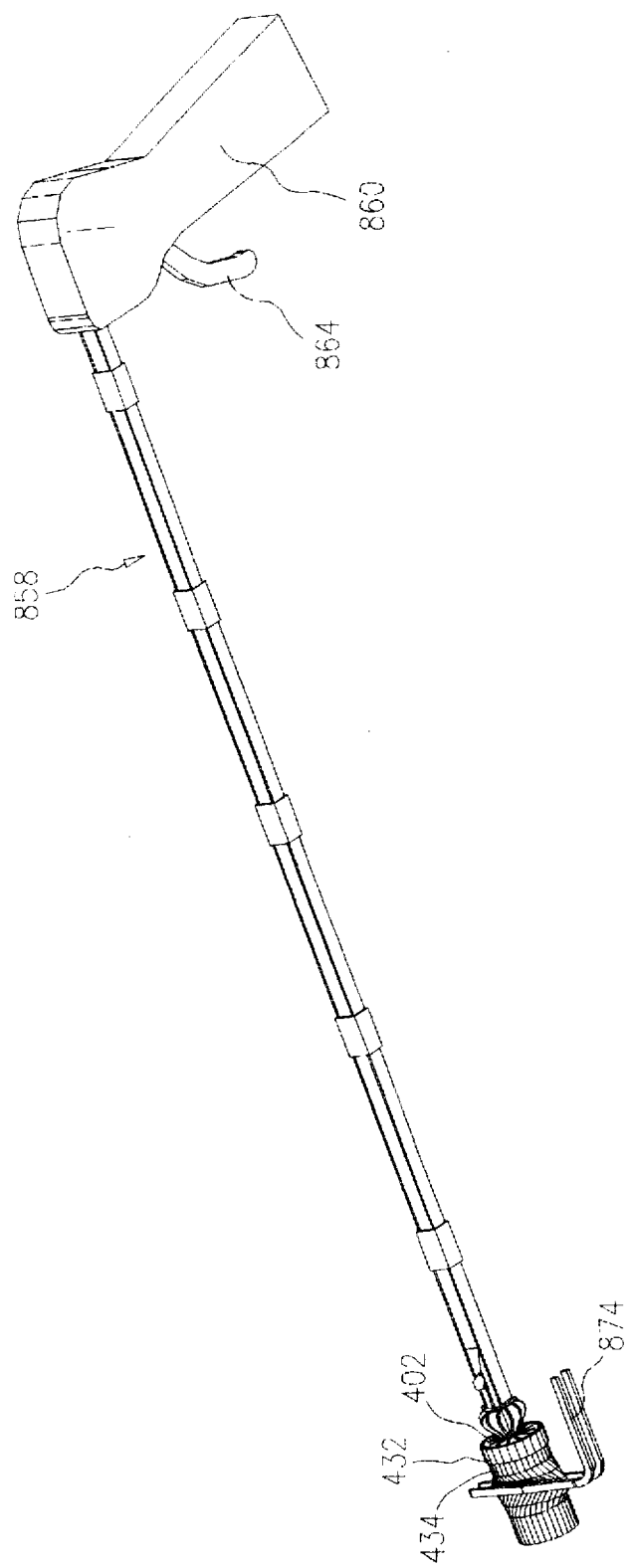
FIG. 47 is a perspective view of the tubular suturing device coupled to the driving-supporting mechanism showing the device introduced into the blood vessel and aligned with its end and with the external connector, all together in position for performing suturing action by ejecting staples in radial outward direction.
Figure 48A:
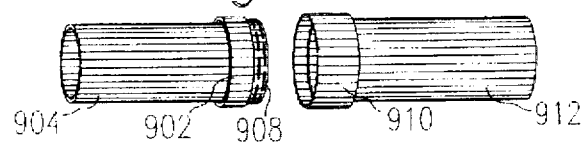
FIGS. 48A through 48D illustrate a tubular organ attached with an external tubular connector of another type by inwardly ejected staples, showing them approached to a prosthesis with correspondingly matching connectors in perspective and schematic views, and the same elements coupled by the connectors in schematic and perspective views respectively.
Figure 48B:
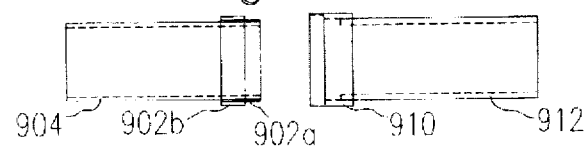
Figure 48C:
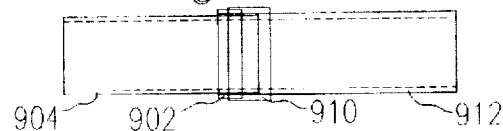
Figure 48D:
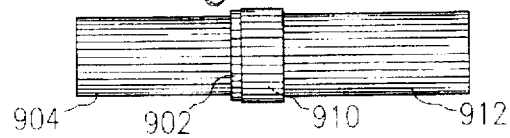
Figure 49A:
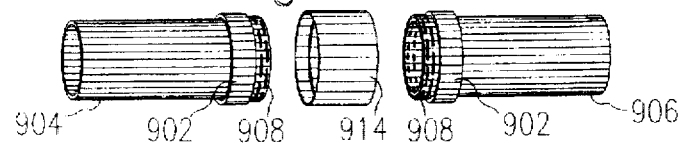
FIGS. 49A through 49D illustrate two tubular organs attached with the external tubular connectors of another type, showing them approached to an intermediate connector in perspective and schematic views, and the same elements anastomosed by coupling with the intermediate connector in schematic and perspective views respectively.
Figure 49B:
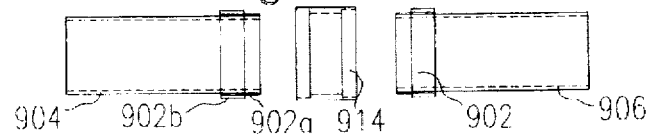
Figure 49C:
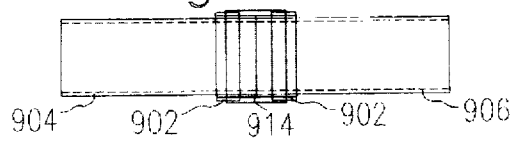
Figure 49D:
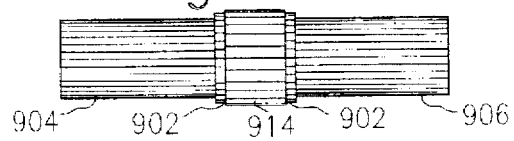

The method for suturing the external tubular connector 432 to the end of blood vessel 434 by the tubular suturing device 402 coupled to the driving-supporting mechanism 858 is illustrated in consecutive stages in FIGS. 45, 46, and 47.

Before clamping and severing the vessel, tubular suturing device 402 and external tubular connector 832 are chosen with diameters corresponding to the size of the vessel. The tubular suturing device 402 is coupled with the driving-supporting mechanism 858. The blood vessel 434 is clamped by clamp 874 and severed. The external connector 832 is drawn over the vessel 834 beyond its end, as shown in FIG. 45. The tubular suturing device 402 is introduced into the vessel end and aligned with it, which is illustrated in FIG. 46. While holding the vessel 834 in place by the clamp 874, the connector 832 is pulled back to align also with the end of the vessel 834. In this way, the end of the blood vessel 834 and the external connector 832 become precisely aligned over the suturing surface of the tubular suturing device 402, which is shown in FIG. 47. The trigger 864 is pushed then, which actuates the suturing device 402 to eject staples in outward radial direction. The ejected staples attach securely the external connector 832 over the end of the vessel 834. After that, the suturing device 402 is withdrawn out of the vessel 834.

In the described method, the attachment of the external connector to the end of the severed blood vessel by the tubular suturing device ejecting staples in outward direction is a very simple, easy, and quick to perform procedure. The selection of suturing device and external connector with appropriate sizes, and the coupling of the device with the driving-supporting mechanism is done before the blood vessel is clamped and severed. The actual time of the procedure, during which the blood flow is interrupted, is very short. Severing a blood vessel and suturing a connector to its end can be accomplished in about two to three minutes. Two connectors can be attached in about four to six minutes. Coupling of the sutured connectors to an artificial graft and removing trapped air takes an additional two to three minutes. The two vessel ends can be anastomosed with a graft and circulation can be restored within six–nine minutes in this way. This is substantially lower than the current way of manual suturing, in which it takes about twenty to thirty minutes for anastomosing of two vessels by a graft.

Most importantly, the blood vessels are anastomosed in an extremely safe and secure method. Piercing of a blood vessel by a needle or a staple creates a microlaceration of the vessel wall and small oozing of blood occurs at the site of the puncture. The outer rigid portions of the external tubular connectors sutured over the vessels cover the staple lines completely on the outside. Thus, there is no bleeding from the sites of the applied staples and there is no need for additional hemostasis. There is also no need for placement of drainages around the anastomotic lines. That shortens additionally the operative intervention as compared to the manual method, in which additional time for observation and hemostasis of persistent bleedings, and for placement of drainages is needed. Recovery of the patients is faster and many complications are avoided.

In the manual method of anastomosing, the suture lines are under the high pressure inside the blood vessels. Some of the sutures can cut through the vessel walls. If the sutures cut through all the layers of the vessel walls, very severe bleeding begins. This occurs usually intraoperatively or in the immediate postoperative period and it requires immediate surgical intervention to stop it. If the sutures cut only through the internal layer of the blood vessel, formation of dissecting aneurysm follows. This happens usually in the postoperative period, sometimes even years after the anastomotic procedure. Operative intervention for resection of the dissecting aneurysm is needed again.

In the new method of anastomosing, the suture lines are under no pressure at all. The external connectors cover entirely the suture lines on the outside. The blood vessels are surrounded by the connectors in the lines of the anastomoses. As a whole, the connectors act as rigid structures. Their walls counteract the high pressure inside the blood vessels. The walls in the lines of anastomoses are under no pressure, so there is no danger that the staples will cut through the walls. The anastomosis is much safer and more reliable. There is no risk for extensive bleedings or dissecting aneurysms.

The simplicity, easiness, quickness, and reliability of the described method makes it the most preferable method for the attachment of connectors to large and medium blood vessels. Regretfully, tubular suturing devices ejecting staples in outward direction cannot be manufactured very small, as it was explained above. The method can be used for blood vessels larger than approximately five–six millimeters. For smaller vessels, tubular suturing devices ejecting staples in inward direction have to be implemented.

Anastomosing of blood vessels attached with other types of external tubular connectors by a tubular suturing device ejecting staples in inward radial direction is shown in FIGS. 48A through 49D.

External tubular connector 902 comprises an inner and an outer tubular portions affixed to each other. The inner portion 902a of the connector is made of substantially soft material, which has sufficient tensile strength and allows piercing by staples. The outer portion 902b is made of substantially rigid material and has predetermined surface for coupling with matching connectors. The outer portion 902b covers partially the inner portion 902a. The connector 902 is attached externally to the end of the blood vessel 904 by multiple staples 908 ejected in inward radial direction, suturing the uncovered inner portion 902a to the wall of the blood vessel. The suturing procedure is described in details further on.

Anastomosing of blood vessel 904 and prosthesis 912 is completed by coupling the external connector 902 attached to the end of vessel 904 to the graft connector 908 preattached to the prosthesis 912. The vessel and the graft with the attached connectors are shown approached to each other in perspective and schematic views in FIG. 48A and FIG. 48B. They are shown anastomosed by the attached to them connectors in schematic and perspective views in FIGS. 48C and 48D. As seen from the drawings, the vessel 904 and the prosthesis 912 are joined securely to each other, their ends are approximated exactly and there is no change in their lumen.

Anastomosing of two blood vessels 904 and 906 attached with external tubular connectors 902 at their ends is illustrated in FIGS. 49A through 49D. Intermediate connector 914 is used to join the two connectors attached to the ends of vessels. The two vessels 904 and 906 with the attached connectors 902 are shown approached to the intermediate connector 914 in perspective and schematic views in FIGS. 49A and 49B. The vessels anastomosed by the intermediate connector are shown in schematic and perspective views in FIGS. 49C and 49D. Again, the vessels are anastomosed securely, their ends are approximated exactly, and there is no change in their lumen.

Figure 51A:
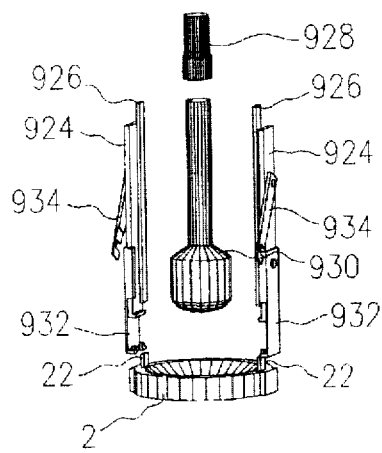
FIGS. 51A through 51E are perspective views illustrating the consequent phases of coupling of the tubular suturing device to the driving-supporting mechanism, and aligning them to the connector and the blood vessel for performing suturing operation by ejecting staples in inward direction.
Figure 51B:
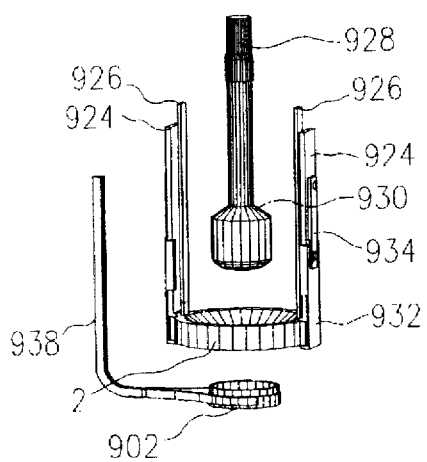
Figure 51C:
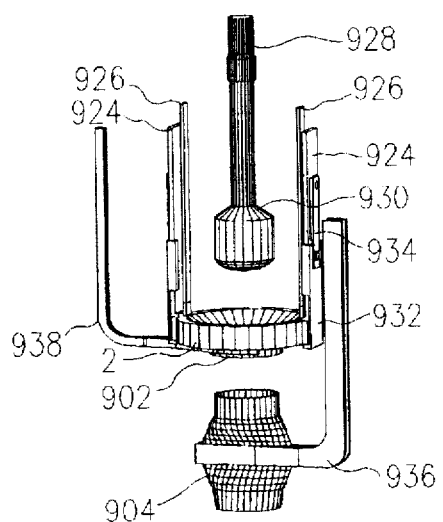
Figure 51D:
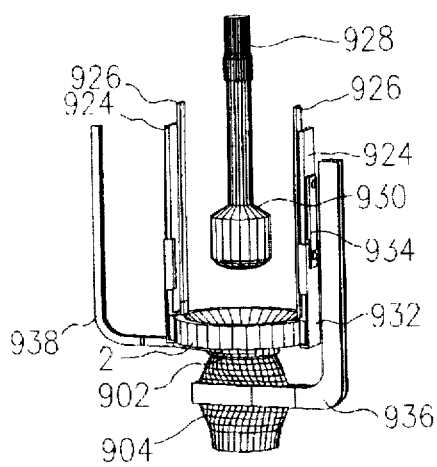
Figure 51E:
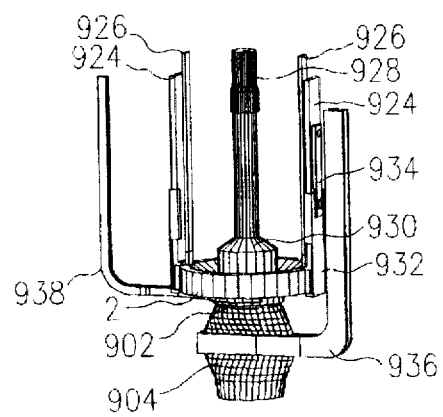

The procedure for attachment of this type of external connector to the ends of blood vessels by the tubular suturing device ejecting staples in inward radial direction is illustrated in FIGS. 50 through 51E. A driving-supporting mechanism 916 is used to support and actuate the tubular suturing device 2 (described and shown in details above). The mechanism comprises a handle 918 and an elongated body 920 approximating the form of a gun. The main portion of the body 920 consists of two supporting bars 924, and two driving bars 926, which are positioned adjacent to the inner side of the supporting bars 924. The supporting bars 924 are affixed in stable position to the handle. The driving bars 926 are coupled to trigger 922 in a manner similar to the already described above, in which the effected force on the trigger is transmitted to the driving bars moving them in axial direction downward. A central rod 928 passing through the handle 918 is positioned axially in the body of the driving-supporting mechanism. The first end 928a of the rod is provided with surface for coupling with an anvil 930 and the second end is adapted with a button 928b. Multiple stabilizing members 929 affixed between the supporting bars 924 hold the driving bars 926 and the central rod 928 passing through them in stable position and direct their movement in axial direction. The driving-supporting mechanism 916 couples by supporting-bar extensions 932 having latches 934 with the body of tubular suturing device 2. The driving-supporting mechanism 916, anvil 930, tubular suturing device 2, blood vessel 906 clamped by a clamp 936, external tubular connector 902, and a holding instrument 938 for manipulating the connector are shown in perspective view in FIG. 50.

The consecutive steps for attachment of the external connector 902 to the end of the blood vessel 906 by suturing with tubular suturing device 2 coupled to driving-supporting mechanism 916 are illustrated in FIGS. 50A through 50E. Only the front end of the driving-supporting mechanism is shown in the drawings.

Tubular suturing device 2 and anvil 930, chosen with diameters according to the caliber of the vessel 906, are shown in FIG. 50A. The anvil 930 is coupled to the first end 928a of the central rod 928. The tubular suturing device 902 is positioned between the dented inward flanges of the supporting-bar extensions 932 and the inward flanges of the ends of the supporting bars 926. The supporting-bar extension 932 are pulled up and locked by latches 934. In this way, the tubular suturing device 2 is held in stable position and its pushing members 22 are aligned in contact with the ends of the driving bars 926 of the driving-supporting mechanism, as shown in FIG. 50B. In the next step, the external connector 902 held by the instrument 938 is aligned internally to the suturing surface of the suturing device 2, which is illustrated in FIG. 50C. After that the blood vessel 906 held by the clamp 936 is aligned internally with the external connector 902 and respectively with the suturing surface of the device 2, as shown in FIG. 50D. By pushing the button 928b, the central rod 928 and respectively the anvil 930 are moved downward. This introduces the anvil 930 into lumen of the blood vessel 906 and aligns it with the suturing surface of the device 2, which is illustrated in FIG. 50E. The trigger 922 is pushed then, which moves driving bars 926 downward. They exert pressure on the pushing members 22 and actuate the tubular suturing device 2 to eject staples in inward radial direction. The ejected staples pierce the uncovered soft portion of the connector 902 and the blood vessel 906, and their prongs are clinched by the rigid surface of the anvil 930. In this way, the external tubular connector 902 is sutured securely to the end of the vessel 906. The tubular suturing device 2 and the anvil 930 are withdrawn from the vessel after that.

As evident from the drawings, this method for suturing by using an anvil is more complicated and difficult to perform than the previously described method. It requires simultaneous alignment of two flexible structures (the soft portion of the connector and the blood vessel) between the suturing device and the anvil. Therefore, this method should be reserved only for cases in which attachment of external connectors is needed, but this cannot be accomplished in the previously described method for by suturing with outwardly ejected staples. As the shown above, the previous method is simpler and easier to perform, because only one flexible structure (the blood vessel) has to be aligned between the suturing surface and the connector.

An important advantage of the tubular suturing device of the present invention over the devices if prior art becomes evident. An anvil for clinching the staples is an obligatory integral part in all of the prior art stapling devices. The tubular suturing device of the present invention ejects and clinches the staples in an anvilless way, and/or by the rigid portions of the tubular connectors. The device effects a suturing action without an anvil in a simpler, easier, and faster way, which considerably improves its performance. Furthermore, it can be supplemented with additional anvil, if this is needed, which makes its performance more universal.

Another method for anastomosing tubular structures without an anvil, by a tubular suturing device ejecting staples in inward radial direction, is illustrated in FIGS. 52A through 59B. The method describes suturing of internal tubular connectors to the ends of blood vessels. First internal connector 940 and second internal connector 942 with correspondingly matching coupling surfaces are shown approached axially in schematic and perspective views in FIGS. 52A and 52B. The first internal connector comprises 940 an outer tubular portion 940a made of substantially soft and tensile resistant material and an inner tubular portion 940b made of substantially rigid material. The outer soft portion 940a is affixed externally to the rigid portion 940b partially covering it. The two portions are shown apart in schematic and perspective views in FIGS. 53A and 53B. The second internal connector 942 has a similar structure. It comprises an outer tubular portion 942a made of substantially soft and tensile resistant material and an inner tubular portion 942b made of substantially rigid material. The soft portion 942a is affixed externally over the rigid portion 942b partially coveting it. The rigid portions 940b and 942b of the two connectors have predefined configurations to couple securely with each other.

The rigid portions of the internal connectors can be produced from various rigid materials such as metals, alloys, hard plastics, ceramics, glasses, and others the like suitable materials. The soft portions of the connectors can be produced from any substantially soft material, which has sufficient tensile strength to withhold clinched staples and allows piercing by staples. Such material can be chosen from various types of woven structures, soft plastics, rubbers, natural connective tissues, or any the like suitable material.

Blood vessels 904 and 906 are shown approached axially to first and second internal connectors 940 and 942 in FIG. 55. The connectors are chosen with internal caliber equal to the lumen of the vessels. The are introduced into the vessel ends dilating them slightly, and are sutured by inwardly ejected staples 908, which is illustrated in FIG. 56. Blood vessels are rather elastic structures and small dilatation of their walls can be easily achieved by appropriate methods. As seen, the lumen of the vessels is not narrowed by the internally positioned connectors, as the internal diameters of the connectors 940 and 942 are equal to the internal diameters of the blood vessels. It should be noted, that the connectors are illustrated with substantially thick walls for better visualization of their portions. They can be actually produced with much thinner walls (especially of the rigid portion), thus producing less dilation of the blood vessels than the illustrated one.

Vessels 904 and 906 anastomosed by the internal connectors 940 and 942 are illustrated in oblique perspective view, in front schematic view, and in front perspective view in FIGS. 57A, 57B and 57C respectively. As seen, the vessels are securely anastomosed and their continuity is restored without changes in their lumen. The two blood vessels are securely joined and there is not any possibility for bleeding from the suture lines. The blood flows exclusively through the rigid portions of the connectors, which cover entirely the staple lines on the inside. The staples have no contact with the blood flow, thus there is no possibility for blood oozing from the puncture sites. The suture line is under no pressure, as the internally positioned connector isolates it from the high pressure inside the vessel. There is no tension on the suture line and there is no danger that the staples cut through the vessel walls. This avoids the risk of extensive bleedings or dissecting aneurysm. The anastomosis is extremely safe and reliable.

New types of prostheses, similar to those described already with the external connectors, can be used for replacing a resected portion of a blood vessel. Prosthesis 944 of this type is shown in FIG. 58. The two ends of the prosthesis are with predefined matching surfaces for coupling with the two internal tubular connectors 940 and 942. Vessels 904 and 906 sutured with internal connectors 940 and 942 are shown approached axially to the prosthesis 944 in FIG. 59A, and coupled to it in FIG. 59B. All of the stated above about the new type of prostheses in utilization with external connectors, is valid in the same way about the prostheses for implementation with internal connectors. The artificial graft necessary to replace a resected portion of blood vessel can be assembled by several prostheses with constant or modifying diameter, in combination or not with additional connectors.

Figure 60:
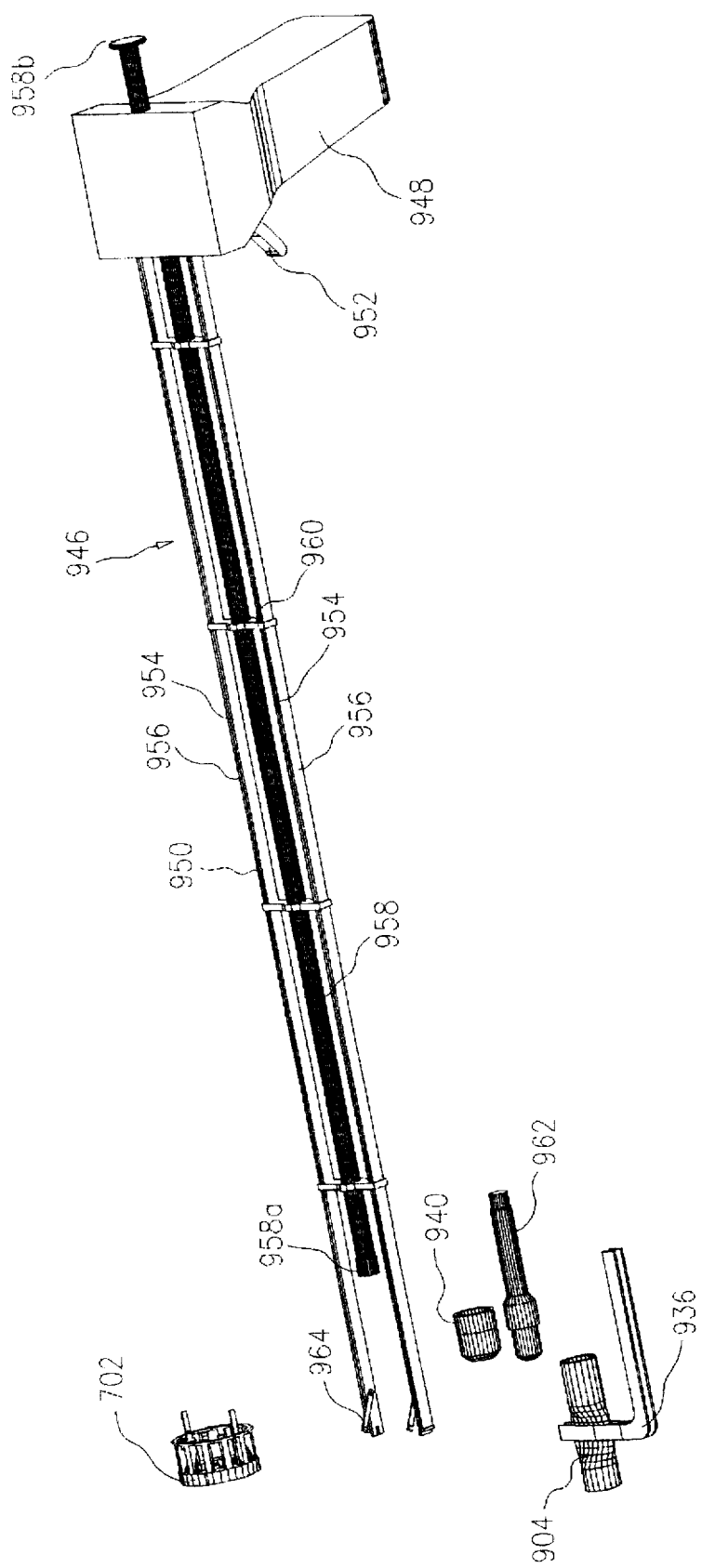
FIG. 60 shows in a perspective view the tubular suturing device of FIGS. 21A through 21E, a driving-supporting mechanism, a clamped blood vessel, and an internal connector.
Figure 61:
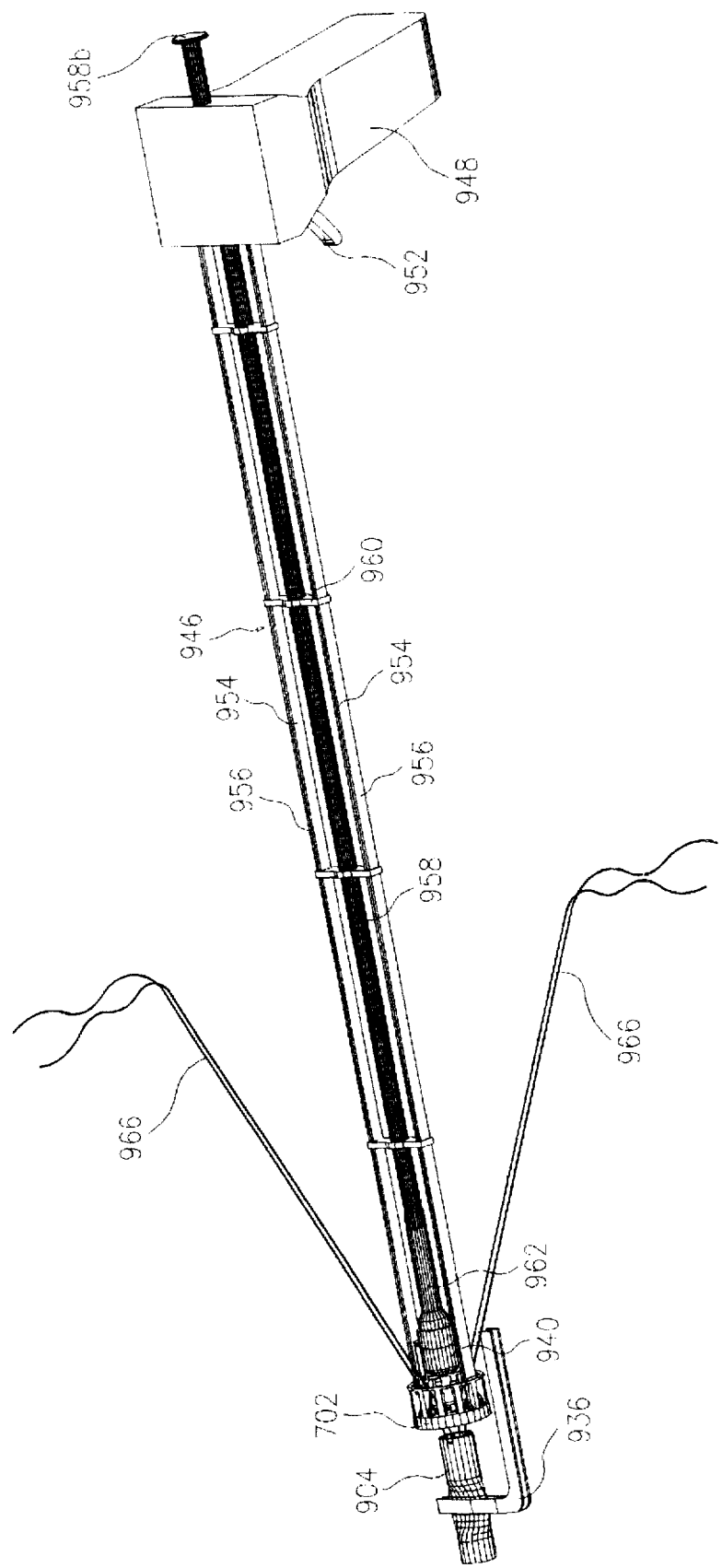
FIG. 61 shows in a perspective view the tubular suturing device and the internal connector in operative engagement with the driving-supporting mechanism, and the clamped blood vessel approached to the suturing device by two holding sutures.
Figure 62:
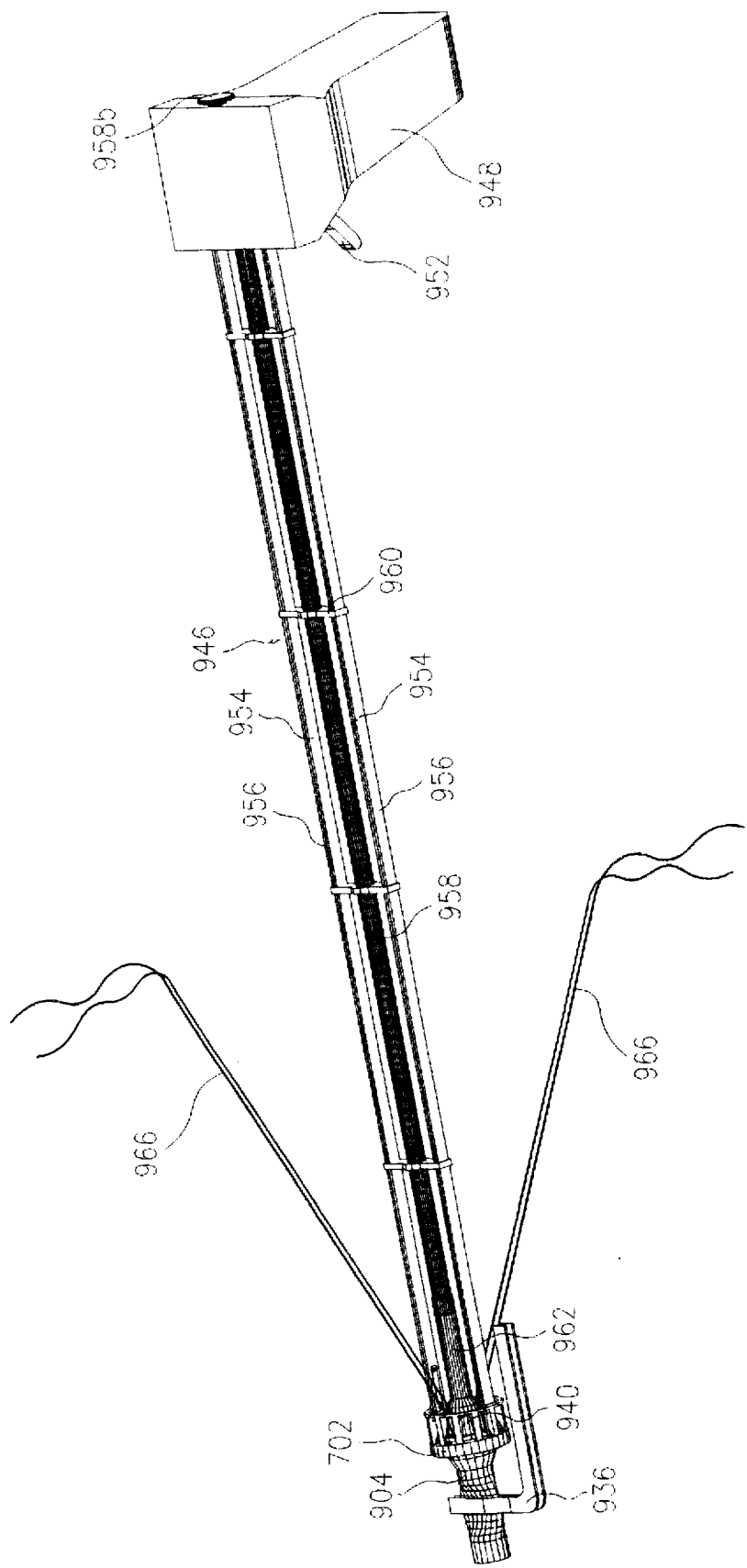
FIG. 62 shows in a perspective view the tubular suturing device coupled to the driving-supporting mechanism, the internal connector introduced into the end of the clamped blood vessel and both of them aligned with the suturing surface of the device in position for performing suturing action by ejecting staples in inward radial direction.

The method for suturing an internal tubular connector to the end of a blood vessel by the tubular suturing device ejecting staples in inward direction is illustrated in FIGS. 60 through 62. Driving-supporting mechanism 946, tubular suturing device 702, blood vessel 904, and internal connector 940 are shown in FIG. 60. The driving-supporting mechanism 946 has a gun-like outer shape. It comprises a handle 948 and an elongated body 950. The body 950 consists of two driving bars 956, two supporting bars 954 positioned adjacent and inner to the driving bars, and a central rod 958. The driving bars 956 are coupled to trigger 952 inside the handle 948 in a way, that pressing the trigger produces axial movement of the driving bars downward (in a similar manner already shown above). The supporting bars 954 are affixed in stable position to the handle 948. The central rod 958 passes through handle 948. The first end 958a of the rod 958 has a matching surface for coupling with rod extension 962. The second end is provided with a button 958b for pressing by the surgeon. Multiple stabilizing members 960 affixed to the supporting bars 954 support and direct the movement of the driving bars 956 and the central rod 958.

The driving-supporting mechanism 946 couples to tubular suturing device 702 by latches 964 (the suturing device and means for coupling with the driving-supporting mechanism were described and shown in details above in FIGS. 21A through 21E). The rod extension 962 couples with one end to the central rod 958. With the other end, the rod extension 962 supports the internal connector 940 in central axial position during the stapling action.

Tubular suturing device 702, internal connector 940, and rod extension 962 are selected with sizes accordingly to the size of blood vessel 904, shown held by clamp 936.

In operative action, the tubular suturing device 702 is coupled to the driving-supporting mechanism 946, the rod extension 962 is coupled to the central rod 958, and the internal connector 940 is positioned over the rod extension. The surgeon then places manually two holding sutures 966 at the end of blood vessel 904. The ends of the sutures 966 are drawn through the tubular suturing device 702, which is shown in FIG. 61. With the help of the sutures 966, the end of the blood vessel 940 is aligned with the internal suturing surface of the device 702. By pushing button 958b, the central rod 958 is moved downward, while holding in place the end of the vessel 940 by the sutures 966. This introduces the internal connector 940 mounted over the rod extension 962 into the end of the vessel 904 dilating it slightly, which is shown in FIG. 62. The end of the vessel 904 and the internal connector 940 become aligned with the inner surface of the tubular suturing device 702. The trigger 952 is pushed then, which by driving bars 956 actuates the tubular suturing device 702 to eject staples in inward radial direction. The ejected staples suture the blood vessel 904 to the internally positioned connector 940. After that the holding sutures are cut and removed, and the tubular suturing device is withdrawn out of the vessel.

As explained above, the preferable method for suturing external connectors to blood vessels by tubular suturing device ejecting staples in outward direction cannot be implemented for vessels smaller than approximately five-six millimeters. For smaller vessels, attachment of internal tubular connectors by the tubular suturing device ejecting staples in inward direction is the preferable method. The method takes longer time, which is needed for the forceful insertion of the internal connectors into the lumen of the vessels. Small vessels are more elastic and easier to dilate than large ones. Excluding the cerebral and coronary vessels, their blood supply is less critical and their blood flow can be interrupted for a longer time, which is necessary to perform the procedure. The anastomosis with internal connectors is not so simple and quick as with external connectors, but it is still performed in a sufficiently easy and fast way. Most importantly, it is extremely safe and reliable.

By the tubular suturing device ejecting staples in inward radial direction, blood vessels can be directly sutured over entirely rigid prostheses, or prostheses with two rigid ends at least. This is illustrated in FIGS. 63 through 69.

Figure 63:
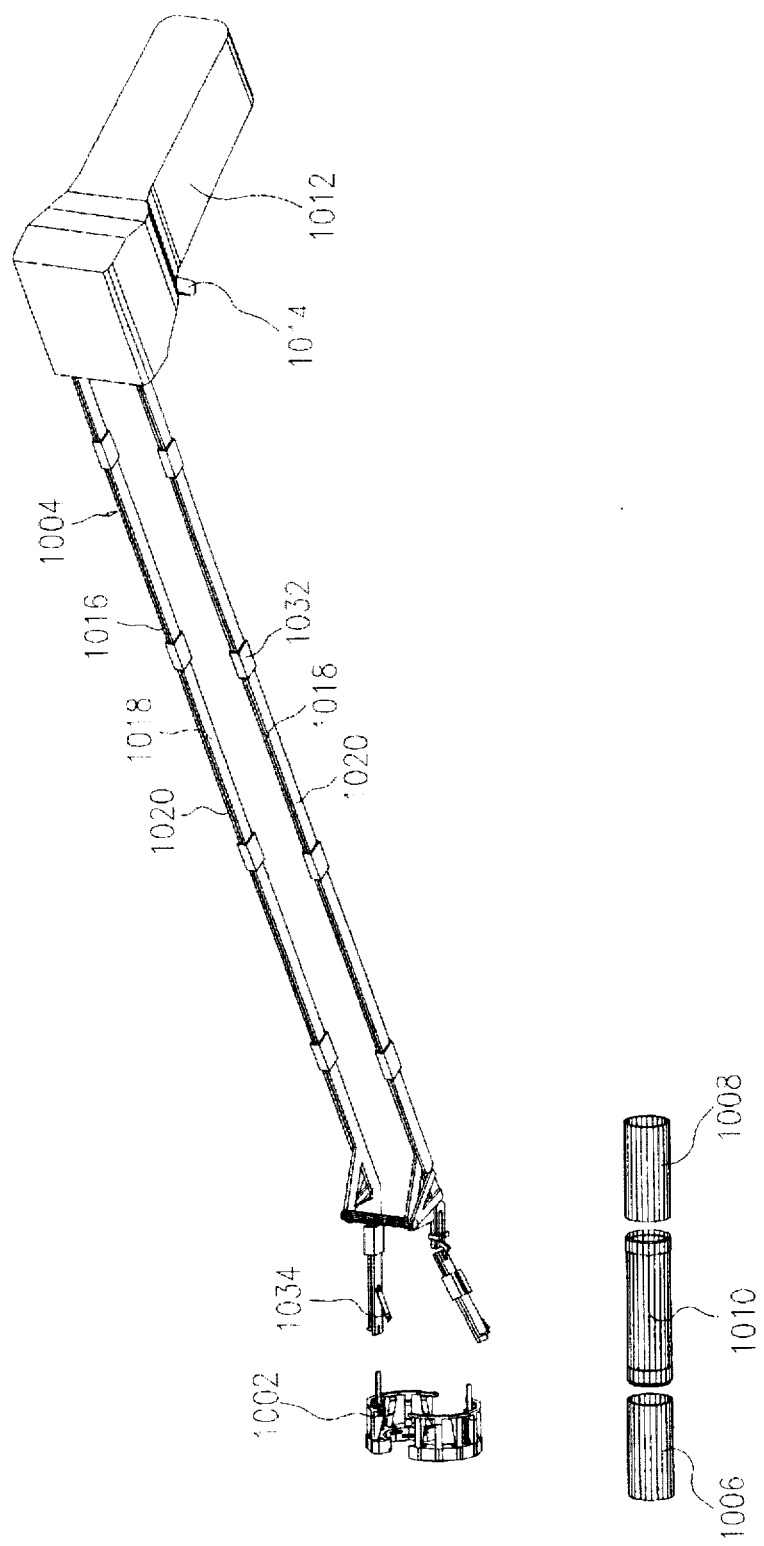
FIG. 63 shows in a perspective view the tubular suturing device of FIGS. 21A through 21E divided in two halves, a driving-supporting mechanism, two blood vessels, and an internal prosthesis with rigid ends.

Tubular suturing device 1002 for ejecting staples in inward direction, driving-supporting mechanism 1004, two blood vessels 1006 and 1008, and prosthesis 1010 having two rigid ends are shown in perspective view in FIG. 63. The ends of the prosthesis are covered with substantially soft and tensile resistant material in a manner similar that shown above with internal connectors. Tubular suturing device 1002 is identical to tubular suturing device 702 (described above in details), except that the device is divided in two halves 1002a and 1002b. Driving-supporting mechanism 1004 is similar in structure and method of action and to the driving-supporting mechanism 946. It comprises a handle 1012 for holding the device, a trigger 1014 for effecting force, and a body 1016. The body 1016 consists of two supporting bars 1018 and two driving bars 1020 positioned adjacent to the them on their outer sides. The first ends of the supporting bars 1018 are affixed to the handle 1012 in a stable position. Their second ends, angulated at approximately forty five degrees, couple with the tubular suturing device 1002. The first ends of driving bars 1020 are coupled with the trigger 1014 in a manner already shown. With their second ends, they contact to angular levers 1024 turning around spindle 1026, which is supported in firm position by two plates 1028 affixed to the supporting bars 1018. The angular levers 1024 transmit the linear movement of the driving bars 1020 to driving bar extensions 1022 in a plane angulated at approximately forty five degrees. Multiple rectangular rings 1032 hold in steady position and direct the movement of the driving bars 1020 and driving-bar extensions 1022. On one side, the supporting bar 1018a and the driving-bar extension 1022a are interrupted and pivoted to a hinge 1030. Latches 1034 secure the attachment of the tubular suturing device 1002 to the driving-supporting mechanism 1004.

Figure 64:
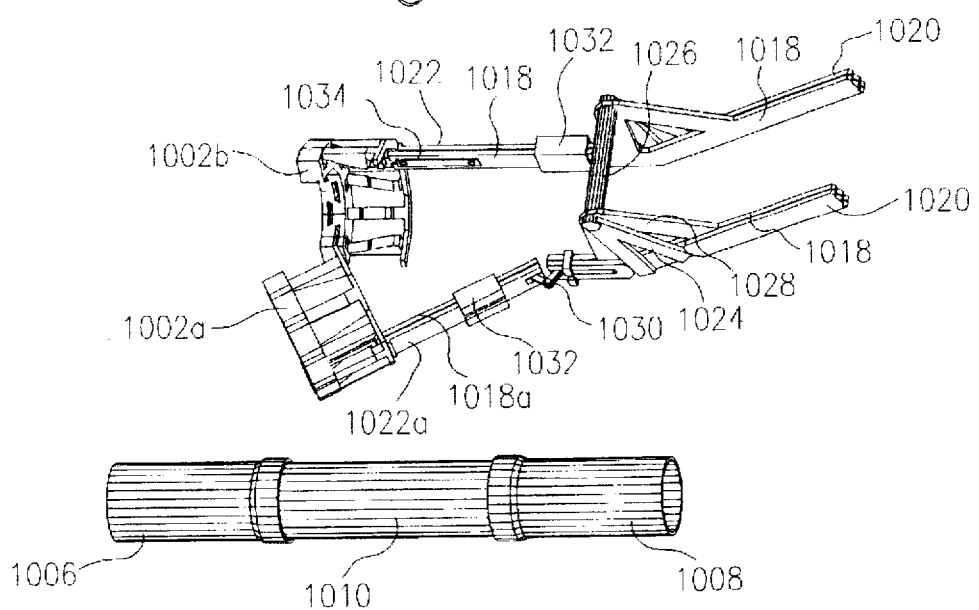
FIG. 64 shows in a perspective view the tubular suturing device coupled to the driving supporting mechanism, and the prosthesis introduced into the ends of the two vessels.
Figure 65:
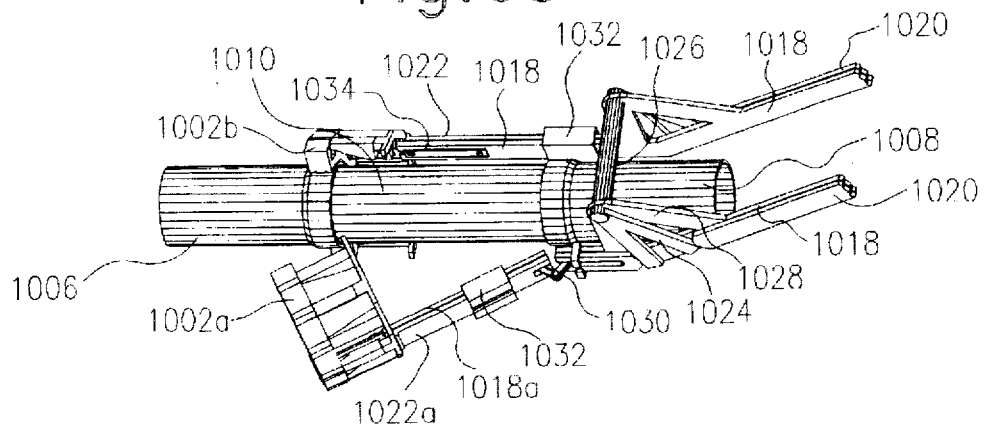
FIG. 65 shows in a perspective view positioning of one of the halves of the tubular suturing device around one of the prosthesis ends introduced into the end of one of the vessels.

Tubular suturing device 1002 and prosthesis 1010 with sizes according to the diameter of the blood vessels are selected. The two halves 1002a and 1002b of the device are coupled to the supporting bars 1018 and locked with latches 1034, as shown in FIG. 64. The two ends of the prosthesis 1010 are introduced into the ends of the blood vessels 1006 and 1008 dilating them slightly.

First, half 1002b of the tubular suturing device 1002 is positioned over the vessel 1006, which is illustrated in FIG.

Figure 66:
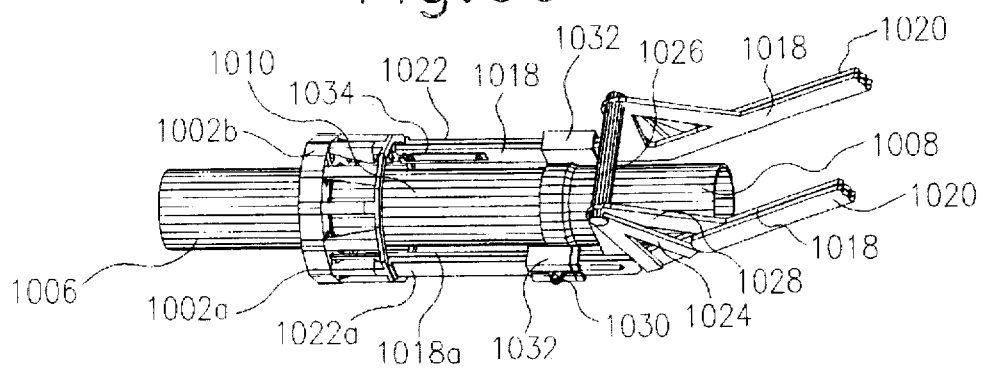
FIG. 66 shows in a perspective view positioning of the other half of tubular suturing device around one of the prosthesis ends introduced into the end of one of the vessels.
Figure 67:
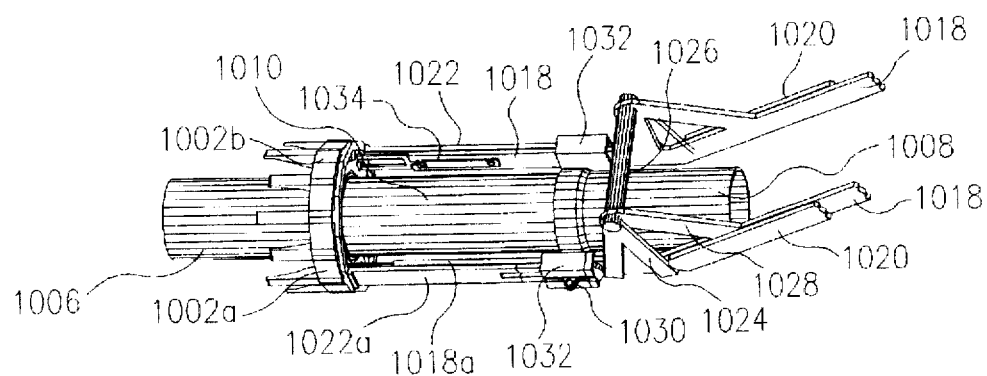
FIG. 67 shows in a perspective view the tubular suturing device positioned around one of the prosthesis ends introduced into the end of one of the vessels, illustrating the device in end-ejecting position of the stapling action.
Figure 68:
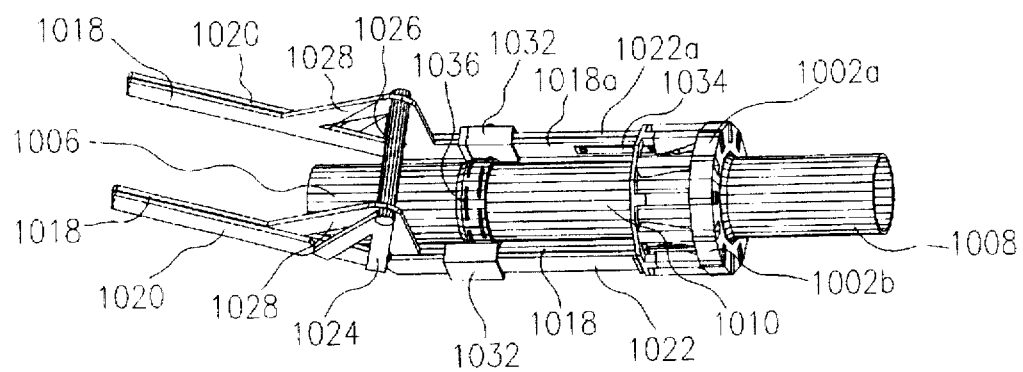
FIG. 68 shows in a perspective view the tubular suturing device positioned around the other of the prosthesis ends introduced into the end of other vessel.
Figure 69:
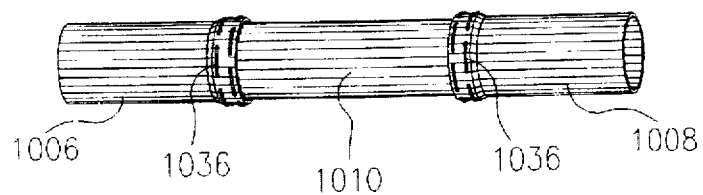
FIG. 69 shows in a perspective view the two vessels anastomosed by the internal prosthesis sutured to their ends by staples ejected in inward radial direction.

65. Then, half 1002a of the suturing device is turned along hinge 1030 and positioned also over the vessel, as shown in FIG. 66. By stabilizing member 1032a, supporting bar 1018a and driving-bar extension 1022a are locked in steady position. In this way, the tubular suturing device 1002 is positioned around the ends of the vessel 1006 and the prosthesis 1010, which is shown in FIG. 67. Then the trigger is pushed which moves driving bars 1020 downward. By the angular levers 1024, their force is transmitted to the driving-bar extensions 1022, which actuate the tubular suturing device 1002 to eject staples 1036 in inward radial direction. The ejected staples 1036 suture the end of the vessel 1006 over the end of the prosthesis 1010. In the same manner, the end of vessel 1008 is sutured over the other end of the prosthesis 1010, as shown in FIG. 68. Vessels 1006 and 1008 sutured to the ends of prosthesis 1010 by inwardly applied staples 1036 are shown in FIG. 69.

With the new tubular suturing device, the work of the surgeon is significantly facilitated and automated. Tubular connecting means are attached quickly, easy, and securely to the ends of severed blood vessels. The performed anastomoses are safe and reliable. The period of time during which the blood flow is interrupted and of the whole operative intervention are shortened substantially. Bleedings and other complications are minimized. The only remaining risk for the surgeon, that could complicate the operative procedure, is a possible inaccurate estimation of the sizes of the needed tubular suturing devices, connectors, and prostheses.

Before severing the blood vessel, the surgeon has to determine the caliber of the vessel in the lines of resection and the length of the vessel portion to be resected. Then he selects and prepares the tubular suturing device, connectors, and prostheses with according sizes and lengths. Any inaccuracy and discrepancy in the determination of the sizes of the vessels can complicate and prolong the surgical procedure. Visual determination alone is a subjective process associated with a certain rate of inaccuracy. To avoid such risks, two instruments for a circumferential and for a linear measurements of tubular organs are further described.

Figure 70A:
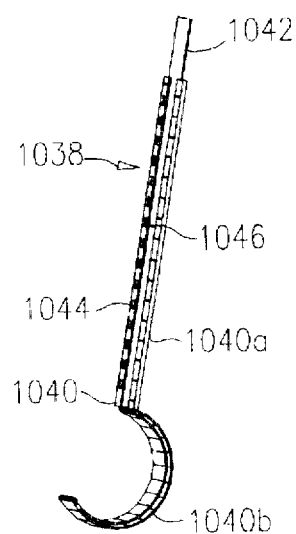
FIGS. 70A through 70C illustrate in perspective views an instrument for circumferential measurement of tubular structures in different phases of operation.
Figure 70B:
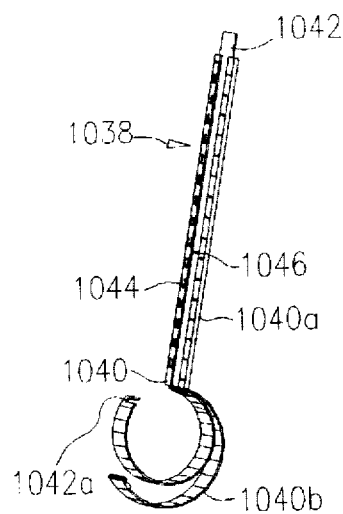
Figure 70C:
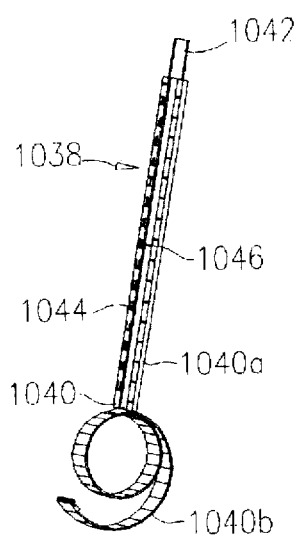

An instrument for circumferential measurement of tubular structures such as blood vessels is shown in perceptive views in FIGS. 70A through 70C. The instrument 1038 consists of rigid body 1040 having a straight portion 1040a and an arcuate portion 1040b. The straight portion 1040a encompasses a flexible tape 1042 leaving open the front side of the tape. The tape 1042 follows the curvature of the arcuate portion 1040b and ends with a loop 1042a, which it is attached temporarily to the end of the arcuate portion, as shown in FIG. 70A.

In operative action, the arcuate portion 1040b of the body and tape 1042 are inserted below the vessel to be measured. The end of the tape 1042 is released from the arcuate portion 1040b, as shown in FIG. 70B. By the loop 1042a, the tape 1042 is attached to the origin of the arcuate portion 1040b from the straight portion 1040a, which is illustrated in FIG. 70C. After that, the tape 1042 is pulled up to encircle closely the tubular structure caught into it. The straight portion 1040a is graded with numbered marks 1044 on the front side. One mark 1046 is placed in a predefined location on the front side of the tape 1042. Movement of the tape up or down moves accordingly the mark 1046. The position of the mark 1046 of the tape 1042 in relation to the numbered marks 1044 of the straight portion 1042a shows the size of the tubular structure encircled within the tape.

The numbered marks on the body can show the actual size of the encircled vessels in millimeters. Then, the surgeon has to calculate the sizes of the needed connectors and tubular suturing device. It is preferable that the marks are not showing the real size of the vessel, but they are conditional numbers showing the numbers of the corresponding connector and tubular suturing device that are needed. For example, a blood vessel with an external diameter of 20 millimeters has a wall thickness of about 1.4 millimeters, and a blood vessel with a diameter of 8 millimeters has a wall thickness of about 0.6 millimeters. Tubular suturing devices should be produced with diameters corresponding to the size and thickness of the vessels and the connectors. To assure the precise stapling of the blood vessel, the vessel must be positioned tightly between the suturing surface of the device and the connector. For optimal results, the distance between the suturing device and the connector has to be equal to the thickness of the vessel positioned between them. So, in the case of the vessel with the size of 20 millimeters, the instrument for circumferential measurement shows the number 28, for example. The surgeon then picks an external connector and a tubular suturing device with the same numbers. The actual internal diameter of the external connector with this number will be 20 millimeters, and the actual diameter of the suturing surface of the device with this number will be 18.6 millimeters. In the case of the vessel with the size of 8 millimeters, the measuring instrument shows the FIG. 12, for example. The connector and the tubular suturing device with the same numbers will have actual diameters of 8 millimeters of the connector and 7.4 millimeters of the suturing device. The difference between the suturing surface of the device and the connector in the case of the vessel with the size of 20 millimeters is 1.4 millimeters, while it is 0.6 millimeters in the case of the vessel with the size of 8 millimeters. This corresponds exactly to the thickness of the walls of the blood vessels. The work of the surgeon is simplified and facilitated, as there is no need for calculations. Prostheses also will come with numbers corresponding to the numbers of the connectors that they are coupling with.

Figure 71A:
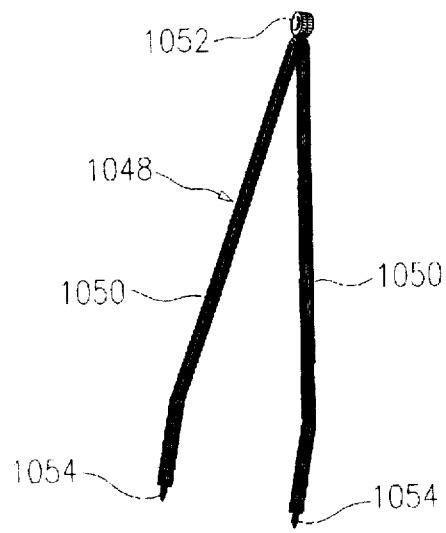
FIGS. 71A and 71B show in perspective views an instrument for linear measurement of tubular structures shown in different phases of operation.
Figure 71B:
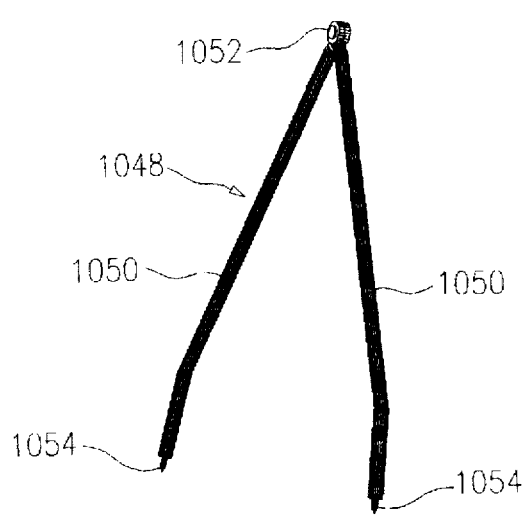

An instrument for measurement of the length of tubular organs, which need to be resetted and replaced with a graft, is illustrated in perspective views in FIGS. 71A and 71B. The instrument 1048 comprises two rigid arms 1050 hinged at one of their ends by a bolt 1052. Two pens 1054 are affixed to the free ends of the arms. The arms 1050 mm around the axis of the bolt 1052. This opens or closes the instrument in a scissors-like manner, which changes the distance between the two pens 1054, as shown in FIGS. 71A and 71B.

Replacing a pathological portion of a blood vessel by application of the two instruments for circumferential and linear measurement is illustrated in FIGS. 72 through 76. Blood vessel 1056 with branches 1058 and 1060 has a fusiform aneurysm 1062 (pathological dilatation of the vessel) incorporating a portion of the vessel including the origins of the branches. The proximal portion 1056a of the vessel is larger then the distal portion 1056b, as the vessel narrows after it gives the two branches.

Figure 72:
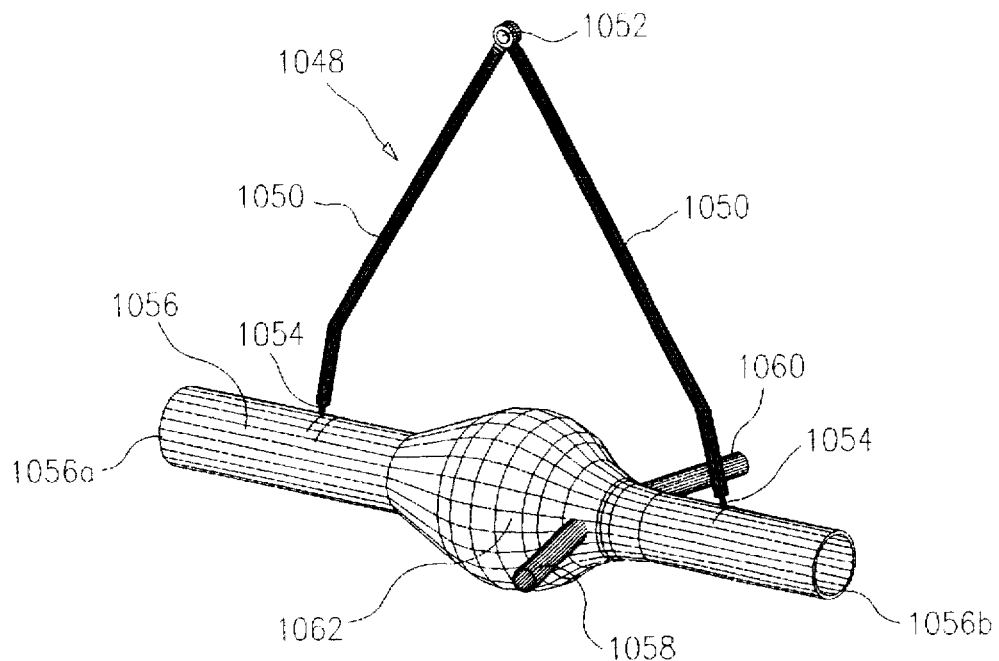
FIG. 72 illustrates in a perspective view determining the length of resection by the instrument for linear measurement of the pathological portion of a blood vessel having two branches.
Figure 73:
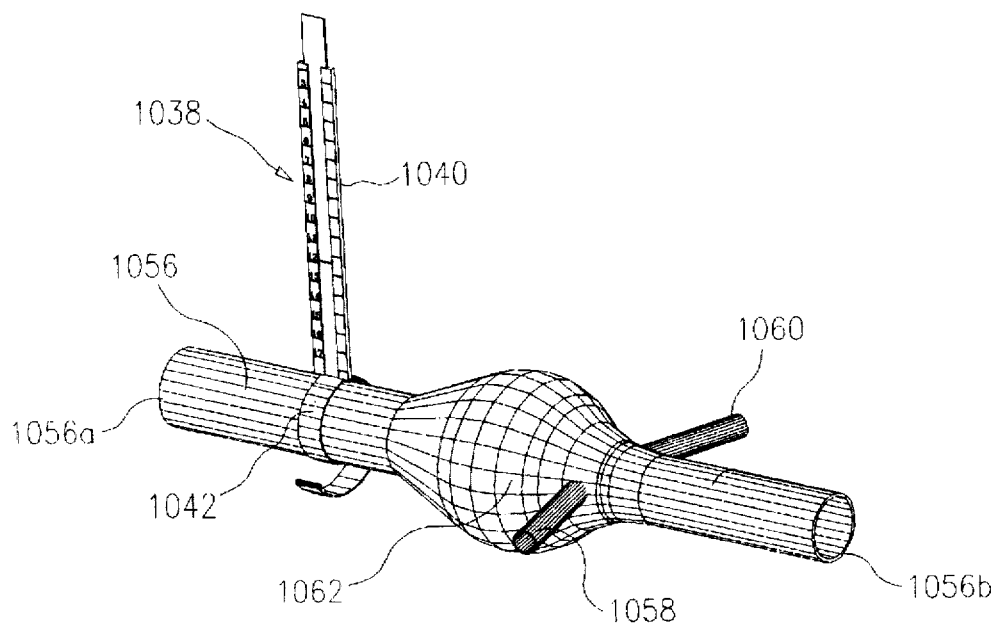
FIG. 73 illustrates in a perspective view determining the calibers of the blood vessel in the lines of resection by the instrument for circumferential measurement.
Figure 74:
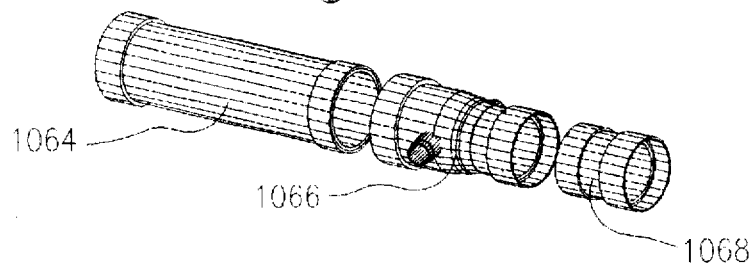
FIG. 74 illustrates in a perspective view the selected prostheses for replacement of the resected portion of the blood vessel.

First, the surgeon plans visually the lines of resection of the pathological portion of the blood vessel. Then, the surgeon opens the arms 1048 of the linear measuring instrument 1048 and with the pens 1054 places marks on the vessel 1056 in the intended lines of resection, which is shown in FIG. 72. After that, the instrument is taken out without changing its configuration and the distance between the pens is measured with a ruler. The measured length, for example, is sixty two millimeters. A graft only with a length of sixty, or of sixty five millimeters can be assembled. So the surgeon shortens with two millimeters (as shown) or expands with three millimeters the previously planned portion for resection, and places a second definite mark on the wall of the blood vessel. With the help of the instrument for circumferential measurement 1038, the surgeon then measures the size of the vessel 1056 in the proximal line of resection, as shown in FIG. 73, and in the same manner the sizes in the distal line of resection and of the two branching vessels 1058 and 1060.

Figure 75:
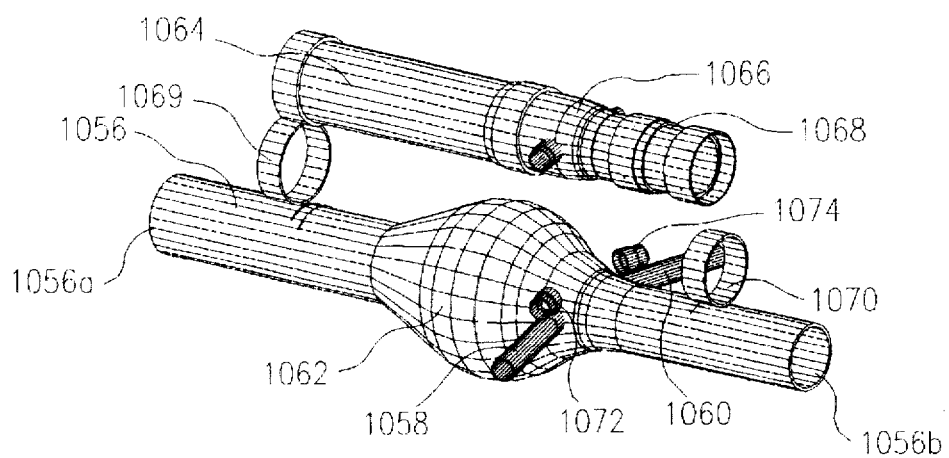
FIG. 75 illustrates in a perspective view the graft and the selected connectors, illustrating visual verification of their dimensions in relation to the planned for resection portion of the blood vessel.

Knowing the length of the portion planned for resection and the vessel sizes in the lines of resection, the surgeon then selects connectors, prostheses and tubular suturing devices with corresponding dimensions. The graft necessary for the replacement of the pathological portion of the blood vessel is prepared from three prostheses 1064, 1066, and 1068, which are shown approached to each other in FIG. 74. The middle prosthesis 1066 is with a narrowing lumen and has two branching exits. An artificial graft is assembled from the three coupled prostheses. External connectors 1068 and 1070 for attachment to the proximal and distal ends, and two internal connectors 1072 and 1074 for attachment to the ends of the branching vessels are selected. The surgeon places the assembled graft and connectors over the vessel to verify visually, that the selected connectors and the assembled graft correspond to the diameters of the vessels and the length of the planned resection, which is shown in FIG. 75. The resection lines of the vessel branches are also marked. In addition, the surgeon couples and uncouples the selected connectors to the ends of the assembled graft in order to double check that they match precisely with each other.

Figure 76:
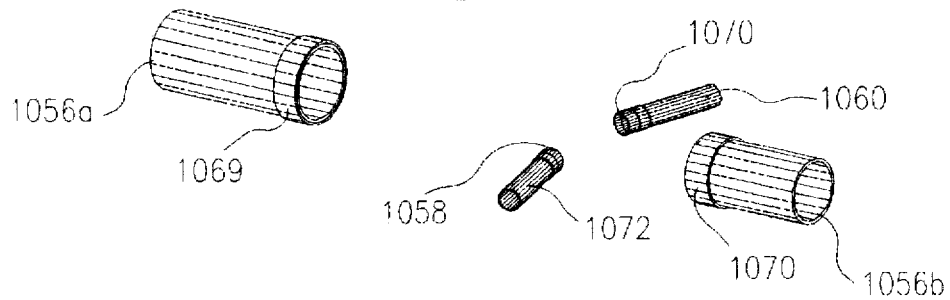
FIG. 76 illustrates in a perspective view the connectors attached to severed ends of the blood vessel, after the pathological portion is resected and removed.
Figure 77:
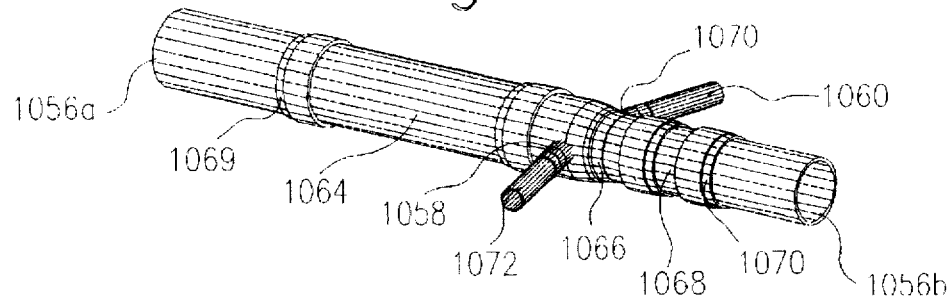
FIG. 77 illustrates in a perspective view the severed vessels ends anastomosed by the assembled graft coupled to the connectors attached to their ends.

After that, the aneurysm 1062 is resected in the predefined lines and the selected connectors are sutured to the severed vessel ends, as shown in FIG. 76. External connectors 1068 and 1070 are sutured to the proximal and distal ends 1056a and 1056b. Internal connectors 1072 and 1074 are sutured to the ends of vessel branches 1058 and 1060. The graft assembled by the three prostheses 1064, 1066 and 1068 is coupled to the sutured connectors, which is illustrated in FIG. 77, trapped air is removed and blood circulation is restored.

The tubular suturing device of the present invention was described for application in anastomotic procedures for resected blood vessels. In the same manner, the invention can find beneficial application also in various transplant interventions. It can be implemented in the current operative techniques or in new methods of operative procedures.

Figure 78:
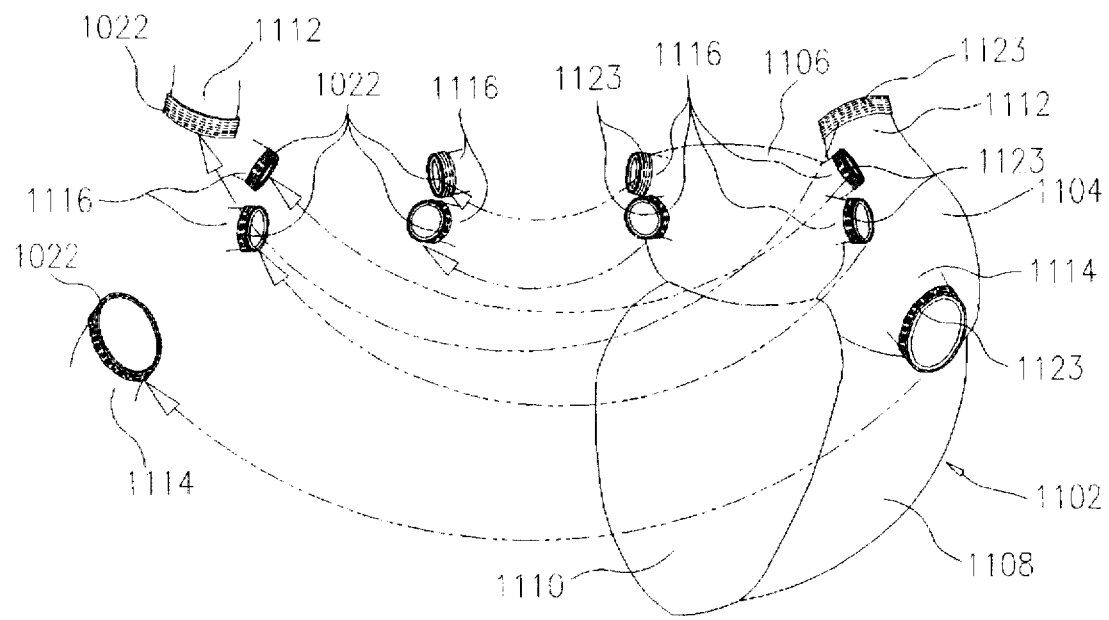
FIG. 78 is a schematic view illustrating a new method for implantation of a total four-chamber heart by coupling of connectors sutured to the origins of the vessels of the recipient to connectors attached to the donor heart, showing coupling of the posterior side of the heart to the incoming veins of the recipient.
Figure 79:
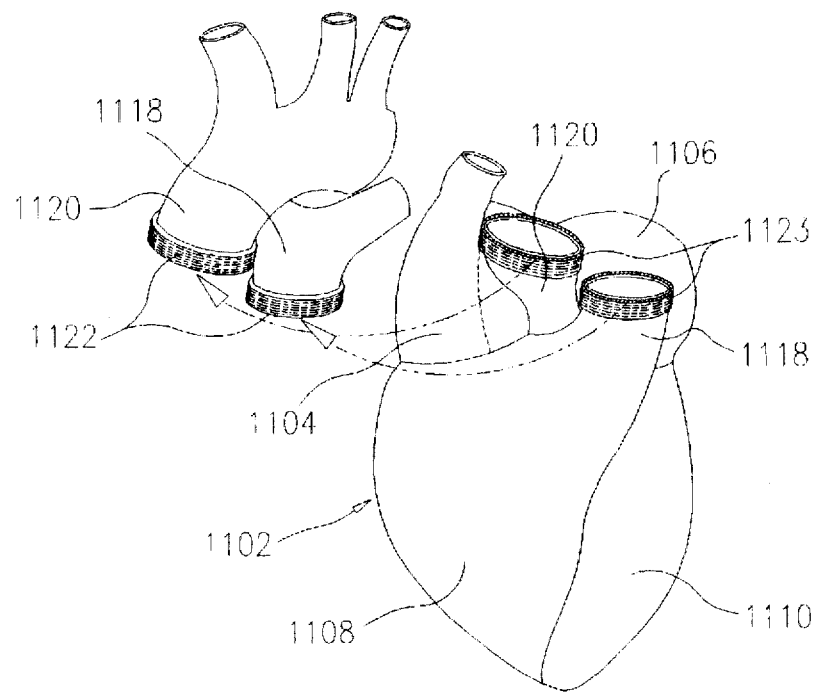
FIG. 79 is a schematic view of the method for implantation of a total four-chamber heart showing coupling of the anterior side of the heart to the outgoing vessels of the recipient.

A new method for heart transplantation is shown in FIGS. 78 and 79. A natural heart 1102 has four chambers—right atrium 1104, left atrium 1106, right ventricle 1108, and left ventricle 1110. Vena Cava Superior 1112 and Vena Cave Inferior 1114 supply venous blood to the right atrium 1104. From there, the blood passes into the right ventricle 1108. The right ventricle 1108 pumps the blood into the Pulmonary Trunk 1116 to the lungs. The oxygenated blood comes from the lungs to the left atrium 1106 by the four pulmonary veins 1116. From there, it passes into the left ventricle 1110, which pumps the blood into the Aorta 1120 to all parts of the body.

The entire heart is removed and replaced with a new donor heart in the new method of heart transplantation (in the current method, portions of the atriums remain in place and a new heart with partially excised atriums is sutured manually to the remaining atrial portions in the recipient). The heart of the recipient is totally excised at the origins of the incoming and outgoing vessels. The donor heart is also excised in the same areas. Tubular connectors 1122 are sutured to the severed vessel ends in the recipient by the tubular suturing device. Correspondingly matching connectors 1124 are attached to the vessel origins of the donor heart 1102 by the tubular suturing device. Coupling of the incoming veins of the recipient to the posterior side of the donor heart 1102 is illustrated in front view in FIG. 78. The two Venae Cavae 1112 and 1114, and the four pulmonary veins 1116 attached with connectors 1122 are shown adjacent to the dorsal side of the donor heart 1102. The donor heart 1102 is rotated and its connectors 1124 are coupled to the connectors 1122 attached to the incoming veins. The Pulmonary mink 1118 and Aorta 1120 with attached connectors 1122 are shown next to the front side of the donor heart 1102 in front view in FIG. 79. The connectors of the donor heart 1124 attached to the origins of the Pulmonary trunk and Aorta are coupled to the connectors 1122 attached to the corresponding vessels of the recipient. After all of the connectors 1122 sutured to the vessels of the recipient are coupled to the connectors 1124 attached to the vessel origins of the donor heart, trapped air is removed and the new heart is stimulated to work. It should be noted, that the drawings describe in general the new operative method of heart transplantation. Intermediate, and modifying the lumen connectors might be needed, when the lumen of the vessels in the recipient does not correspond to the lumen of the vessels of the donor heart.

Although in the new method the new heart is implanted with eight anastomoses, as compared to four anastomoses of the current method in which the two Venae Cavae and the four pulmonary veins together with the remaining walls of the atriums are sutured to the atrial walls of the implanted heart in two anastomoses, the new method does not prolong the time of the operative intervention. Tubular connectors, preferably external, are sutured easily and quickly to the severed vessel ends after the heart is excised and removed. The donor heart is attached with corresponding connectors just before the implantation. During the operative procedure only intermediate connectors might be necessary to select and join to the connectors of the donor heart, in order that they match to the connectors sutured to the vessels in the recipient.

Manual suturing of the atrial walls of the donor heart to the remaining atrial walls of the recipient is a very delicate and troublesome procedure, as this constitutes suturing of muscle tissues. Placing stitches on muscle tissues is always a very difficult procedure. Bleeding starts promptly from the highly vascularized tissues, when the sutures are placed loose. If they are placed too tightly, they easily cut through and bleeding occurs again. For that reason, the current method of transplantation is associated with a very high rate of intra and post operative bleeding.

In the new method of transplantation, connectors are attached steadily and securely to the vessel ends by suturing with the new tubular suturing device. Intraoperative bleeding from the lines of anastomoses is avoided. This substantially shortens the operative procedure. Repeated operative interventions for postoperative bleedings are eliminated. Less blood clots develop around the implanted heart and less drainages are needed, which means less infections. Patients recover faster and multiorgan failure is diminished. There are no inactive atrial wall portions as the donor heart is implanted with the entire atriums. This reduces the risk of thrombogenesis and preserves fully the pumping capacity of the newly implanted heart. All that significantly improves the outcome of the new method of heart transplantation.

The new method of heart transplantation is particularly advantageous when repeated heart transplantation is needed.

In some cases, the donor heart is ultimately rejected by the organism of the recipient and the patient needs a new heart transplant. Repeated transplantations are extremely difficult in the current method, as the remaining atrial portions of the recipient are traumatized and consumed from the previous intervention. In the new method, repeated heart transplantation is a very easy procedure. The previously implanted heart is uncoupled from the connectors sutured to the vessels in the recipient, and a new donor heart attached with matching connectors is coupled to them.

In the same manner, total artificial hearts with four chambers approximating the anatomy of natural heart can be transplanted. The natural heart is excised at the origins of the incoming and outgoing vessels and removed, connectors are sutured to the vessel ends by the new suturing device as described above. A four-chamber artificial heart equipped with matching connectors is coupled to the connectors sutured to the vessels in the recipient. The connectors sutured to the vessels in the recipient can be used later for consequent transplantation with a donor heart, or for replacement with a new artificial heart. A new type of total artificial heart, with four chambers closely approximating the anatomy and physiology of natural heart, will be disclosed in a separate patent application.

Figure 80:
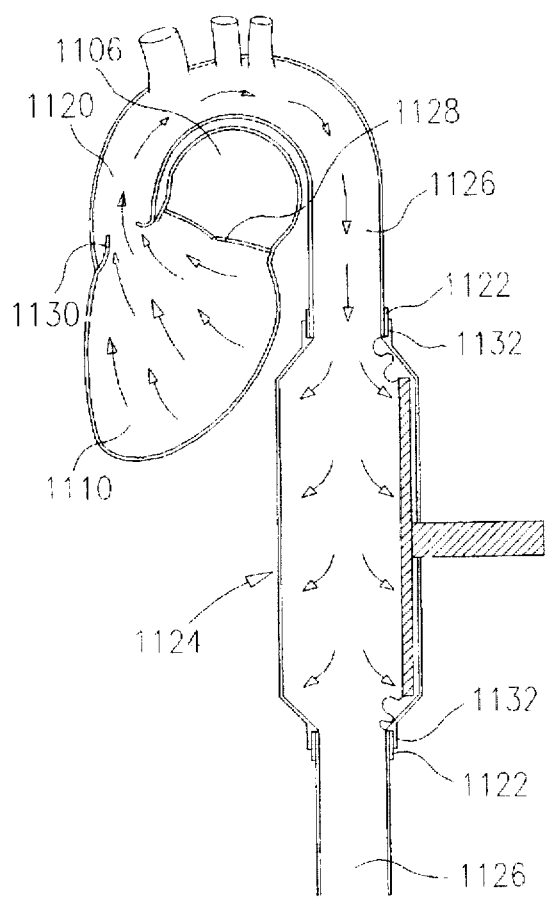
FIG. 80 is a schematic view illustrating a method for left ventricular assistance by implanting a ventricular assist device in place of a resected portion of the thoracoabdominal aorta, showing the assist device expanding synchronously with the contraction of the left ventricle.
Figure 81:
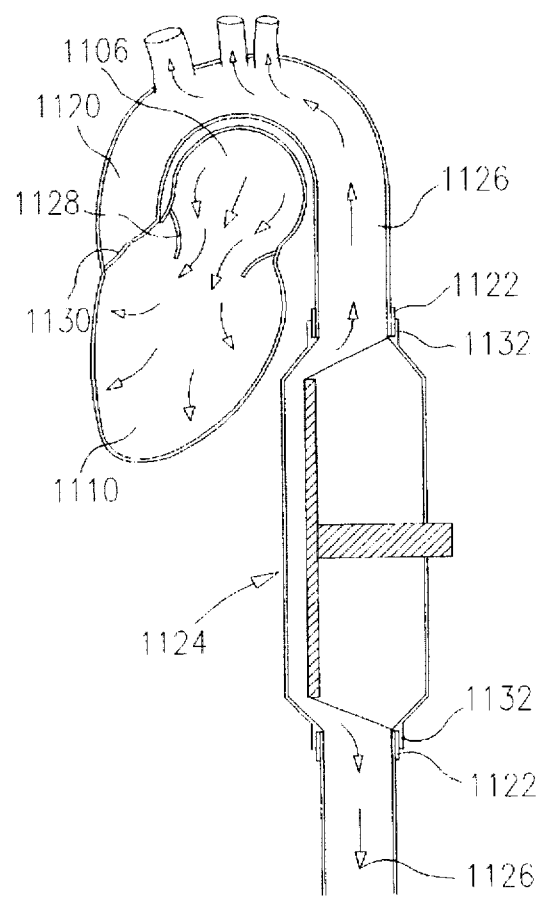
FIG. 81 is a schematic view of the method for left Ventricular assistance, showing the device collapsing synchronously with the expansion of the left ventricle.

The tubular suturing device of the present invention can find application in other new methods of operative interventions. In some patients the function of the failing heart is aided by ventricular assist devices. Ventricular assist devices are used for temporary heart support in patients in whom the cardiac function is temporarily impaired and recovery is expected, or as a bridge to transplantation in cases of irreversible cardiac damage. Ventricular assist devices are implemented for left ventricular assistance in about eighty percents of the patients. A right ventricular or biventricular support is needed for the rest of the cases. By the new tubular suturing device, left ventricular assistance can be performed in a new method, which is illustrated in FIGS. 80 and 81.

A ventricular assist device 1124 is implanted by the tubular suturing to the thoracoabdominal aorta 1126. A portion of the thoracoabdominal aorta 1126 between major branches is resected and two connectors 1122 are attached to the vessel ends by the tubular suturing device. Ventricular assist device 1124 preattached with matching connectors 1130 is coupled to them in line with the circulatory system.

In general, the ventricular assist device 1124 has outer shape approximating the cylindrical form of the thoracoabdominal aorta. It is a volume changing device that is actuated to expand and collapse in synchrony with the activity of the left ventricle 1110. During systolic phase, left ventricle 1110 contracts, aortic valve 1130 opens and atrioventricular valve 1128 closes. Blood is pumped out of the ventricle 1110 into the aorta 1120 as shown in FIG. 80. At the same time, the assist device 1124 is actuated to expand, so the blood volume ejected out of the left ventricle 1110 is actively ingressed into the device. After the contraction of the ventricle is completed, the ventricle enters the diastolic phase. The aortic valve 1130 closes, atrioventricular valve 1128 opens and blood from left atrium 1106 enters the ventricle, as shown in FIG. 81. At this time the ventricular assist device 1124 is actuated to collapse. Blood is pumped out of the assist device in proximal and distal directions. The left ventricle functions in a way as a second atrium. It delivers blood to the expanding ventricular assist device that pumps the blood out into the circulation of the body.

In the current methods of left ventricular assistance, the assist devices are connected between the left atrium and the aorta, or between the left ventricle and the aorta. This decreases the blood volume that the ventricle pumps into the aorta. A very high incidence of extensive intraoperative bleeding of 30–35% is experienced in these methods. This is due to the manual suturing of the ventricular assist devices directly to the myocardial walls, which as explained above are not easy for suturing at all.

The new method is considered advantageous over the current methods of left ventricular assisting for several reasons. First, the very high incidence of extensive bleeding is minimized. By the new tubular suturing device, connectors are sutured easily to the vessel ends and the assist device is coupled to them. Repeated interventions for persistent bleeding are avoided, postoperative recovery is faster, there are much less infections and incidence of multiorgan failure. Second, there is no harm to the heart in the new method, as compared to the current methods producing direct damage on the already impaired heart. Third, the pumping activity of the left ventricle is assisted better. The main object in cardiac assistance, when recovery is expected, is to decrease the work of the ventricle as much as possible. In the new method, the left ventricle pumps actually against no pressure. In the current methods, the amount of blood pumped out the ventricle is decreased, but it still works against the very high aortic pressure. Fourth, the contractility of the left ventricle is completely preserved. In the current methods, certain amounts of blood bypass the left ventricle, which diminishes its filling and expansion. The diminished motility of the cardiac walls for prolonged time leads to fibrotic degenerative changes that reduces the contractility of the myocardium. In the new method, the ventricle fully expands and collapses, which completely preserves its contractility.

When there is no need for further cardiac assistance, the ventricular assist device of the new method can easily be discontinued. It is uncoupled from the connectors attached to the vessel ends and replaced by an artificial graft. The graft is implanted to the already in place connectors. If for some reason the cardiac function deteriorates again, a new ventricular assist device can be easily implanted.

A new type of ventricular assist device, with a form and methods of operation suitable for such application as described above, will be disclosed in a subsequent patent application to be filed later on.

The new tubular suturing device can be very useful in various other transplant procedures. Although the device was designed and described for application predominantly with blood vessels, it can be implemented for anastomosing other organic ducts as well. For example, it can find application for connecting the bile duct in liver transplantation, or for connecting of the urinary duct in kidney transplantations. The device, and/or the new methods of clinching of staples can find application also in various gastrointestinal stapling procedures. Circular and linear staplers have found well established application in gastrointestinal surgery, so further tests and experimentations are needed in this area to determine the presence of benefits over the currently used gastrointestinal staplers.

The general invention described herein changes significantly the outcome of operative interventions requiring anastomoses of tubular structures. Reliable vascular anastomoses can be accomplished in a much shorter time than with the currently available methods. The shortened time of operative procedures produces less ischemic changes in the tissues and organs deprived of blood supply during the procedure. The precise and reliable suturing by staples minimizes the complications of bleeding from the suture lines. Applications of drainages and development of blood clots around the anastomoses promoting development of infections are also minimized. Repeated operative interventions for significant postoperative bleedings are avoided. The ends of blood vessels are precisely anastomosed without any changes in their lumen and anatomical configuration. This reduces the possibilities for obliteration of the anastomoses or for thromboembolic complications. It will become possible to perform new, more efficient surgical procedures. All that will substantially improve the outcome in many operative interventions in cardiovascular and transplant surgery.

The foregoing description of the principles of operation of the preferred embodiments of the tubular suturing device made in conjunction with the various figures of the drawings are intended to be illustrative of the practice of the invention. Without departing from the principles of operation of the present invention, other embodiments and variations can be utilized. For example, the device can be implemented for application with structures having only outer or only inner tubular configurations. The complete annular form of the device can be interrupted and the device can be used for creating suture lines to structures with arcuate surfaces. The device can be produced with magazines for storing multiple staples for effecting multiple consequent stapling actions. Thus, the information disclosed in the description of the present invention is intended to be representative of the principles that I have described. It will thus be seen, that the objects of the invention set forth above and those made apparent from the proceeding are efficiently attained, and as certain changes may be made without departing from the scope of the invention, it is intended that all matter contained in the above description or shown in the accompanying drawings shall be interpreted as illustrative, but not in a limiting sense. It is also to be understood, that the following claims are intended to cover all of the generic and specific features of the invention herein described and all statements of the scope of the invention which, as a matter of language, might be said to fall therebetween.

What is claimed is:

1. A suturing assembly for attaching a connector to an end of a tubular anatomical structure, said suturing assembly comprising:
   (a) a suturing device comprising a rigid body with a tubular suturing surface;
   (b) multiple staples disposed within respective receptacles arrayed radially along said suturing surface of said rigid body, each of said staples comprising two parallel prongs joined by a crosspiece;
   (c) actuating means that by an applied force move into respective spaces and eject simultaneously said multiple staples out of said receptacles; and
   (d) a tubular connector comprising inner and outer tubular means affixed firmly to each other, one of said tubular means being, sufficiently rigid for preventing penetration of the staples and for clinching the stapes upon ejection, said tubular means also sustaining a predetermined coupling form, and the other of said tubular means for withholding clinched staples, said other tubular means being sufficiently soft to be penetrated by ejected staples and with a sufficient tensile strength to withhold clinched staples, wherein said connector is positioned at the end of said tubular anatomical structure with the soft tubular means of said connector abutting said tubular anatomical structure on one side, while said suturing device with said suturing surface is abutting said tubular anatomical structure on the other side.

2. The suturing assembly according to claim 1, wherein said actuating means further comprise multiple rigid radial plates with predetermined sloped edges, said sloped edges producing multiple forces ejecting simultaneously said staples out of said receptacles when said plates are moved in an axial direction.

3. The suturing assembly according to claim 1, wherein said staples are disposed within multiple receptacles arrayed along the inner side of said rigid body and are adapted to suture said tubular connector inserted into said tubular anatomical structure.

4. The suturing assembly according to claim 1, wherein said receptacles further comprise arcuate ends curved in a convergent direction which direct and clinch the prongs of the ejected staples in the convergent direction.

5. The suturing assembly according to claim 4, wherein the rigid tubular means of said tubular connector has a tubular concave surface that clinches additionally the prongs of the ejected staples in the convergent direction.

6. The suturing assembly according to claim 1, wherein the tubular surface of the rigid tubular means of said tubular connector is curved sufficiently to clinch alone the prongs of the ejected staples.

7. The suturing assembly according to claim 6, wherein said connector is positioned externally to said tubular anatomical structure, and said tubular surface of said rigid tubular means is adapted to clinch the prongs of the ejected staples in a convergent direction.

8. The suturing assembly according to claim 6, wherein said connector is positioned internally to said tubular anatomical structure, and said tubular surface of said rigid tubular means is adapted to clinch the prongs of the ejected staples in a divergent direction.

9. A suturing assembly for attaching a connector to an end of a tubular anatomical structure, said suturing assembly comprising:
   (a) a tubular suturing device comprising a tubular rigid body containing multiple staples disposed within respective receptacles arrayed radially along a suturing surface of said rigid body and actuating means that by an applied force move in a predetermined manner to eject simultaneously said staples out of said receptacles; and
   (d) a tubular connector comprising inner and outer tubular means affixed firmly to each other, one of said tubular means being a sufficiently rigid tubular portion for preventing penetration of the staples and for clinching the staples upon ejection and the other of said tubular means being a soft tubular portion and having a sufficient tensile strength for withholding clinched staples, wherein said connector is positioned at the end of said tubular anatomical structure with said soft portion abutting said tubular anatomical structure on one side, while said suturing device with said suturing surface is abutting said tubular anatomical structure on the other side.

10. The suturing assembly according to claim 9, wherein said actuating means further comprise multiple rigid radial plates with predetermined sloped edges, said sloped edges producing multiple forces ejecting simultaneously said staples out of said receptacles when said plates are moved in an axial direction.

11. The suturing assembly according to claim 9, wherein said staples are disposed within multiple receptacles arrayed along the inner side of said rigid body and are adapted to suture said tubular connector inserted into said tubular anatomical structure.

12. The suturing assembly according to claim 9, wherein said receptacles further comprise arcuate ends curved in a convergent direction which direct and clinch the ejected staples in the convergent direction.

13. The suturing assembly according to claim 12, wherein said rigid tubular means of said connector has a tubular concave surface that clinches additionally the ejected staples in the convergent direction.

14. The suturing assembly according to claim 9, wherein the tubular surface of said rigid tubular means of said tubular connector is sufficiently curved to clinch alone the ejected staples.

15. The suturing assembly according to claim 14, wherein said connector is positioned externally to said tubular anatomical structure, and said tubular surface of said rigid tubular means is adapted to clinch the ejected staples in a convergent direction.

16. The suturing assembly according to claim 14, wherein said connector is positioned internally to said tubular anatomical structure, and said tubular surface of said rigid tubular means is adapted to clinch the ejected staples in a divergent direction.

17. A suturing assembly for attaching a tubular connector to an end of a tubular anatomical structure, said suturing assembly comprising:
  (a) a tubular suturing device comprising a tubular rigid body containing multiple staples disposed within respective receptacles arrayed radially along a suturing surface of said rigid body and actuating means that by an applied force move in a predetermined manner to eject simultaneously said staples out of said receptacles; and
  (b) a tubular connector comprising inner and outer tubular means affixed firmly to each other, one of said tubular means being a sufficiently rigid portion for preventing penetration of the staples and for clinching the staples upon ejection, and the other of said tubular means being a soft portion and having a sufficient tensile strength for withholding clinched staples, wherein the ejected staples pierce said tubular anatomical structure and said soft portion and are clinched by said rigid portion of said connector.

18. The suturing assembly according to claim 17, wherein said actuating means further comprise multiple rigid radial plates with predetermined sloped edges, said sloped edges producing multiple forces ejecting simultaneously said staples out of said receptacles, when said plates are moved in an axial direction.

19. The suturing assembly device according to claim 17, wherein said staples are disposed within multiple receptacles arrayed along the inner side of said rigid body and are adapted to suture said tubular connector inserted into said tubular anatomical structure.

20. The suturing assembly according to claim 17, wherein said connector is positioned externally to said tubular anatomical structure, and said rigid portion of said connector is adapted to clinch convergently the ejected staples.

21. The suturing assembly according to claim 17, wherein said connector is positioned internally to said tubular anatomical structure, and said rigid portion of said connector is adapted to clinch divergently the ejected staples.

22. The suturing assembly according to claim 17, wherein receptacles further comprise arcuate ends curved in a convergent direction which clinch the ejected staples in the convergent direction.

23. The suturing assembly according to claim 22, wherein said rigid portion of said connector has a tubular concave surface that clinches additionally the ejected staples in the convergent direction.

24. A method for accomplishing an end-to-end anastomosis of two tubular anatomical structures by attaching connectors to their ends, said method comprising the steps of:
  (a) suturing a tubular connector to the end of each of said two tubular anatomical structures by a tubular suturing device ejecting simultaneously multiple staples in a radial direction, said connector comprising inner and outer tubular means affixed to each other, one of said portions tubular means being a sufficiently rigid portion for preventing penetration of the staples and for clinching the staples upon ejection, said tubular means having a predefined coupling surface and the other of said tubular means being a soft portion and having a sufficient tensile strength for withholding clinched staples; and
  (b) joining the two tubular anatomical structures by coupling the tubular connectors sutured to their ends.

25. The method for accomplishing an end-to-end anastomosis of two tubular structures according to claim 24, wherein said step of suturing further comprises ejecting staples in an outward radial direction by moving axially multiple rigid radial plates with predetermined sloped outer edges.

26. The method for accomplishing an end-to-end anastomosis of two tubular structures according to claim 24, wherein said step of suturing further comprises ejecting staples in an inward radial direction by said tubular suturing device for attaching the tubular connectors inserted into said tubular structures.

27. The method for accomplishing an end-to-end anastomosis of two tubular structures according to claim 24, wherein said step of suturing further comprises clinching the ejected staples in a convergent direction by receptacles with arcuate ends curved convergently.

28. The method for accomplishing an end-to-end anastomosis of two tubular structures according to claim 27, wherein said step of suturing further comprises clinching additionally the ejected staples in the convergent direction by said rigid portion of said connector.

29. The method for accomplishing an end-to-end anastomosis of two tubular structures according to claim 24, wherein said step of suturing further comprises clinching the ejected staples by said rigid portion of said connector.

30. The method for accomplishing an end-to-end anastomosis of two tubular structures according to claim 29, wherein said step of suturing further comprises ejecting staples in an outward radial direction and clinching convergently the ejected staples.

31. The method for accomplishing an end-to-end anastomosis of two tubular structures according to claim 29, wherein said step of suturing further comprises ejecting staples in an inward radial direction and clinching divergently the ejected staples.

32. A method for attaching a tubular connector to an end of a tubular anatomical structure, said method comprising the steps of:
  (a) positioning the end of the tubular anatomical structure between a tubular suturing device containing multiple staples disposed within radially arrayed receptacles and a tubular connector comprising inner and outer tubular means, one of said tubular means being a sufficiently rigid portion for preventing penetration of the staples and for clinching the staples upon ejection and the other of said tubular means being a soft portion and having a sufficient tensile strength for withholding clinched staples; and (b) suturing said tubular connector to said tubular anatomical structure by ejecting said staples out of said receptacles, wherein the ejected staples pierce said tubular anatomical structure and said soft portion of said tubular connector.

33. The method for attaching a connector to an end of a tubular anatomical structure according to claim 32, wherein said step of suturing further comprises ejecting said staples in an outward radial direction by moving axially multiple rigid radial plates with predetermined sloped outer edges.

34. The method for attaching a connector to an end of a tubular anatomical structure according to claim 32, wherein said step of suturing further comprises ejecting said staples in an inward radial direction for attachment of said connector inserted into said tubular structure.

35. The method for attaching a connector to an end of a tubular anatomical structure according to claim 32, wherein said step of suturing further comprises clinching the ejected staples in a convergent direction by receptacles with arcuate ends curved convergently.

36. The method for attaching a connector to an end of a tubular anatomical structure according to claim 35, wherein said step of suturing further comprises clinching additionally the ejected staples in the convergent direction by said rigid portion of said connector.

37. The method for attaching a connector to an end of a tubular anatomical structure according to claim 32, wherein said step of suturing further comprises clinching the ejected staples by said rigid portion of said connector.

38. The method for attaching a connector to an end of a tubular anatomical structure according to claim 37, wherein said step of suturing further comprises ejecting said staples in an outward radial direction and clinching convergently the ejected staples.

39. The method for attaching a connector to an end of a tubular anatomical structure according to claim 37, wherein said step of suturing further comprises ejecting said staples in an inward radial direction and clinching divergently the ejected staples.

40. A method for attaching a connector to an end of a tubular anatomical structure, said method comprising the steps of:
  (a) positioning the end of the tubular anatomical structure between a tubular suturing device containing multiple staples disposed within radially arrayed receptacles and a tubular connector comprising inner and outer tubular means, one of said tubular means being a sufficiently rigid portion for preventing penetration of the staples and for clinching the staples upon ejection and the other of said tubular means being a soft portion and having a sufficient tensile strength for withholding clinched staples; and
  (b) suturing of said tubular connector to said tubular anatomical structure by ejecting said staples out of said receptacles, wherein the ejected staples pierce said tubular structure and said soft portion and are clinched by said rigid portion of said connector.

41. The method for attaching a connector to an end of a tubular anatomical structure according to claim 40, wherein said step of suturing further comprises ejecting said staples in an outward radial direction by moving axially multiple rigid radial plates with predetermined sloped outer edges.

42. The method for attaching a connector to an end of a tubular anatomical structure according to claim 40, wherein said step of suturing further comprises ejecting said staples in an inward radial direction for attachment of said tubular connector inserted into the end of said tubular structure.

43. The method for attaching a connector to an end of a tubular anatomical structure according to claim 40, wherein said step of suturing further comprises clinching convergently the ejected staples by said rigid portion of said connector that is positioned externally to said tubular structure.

44. The method for attaching a connector to an end of a tubular anatomical structure according to claim 40, wherein said step of suturing further comprises clinching divergently the ejected staples by said rigid portion of said connector that is positioned internally to said tubular structure.

45. The method for attaching a connector to an end of a tubular anatomical structure according to claim 40, wherein said step of suturing further comprises clinching convergently the ejected staples by receptacles with arcuate ends curved convergently.

46. The method for attaching a connector to an end of a tubular anatomical structure according to claim 45, wherein said steps of suturing further comprises clinching convergently the ejected staples by said rigid portion of said connector.

47. A tubular connector for attachment to an end of a tubular anatomical structure by a tubular suturing device ejecting simultaneously multiple staples in a radial direction, said connector comprising:
  inner and outer tubular means firmly affixed together, one of said tubular means being a sufficiently rigid tubular portion for preventing penetration of the staples and for clinching the staples upon ejection, said tubular means including a predetermined coupling surface and the other of said tubular means being a soft tubular portion and having a sufficient tensile strength for withholding clinched staples, wherein said connector is positioned at the end of said tubular anatomical structure with said soft portion abutting said tubular structure.

48. The tubular connector according to claim 47, wherein said rigid portion is the outer portion and said soft portion is the inner portion of said connector that is positioned externally to said tubular anatomical structure.

49. The tubular connector according to claim 47, wherein said rigid portion is the inner portion and said sole portion is the outer portion of said connector that is positioned internally to said tubular anatomical structure.

50. The tubular connector according to claim 49, wherein said connector has an internal caliber approximating the internal caliber of said anatomical tubular structure.

51. A tubular connector for attachment to an end of a tubular anatomical structure by a tubular suturing device ejecting simultaneously multiple staples in a radial direction, said connector comprising:
  inner and outer tubular means firmly affixed together, one of said tubular means having a rigid tubular portion and being sufficiently hard for preventing penetration of the staples and for clinching the staples upon ejection and the other of said tubular means being a soft portion and having a sufficient tensile strength for withholding clinched staples, wherein said connector is positioned at the end of said tubular anatomical structure with said soft portion abutting said tubular anatomical structure.

52. The tubular connector according to claim 51, wherein said rigid portion is the outer portion and said soft portion is the inner portion of said connector that is positioned externally to said tubular anatomical structure.

53. The tubular connector according to claim 51, wherein said rigid portion is the inner portion and said soft portion is the outer portion of said connector that is positioned internally to said tubular anatomical structure.

54. The tubular connector according to claim 53, wherein said connector has an internal caliber approximating the internal caliber of said tubular anatomical structure.

55. A method for accomplishing anastomosis of two tubular anatomical structures by attaching connectors to their ends, said method comprising the steps of:

(a) suturing a tubular connector to the end of each said tubular anatomical structures by a tubular suturing device ejecting staples radially, said connector comprising inner and outer tubular means affixed to each other, one of said tubular means being a sufficiently rigid portion for preventing penetration of the staples and for clinching the staples upon ejection, said tubular means having a predefined coupling surface and the other of said tubular means being a soft portion and having a sufficient tensile strength for withholding clinched staples; and (b) coupling the sutured tubular connectors to a tubular graft adapted at the ends with rigid surfaces that match correspondingly to the coupling surfaces of the sutured connectors.

* * * * *